US009328391B1

(12) United States Patent
Chang et al.

(10) Patent No.: US 9,328,391 B1
(45) Date of Patent: May 3, 2016

(54) CLONING AND EXPRESSION OF HIV-1 DNA

(75) Inventors: Nancy T. Chang, Houston, TX (US); Robert C. Gallo, Bethesda, MD (US); Flossie Wong-Staal, Germantown, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 06/693,866

(22) Filed: Jan. 23, 1985

Related U.S. Application Data

(63) Continuation-in-part of application No. 06/659,339, filed on Oct. 10, 1984, now abandoned, which is a continuation-in-part of application No. 06/643,306, filed on Aug. 22, 1984, now abandoned.

(51) Int. Cl.
*C12Q 1/68* (2006.01)
*C12Q 1/70* (2006.01)

(52) U.S. Cl.
CPC .............. *C12Q 1/703* (2013.01); *C12Q 1/6813* (2013.01)

(58) Field of Classification Search
None
See application file for complete search history.

(56) References Cited

U.S. PATENT DOCUMENTS

| | | | |
|---|---|---|---|
| 4,358,535 | A | 11/1982 | Falkow et al. |
| 4,401,756 | A | 8/1983 | Gillis |
| 4,520,113 | A | 5/1985 | Gallo |
| 4,725,669 | A | 2/1988 | Essex |
| 4,735,896 | A | 4/1988 | Wang |
| 6,531,276 | B1 | 3/2003 | Luciw |

OTHER PUBLICATIONS

Gubler et al. (A simple and very efficient method for generating cDNA libraries, Gene, 25 (1983) 263-269).*
Suggs et al. (Use of synthetic oligonucleotides as hybridization probes: Isolation of cloned cDNA sequences for human p2-microglobulin, Proc. NatL Acad. Sci. USA vol. 78, No. 11, pp. 6613-6617, Nov. 1981).*
Anilionis, et al. *Nature* 294:275-278, 1981.
*Alice Corporation Pty. Ltd.* v. *CLS Bank International et al.*, U.S. Supreme Court, No. 13-298; Decided Jun. 19, 2014.
Association for *Molecular Pathology* et al. v. *Myriad Genetics, Inc., et al.*; U.S. Supreme Court, No. 12-398; Decided Jun. 13, 2013.
Mayo Collaborative Services, *DBA Mayo Medical Laboratories, et al.* v. *Prometheus Laboratories, Inc.*; U.S. Supreme Court, No. 10-1150; Decided Mar. 20, 2012.
*Bilski et al.* v. *Kappos*, Under Secretary Ofcommerce for Intellectual Property and Director, Patent and Trademark Office; U.S. Supreme Court, No. 08-964; Decided Jun. 28, 2010.
*University of Utah Research Foundation, The Trustees of the University of Pennsylvania, HSC Research and Development Limited Partnership, Endorecherche, Inc., and Myriad Genetics, Inc.* v. *Ambry Genetics Corporation*; Fed. Cir. 2014-1361, -1366; Decided Dec. 17, 2014.
In Re Roslin Institute (Edinburgh); Fed. Cir. 2013-1407; Decided May 8, 2014.
*Classen Immunotherapies, Inc.*, v. *Biogen IDEC*, and *Glaxosmithkline, and Merck & Co., Inc.*, and *Chiron Corporation, Kaiser-Permanente, Inc., Kaiser Permanente Ventures, Kaiser Permanente International, Kaiser Permanente Insurance Company, The Permanente Federation, LLC, The Permanente Company, LLC, The Permanente Foundation, The Permanente Medical Group, Inc., Kaiser Foundation Hospitals, Kaiser Foundation Added Choice Health Plan, Inc.*, and *Kaiser Foundation Health Plan Inc.*; Fed. Cir. 2006-1634,-1649; Decided Aug. 31, 2011.
*Ariosa Diagnostics, Inc., Natera, Inc., DNA Diagnostics Center, Inc.*, v *Sequenom, Inc., Sequenom Center for Molecular Medicine, LLC, ISIS Innovation Limited*; Fed Cir. 2014-1139, 2014-1144; Decided: Jun. 12, 2015.
*Ariosa Diagnostics, Inc., Natera, Inc., DNA Diagnostics Center, Inc.*, v *Sequenom, Inc., Sequenom Center for Molecular Medicine, LLC, ISIS Innovation Limited*; Fed Cir. 2014-1139, 2014-1144; Decided: Dec. 2, 2015.
Alizon M., et al.; "Molecular cloning of lymphadenopathy-associated virus", *Nature*, Dec. 20, 1984; vol. 312(5996), pp. 757-760.
Anilionis A. et al.; "Structure of the glycoprotein gene in rabies virus", *Nature*, Nov. 19, 1981; vol. 294, pp. 275-278.
Arya S.K., et al.; "Homology of Genome of AIDS-Associated Virus with Genomes of Human T-Cell Leukemia Viruses"; *Science*, vol. 225, Aug. 31, 1984; pp. 927-930.
Barre-Sinoussi, F. et al.; "Isolation of a T-Lymphotropic retrovirus from a Patient at Risk for Acquired Immune Deficiency Syndrome (AIDS)"; *Science*, vol. 220, May 20, 1983; pp. 868-870.
Chang, N.T., et al.; :Expression in *Escherichia coli* of Open Reading Frame Gene Segments of HTLV-III; *Science.*, vol. 228, 1985; pp. 93-96.
Chang, N.T., et al.; :An HTLV-III peptide produced by recombinant DNA is immunoreactive with sera from patients with AIDS; *Nature.*, vol. 315, 1985; pp. 151-154.
European Search Report for the European Patent Office application, filed Oct. 10, 1985.
Feorino P.M., et al.; "Lymphadenopathy associated virus infection of a blood donor-recipient pair with acquired immunodeficiency syndrome"; *Science.*, vol. 225, Jul. 6, 1984; pp. 69-72.
Fisher, A.G..; "A molecular clone of HTLV-III with biological activity", Nature (Jul. 18, 1985), vol. 316, pp. 262-265.
Gait M.J.; Oligonucleotide synthesis—A practical approach, *IRL Press Limited*, P.O. Box 1, Eynsham, Oxford OX8IJJ, England, 1984, ISBN 0-904147-74-6.

(Continued)

*Primary Examiner* — Gary Benzion
*Assistant Examiner* — Aaron Priest
(74) *Attorney, Agent, or Firm* — Siegfried J. W. Ruppert; Susan S. Rucker

(57) ABSTRACT

The determination of the nucleotide sequence of HIV-1 DNA; identification, isolation and expression of HIV-1 DNA sequences which encode immunoreactive polypeptides by recombinant DNA methods and production of viral RNA are disclosed. Such polypeptides can be employed in immunoassays to detect HIV-1.

22 Claims, 28 Drawing Sheets

(56) References Cited

OTHER PUBLICATIONS

Gallo R. etal.; Fequent detection and isolation of cytopathic retroviruses (HTLV-III) from patients with AIDS and at risk for AIDS, Science (1984) vol. 224, No. 4648, pp. 500-503.
Gelmann, E.P.; "Molecular cloning of a unique human T-cell leukemia virus (HTLV-IIMo)"; Proc. Natl. Acad. Sci. USA., vol. 81, Feb. 1984; pp. 993-997.
Gray M.R. et al.; "Open reading frame cloning: Identification, cloning, and expression of open reading frame DNA ", Proc. Nat!. Acad. Sci. USA, vol. 79, Nov. 1982; pp. 6598-6602.
Ghrayeb J. etal.; "Secretion cloning vectors in *Escherichia coli*", *EMBO Journal*, vol. 3, No. 10, 1984; pp. 2437-2442.
Hahn, B.H., et al.; "Molecular cloning and characterization of the HTLV-III virus associated with AIDS", *Nature*(Nov. 1984), vol. 312, pp. 166-169.
Interference No. 102,822.
Interference No. 105,290.
Interference No. 105,291.
Klatzmann D., et al.; "T-lymphocyte T4 molecule behaves as the receptor for human retrovirus LAV"; *Nature.*, vol. 312, Dec. 20, 1984; pp. 767-768.
Manzari V., et al.; "Human T-cell leukemia-lymphoma virus (HTLV): cloning of an integrated defective provirus and flanking cellular sequences"; *Proc. Natl. Acad. Sci. USA*, vol. 80, No. 12, Jun. 1, 1983; pp. 1574-1578.
Marx J.L.; A Virus by Any Other Name . . . , *Science*, Mar. 22, 1985; vol. 227, No. 4693, pp. 1449-1451.
Marx J.L.; "The AIDS Virus—Well Known But a Mystery", Science, Apr. 24, 1987; vol. 236, No. 4800, pp. 390-392.
Muesing, M.A., et al.; "Nucleic acid structure and expression of the human AIDS/lymphadenopathy retrovirus"; *Nature.*, vol. 313, Feb. 7, 1985; pp. 450-458.
*Novartis Vaccines and Diagnostics, Inc.* V. *Institut Pasteur* et al.; Civil Case No. 07-00034.
*Novartis Vaccines and Diagnostics, Inc.* V. *United States Department of Health and Human Services* et al.; Civil Case No. 07-00034.
Ratner, L., et al.; "Complete nucleotide sequence of the AIDS virus", HTLV-III, *Nature*, vol. 313, Jan. 24, 1985; pp. 277-284.
Sarngadharan, M.G., et al.; "Antibodies reactive with human T-Iymphotropic retroviruses (HTLV-III) in the srum of patients with AIDS", *Science*(May 4, 1984), vol. 224; pp. 506-508.
Schupbach J. et al.; "Serological analysis of a subgroup of human T-lymphotropic retroviruses (HTLV-III) associated with AIDS", *Science*(1984) vol. 224, No. 4648, pp. 503-505.
Seiki M., et al.; "Human adult T-cell leukemia virus: molecular cloning of the provirus DNA and the unique terminal structure", *Proc. Natl. Acad. Sci. USA*, vol. 79, No. 22, Nov. 1, 1982; pp. 6899-6902.
Seiki M., etal.; "Human adult T-cell leukemia virus: complete nucleotide sequence of the provirus genome integrated in leukemia cell DNA", *Proc. Natl. Acad. Sci. USA*, vol. 80, No. 12, Jun. 1, 1983; pp. 3618-3622.
Suggs, S.V.,et al.; "Use of synthetic oligonucleotides as hybridization probes: Isolation of cloned cDNA sequences for human β-microglobulin", Proc. Natl. Acad. Sci. U.S.A., vol. 78, No. 11, pp. 6613-6617.
*The United States of America.* V. *Institut Pasteur* et al.; Civil Case No. 07-00034
Weinstock G.M. etal., "Open reading frame expression vectors: a general method for antigen production in *Escherichia coli* using protein fusions to beta-galactosidase", *Proc. Natl. Acad. Sci. USA*, (1984) vol. 80, No. 14, pp. 4432-4436.
Weiss R., et al. *RNA Tumor Viruses*(2d ed.), vol. 2, (1985) pp. 1054-1123.
Wirth D.F. et al., "Rapid identification of *Leishmania* species by specific hybridization of kinetoplast DNA in cutaneous lesions", *Proc. Natl. Acad. Sci. USA*, (1982) vol. 79, pp. 6999-7003.

* cited by examiner

FIG. 3 (Continued)

```
                                                                Hind III
BH10  ACCAAAAGAACCTTTTAGAGACTATGTAGACCGGTTCTATAAAACTCTAAGAGCCGAGCAAGCTTCACAGGAGGT   1271
       ProLysGluProPheArgAspTyrValAspArgPheTyrLysThrLeuArgAlaGluGlnAlaSerGlnGluVal          313
BH5   ------G-----C-------------------------------------------------------------A--
                                                                 Aha III
BH10  AAAAAATTGGATGACAGAAACCTTGTTGGTCCAAAATGCGAACCCAGATTGTAAGACTATTTTAAAAGCATTGGG   1346
       LysAsnTrpMetThrGluThrLeuLeuValGlnAsnAlaAsnProAspCysLysThrIleLeuLysAlaLeuGly          338
BH5   ---------------------------------------------------------------------------

BH10  ACCAGCGGCTACACTAGAAGAAATGATGACAGCATGTCAGGGAGTAGGAGGACCCGGCCATAAGGCAAGAGTTTT   1421
       ProAlaAlaThrLeuGluGluMetMetThrAlaCysGlnGlyValGlyGlyProGlyHisLysAlaArgValLeu          363
BH5   ---------------------------------------------------------------------------

BH10  GGCTGAAGCAATGAGCCAAGTAACAAATACAGCTACCATAATGATGCAGAGAGGCAATTTTAGGAACCAAAGAAA   1496
       AlaGluAlaMetSerGlnValThrAsnThrAlaThrIleMetMetGlnArgGlyAsnPheArgAsnGlnArgLys          388
BH5   -------------------------T--A---------------A------------------------------
                               SerThr

BH10  GATGGTTAAGTGTTTCAATTGTGGCAAAGAAGGGCACACAGCCAGAAATTGCAGGGCCCCTAGGAAAAAGGGCTG   1571
       MetValLysCysPheAsnCysGlyLysGluGlyHisThrAlaArgAsnCysArgAlaProArgLysLysGlyCys          413
      A--T--------------------------------T---A----------A---------A----GA-----
                                          Ile              Lys              Arg
          |---------Direct Repeat-------------|              |--POL     Bgl II
BH10  TTGGAAATGTGGAAAGGAAGGACACCAAATGAAAGATTGTACTGAGAGACAGGCTAATTTTTTAGGGAAGATCTG   1646
       TrpLysCysGlyLysGluGlyHisGlnMetLysAspCysThrGluArgGlnAlaAsnPheLeuGlyLysIleTrp          438
                                                             PhePheArgGluAspLeu               6
BH5   ---------------------------------------------------------------------------
                          |---------Direct Repeat-----------|--Direct
BH10  GCCTTCCTACAAGGGAAGGCCAGGGAATTTTCTTCAGAGCAGACCAGAGCCAACAGCCCCACCATTTCTTCAGAG   1721
       ProSerTyrLysGlyArgProGlyAsnPheLeuGlnSerArgProGluProThrAlaProProPheLeuGlnSer          463
       AlaPheLeuGlnGlyLysAlaArgGluPheSerSerGluGlnThrArgAlaAsnSerProThrIleSerSerGlu           31
BH5   ---------------------------------------------------------------------------
```

FIG. 3 (Continued)

```
BH10  GGAATGGATGGCCCAAAAGTTAAACAATGGCCATTGACAGAAGAAAAAATAAAAGCATTAGTAGAAATTTGTACA  2246
      GlyMetAspGlyProLysValLysGlnTrpProLeuThrGluGluLysIleLysAlaLeuValGluIleCysThr
BH5   ---------------------------------------------------------------------------

BH10  GAAATGGAAAAGGAAGGGAAAATTTCAAAAATTGGGCCTGAGAATCCATACAATACTCCAGTATTTGCCATAAAG  2321
      GluMetGluLysGluGlyLysIleSerLysIleGlyProGluAsnProTyrAsnThrProValPheAlaIleLys
BH5   -----------------------------------------A----------------------------A----

BH10  AAAAAAGACAGTACTAAATGGAGAAAATTAGTAGATTTCAGAGAACTTAATAAGAGAACTCAAGACTTCTGGGAA  2396
      LysLysAspSerThrLysTrpArgLysLeuValAspPheArgGluLeuAsnLysArgThrGlnAspPheTrpGlu
BH5   ----------------------------------------------------G----------------------
                                                         Arg

BH10  GTTCAATTAGGAATACCACATCCCGCAGGGTTAAAAAAGAAAAAATCAGTAACAGTACTGGATGTGGGTGATGCA  2471
      ValGlnLeuGlyIleProHisProAlaGlyLeuLysLysLysLysSerValThrValLeuAspValGlyAspAla
BH5   --------G------------------------------------------------------------------

BH10  TATTTTTCAGTTCCCTTAGATGAAGACTTCAGGAAGTATACTGCATTTACCATACCTAGTATAAACAATGAGACA  2546
      TyrPheSerValProLeuAspGluAspPheArgLysTyrThrAlaPheThrIleProSerIleAsnAsnGluThr
BH5   -----------------------------------------------------------------T---------

BH10  CCAGGGATTAGATATCAGTACAATGTGCTTCCACAGGGATGGAAAGGATCACCAGCAATATTCCAAAGTAGCATG  2621
      ProGlyIleArgTyrGlnTyrAsnValLeuProGlnGlyTrpLysGlySerProAlaIlePheGlnSerSerMet
BH5   -------G-G-----------------------------------------------------------------
             SerGly
                      Aha III
BH10  ACAAAAATCTTAGAGCCTTTTAAAAAACAAAATCCAGACATAGTTATCTATCAATACATGGATGATTTGTATGTA  2696
      ThrLysIleLeuGluProPheLysLysGlnAsnProAspIleValIleTyrGlnTyrMetAspAspLeuTyrVal
BH5   ----------------------G------------------------T---------------------------
                           Arg
```

FIG. 3 (Continued)

```
BH10  AAACTACCCATACAAAAGGAAACATGGGAAACATGGTGGACAGAGTATTGGCAAGCCACCTGGATTCCTGAGTGG  3371
      LysLeuProIlaGlnLysGluThrTrpGluThrTrpTrpThrGluTyrTrpGlnAlaThrTrpIleProGluTrp         581
BH5   ------------------A--------------------------------------------------------
                                      Kpn I
BH10  GAGTTTGTTAATACCCCTCCTTTAGTGAAATTATGGTACCAGTTAGAGAAAGAACCCATAGTAGGAGCAGAAACC  3446
      GluPheValAsnThrProProLeuValLysLeuTrpTyrGlnLeuGluLysGluProIleValGlyAlaGluThr         606
BH5   ---------------------------------------------------------------------------

BH10  TTCTATGTAGATGGGGCAGCTAACAGGGAGACTAAATTAGGAAAAGCAGGATATGTTACTAACAAAGGAAGACAA  3521
      PheTyrValAspGlyAlaAlaAsnArgGluThrLysLeuGlyLysAlaGlyTyrValThrAsnLysGlyArgGln         631
BH5   ----------------------G---------------------------------------T-G----------
                            Ser                                          Arg

BH10  AAGGTTGTCCCCCTAACTAACACAACAAATCAGAAAACTGAGTTACAAGCAATTTATCTAGCTTTGCAGGATTCA  3596
      LysValValProLeuThrAsnThrThrAsnGlnLysThrGluLeuGlnAlaIleTyrLeuAlaLeuGlnAspSer         656
BH5   --A------A--------C----------------G-----A-------------C-------------------G
                Thr       His                                    Asn

BH10  GGATTAGAAGTAAACATAGTAACAGACTCACAATATGCATTAGGAATCATTCAAGCACAACCAGATAAAAGTGAA  3671
      GlyLeuGluValAsnIleValThrAspSerGlnTyrAlaLeuGlyIleIleGlnAlaGlnProAspLysSerGlu         681
BH5   -------------T-------------------------------------------------------------
                                                              Kpn I
BH10  TCAGAGTTAGTCAATCAAATAATAGAGCAGTTAATAAAAAAGGAAAAGGTCTATCTGGCATGGGTACCAGCACAC  3746
      SerGluLeuValAsnGlnIleIleGluGlnLeuIleLysLysGluLysValTyrLeuAlaTrpValProAlaHis         706
BH5   ---------------------------------------------------------------------------

BH10  AAAGGAATTGGAGGAAATGAACAAGTAGATAAATTAGTCAGTGCTGGAATCAGGAAAATACTATTTTTAGATGGA  3821
      LysGlyIleGlyGlyAsnGluGlnValAspLysLeuValSerAlaGlyIleArgLysIleLeuPheLeuAspGly         731
BH5   ---------------------------------------------------------------------------
```

FIG. 3 (Continued)

```
BH10  GAGGAGAGCAAGAAATGGAGCCAGTAGATCCTAGACTAGAGCCCTGGAAGCATCCAGGAAGTCAGCCTAAAACTG  5471
BH5   ---------------------------------------------------------------------------

BH10  CTTGTACCAATTGCTATTGTAAAAAGTGTTGCTTTCATTGCCAAGTTTGTTTCATAACAAAAGCCTTAGGCATCT  5546
BH5   -------------C-------------------------------------------------------------
                                          (Sst I)
BH10  CCTATGGCAGGAAGAAGCGGAGACAGCGACGAAGACCTCCTCAAGGCAGTCAGACTCATCAAGTTTCTCTATCAA  5621
BH5   -----------------------------------G---
BH8                                    --G---A--G-A------------------------------

BH10  AGCAGTAAGTAGTACATGTAATGCAACCTATACAAATAGCAATAGTAGCA[ ]TTAGTAGTAGCAATAATAATAGCAA  5696
BH8   ---------------------C-----------C-----T-C-A---T-GCC----C---------------------

BH10  TAGTTGTGTGGTCCATAGTAATCATAGAATATAGGAAAATATTAAGACAAAGAAAAATAGACAGGTTAATTGATA  5771
BH8   ---------------------------------------------------------------------------
                |------- ENV-LOR
BH10  GACTAATAGAAAGAGCAGAAGACAGTGGCAATGAGAGTGAAGGAGAAATATCAGCACTTGTGGAGATGGGGGTGG  5846
               LysGluGlnLysThrValAlaMetArgValLysGluLysTyrGlnHisLeuTrpArgTrpGlyTrp
BH8   ---------------------------------------------------------------------------

BH10  AGATGGGGCACCATGCTCCTTGGGATGTTGATGATCTGTAGTGCTACAGAAAAATTGTGGGTCACAGTCTATTAT  5921
      ArgTrpGlyThrMetLeuLeuGlyMetLeuMetIleCysSerAlaThrGluLysLeuTrpValThrValTyrTyr
BH8   -------------------------------------------------------------------------T-
                                                                            Phe
        Kpn I
BH10  GGGGTACCTGTGTGGAAGGAAGCAACCACCACTCTATTTTGTGCATCAGATGCTAAAGCATATGATACAGAGGTA  5996
      GlyValProValTrpLysGluAlaThrThrThrLeuPheCysAlaSerAspAlaLysAlaTyrAspThrGluVal
BH8   ---------------------------------------------------------------------------
```

```
          ompA signal peptide                    HTLV-III
                                  EcoRI
                                    ▼
ompA3-R-3:  ------- GCGCAGGCC   GGAATTCCCTACAATCCCCAAAGTCAAGGAGTAGTAGAATCTATGAATAAAGAATTA ------
            ------- AlaGlnAla   GlyIleProTyrAsnProGlnSerGlnGlyValValGluSerMETAsnLysGluLeu ------

                                  EcoRI
                                    ▼
OmpA2-R-7:  ------- GCGCAGGCC   GCTGAATTCCCTACAATCCCCAAAGTCAAGGAGTAGTAGAATCTATGAATAAAGAATTA ----
            ------- AlaGlnAla   AlaGluPhe

                                  EcoRI
                                    ▼
OmpA1-R-6:  ------- GCGCAGGCC   GCGAATTCCCTACAATCCCCAAAGTCAAGGAGTAGTAGAATCTATGAATAAAGAATTA ------
            ------- AlaGlnAla   AlaAsnSer
```

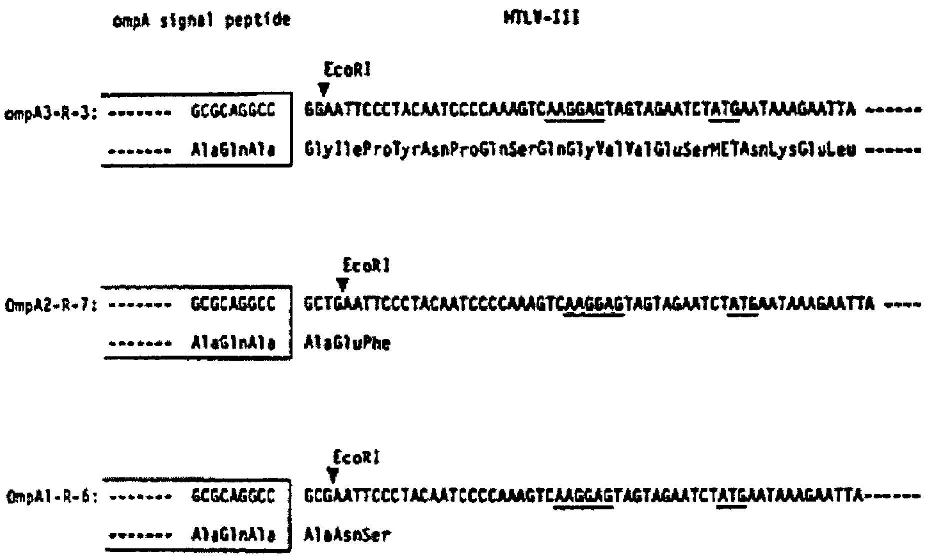

FIG. 6a

SEQUENCE LISTING

```
<160> NUMBER OF SEQ ID NOS: 11

<210> SEQ ID NO 1
<211> LENGTH: 492
<212> TYPE: DNA
<213> ORGANISM: HTLV-III
<220> FEATURE:
<221> NAME/KEY: misc_feature
<223> OTHER INFORMATION: The DNA of this sequence is genomic DNA.
<220> FEATURE:
```

<221> NAME/KEY: misc_feature
<222> LOCATION: (1)..(492)
<223> OTHER INFORMATION: Standard name="Clone BH10"
Corresponds to nucleotide positions -453 to 39 in figure
3 of US 8/080,387

<400> SEQUENCE: 1
tggaagggct aattcactcc caacgaagac aagatatcct tgatctgtgg atctaccaca 60
cacaaggcta cttccctgat tagcagaact acacaccagg gccagggatc agatatccac 120
tgacctttgg atggtgctac aagctagtac cagttgagcc agagaagtta gaagaagcca 180
acaaaggaga gaacaccagc ttgttacacc ctgtgagcct gcatggaatg gatgacccgg 240
agagagaagt gttagagtgg aggtttgaca gccgcctagc atttcatcac atggcccgag 300
agctgcatcc ggagtacttc aagaactgct gacatcgagc ttgctacaag ggactttccg 360
ctggggactt tccagggagg cgtggcctgg gcgggactgg ggagtggcga gccctcagat 420
cctgcatata agcagctgct tttgcctgt actgggtctc tctggttaga ccagatctga 480
gcctgggagc tc 492

<210> SEQ ID NO 2
<211> LENGTH: 492
<212> TYPE: DNA
<213> ORGANISM: HTLV-III
<220> FEATURE:
<221> NAME/KEY: misc_feature
<223> OTHER INFORMATION: The DNA of this sequence is genomic DNA.
<220> FEATURE:
<221> NAME/KEY: misc_feature
<222> LOCATION: (1)..(492)
<223> OTHER INFORMATION: Standard name="Clone BH8".
Corresponds to nucleotide positions -453 to 39 in figure
3 of US 08/080,387.

<400> SEQUENCE: 2
tggaagggct aattcactcc caacgaagac aagatatcct tgatctgtgg atccaccaca 60
cacaaggcta cttccctgat tggcagaact acacaccagg gccaggagtc agatatccac 120
tgacctttgg atggtgctac aagctagtac cagttgagcc agagaagtaa gaagaagcca 180
ataaaggaga gaacaccagc ttgttacacc ctgtgagcct gcatggaatg gatgaccctg 240
agagagaagt gttagagtgg aggtttgaca gccgcctagc atttcatcac atggcccgag 300
agctgcatcc ggagtacttc aagaactgct gatatcgagc ttgctacaag ggactttccg 360
ctggggactt tccagggagg cgtggcctgg gcgggactgg ggagtggcga gccctcagat 420
cctgcatata agcagctgct tttgcctgt actgggtctc tctggttaga ccagatctga 480
gcctgggagc tc 492

<210> SEQ ID NO 3
<211> LENGTH: 182
<212> TYPE: DNA
<213> ORGANISM: HTLV-III
<220> FEATURE:
<221> NAME/KEY: misc_feature
<223> OTHER INFORMATION: The DNA of this sequence is genomic DNA.
<220> FEATURE:
<221> NAME/KEY: misc_feature
<222> LOCATION: (1)..(182)
<223> OTHER INFORMATION: Standard name="Clone HXB2".
Corresponds to nucleotide positions 40 to 221 in figure
3 of US 08/080,387.

<400> SEQUENCE: 3
tctggctaac tagggaaccc actgcttaag cctcaataaa gcttgccttg agtgcttcaa 60
gtagtgtgtg cccgtctgtt gtgtgactct ggtaactaga gatccctcag acccttttag 120
tcagtgtgga aaatctctag cagtggcgcc cgaacaggga cctgaaagcg aaagggaaac 180
ca 182

<210> SEQ ID NO 4
<211> LENGTH: 8933
<212> TYPE: DNA
<213> ORGANISM: HTLV-III
<220> FEATURE:
<221> NAME/KEY: misc_feature
<223> OTHER INFORMATION: The DNA of this sequence is genomic DNA.
<220> FEATURE:
<221> NAME/KEY: misc_feature
<222> LOCATION: (1)..(8933)
<223> OTHER INFORMATION: Standard name="Clone BH10". Corresponds to nucleotide positions 222 to 9154 in figure 3 of EP 85307260.
<220> FEATURE:
<221> NAME/KEY: misc_feature
<222> LOCATION: (113)..(1648)
<223> OTHER INFORMATION: Product = "gag".
<220> FEATURE:
<221> NAME/KEY: misc_feature
<222> LOCATION: (1408)..(4452)
<223> OTHER INFORMATION: Product = "pol".
<220> FEATURE:
<221> NAME/KEY: misc_feature
<222> LOCATION: (4367)..(4975)
<223> OTHER INFORMATION: Product = "sor".
<220> FEATURE:
<221> NAME/KEY: misc_feature
<222> LOCATION: (5560)..(8148)
<223> OTHER INFORMATION: Product = "env".

<400> SEQUENCE: 4
gagctctctc gacgcaggac tcggcttgct gaagcgcgca cggcaagagg cgaggggcgg 60
cgactggtga gtacgccaaa aattttgact agcggaggct agaaggagag agatgggtgc 120
gagagcgtca gtattaagcg ggggagaatt agatcgatgg gaaaaaattc ggttaaggcc 180
agggggaaag aaaaaatata aattaaaaca tatagtatgg gcaagcaggg agctagaacg 240
attcgcagtt aatcctggcc tgttagaaac atcagaaggc tgtagacaaa tactgggaca 300
gctacaacca tcccttcaga caggatcaga agaacttaga tcattatata atacagtagc 360
aaccctctat tgtgtgcatc aaaggataga gataaaagac accaaggaag ctttagacaa 420
gatagaggaa gagcaaaaca aaagtaagaa aaaagcacag caagcagcag ctgacacagg 480
acacagcagt caggtcagcc aaaattaccc tatagtgcag aacatccagg ggcaaatggt 540
acatcaggcc atatcaccta gaactttaaa tgcatgggta aaagtagtag aagagaaggc 600
tttcagccca gaagtaatac ccatgttttc agcattatca gaaggagcca ccccacaaga 660
tttaaacacc atgctaaaca cagtgggggg acatcaagca gccatgcaaa tgttaaaaga 720
gaccatcaat gaggaagctg cagaatggga tagagtacat ccagtgcatg cagggcctat 780
tgcaccaggc cagatgagag aaccaagggg aagtgacata gcaggaacta ctagtaccct 840
tcaggaacaa ataggatgga tgacaaataa tccacctatc ccagtaggag aaatttataa 900
aagatggata atcctgggat taaataaaat agtaagaatg tatagcccta ccagcattct 960
ggacataaga caaggaccaa aagaaccttt tagagactat gtagaccggt tctataaaac 1020
tctaagagcc gagcaagctt cacaggaggt aaaaaattgg atgacagaaa ccttgttggt 1080
ccaaaatgcg aacccagatt gtaagactat tttaaaagca ttgggaccag cggctacact 1140
agaagaaatg atgacagcat gtcagggagt aggaggaccc ggccataagg caagagtttt 1200

-continued

```
ggctgaagca atgagccaag taacaaatac agctaccata atgatgcaga gaggcaattt   1260
taggaaccaa agaaagatgg ttaagtgttt caattgtggc aaagaagggc acacagccag   1320
aaattgcagg gcccctagga aaaagggctg ttggaaatgt ggaaaggaag gacaccaaat   1380
gaaagattgt actgagagac aggctaattt tttagggaag atctggcctt cctacaaggg   1440
aaggccaggg aattttcttc agagcagacc agagccaaca gccccaccat ttcttcagag   1500
cagaccagag ccaacagccc caccagaaga gagcttcagg tctggggtag agacaacaac   1560
tccccctcag aagcaggagc cgatagacaa ggaactgtat cctttaactt ccctcagatc   1620
actctttggc aacgacccct cgtcacaata aagatagggg ggcaactaaa ggaagctcta   1680
ttagatacag gagcagatga tacagtatta gaagaaatga gtttgccagg aagatggaaa   1740
ccaaaaatga tagggggaat tggaggtttt atcaaagtaa gacagtatga tcagatactc   1800
atagaaatct gtggacataa agctataggt acagtattag taggacctac acctgtcaac   1860
ataattggaa gaaatctgtt gactcagatt ggttgcactt taaattttcc cattagccct   1920
attgagactg taccagtaaa attaaagcca ggaatggatg gcccaaaagt taaacaatgg   1980
ccattgacag aagaaaaaat aaaagcatta gtagaaattt gtacagaaat ggaaaaggaa   2040
gggaaaattt caaaaattgg gcctgagaat ccatacaata ctccagtatt tgccataaag   2100
aaaaaagaca gtactaaatg gagaaaatta gtagatttca gagaacttaa taagagaact   2160
caagacttct gggaagttca attaggaata ccacatcccg cagggttaaa aaagaaaaaa   2220
tcagtaacag tactggatgt gggtgatgca tatttttcag ttcccttaga tgaagacttc   2280
aggaagtata ctgcatttac catacctagt ataaacaatg agacaccagg gattagatat   2340
cagtacaatg tgcttccaca gggatggaaa ggatcaccag caatattcca aagtagcatg   2400
acaaaaatct tagagccttt taaaaaacaa aatccagaca tagttatcta tcaatacatg   2460
gatgatttgt atgtaggatc tgacttagaa atagggcagc atagaacaaa aatagaggag   2520
ctgagacaac atctgttgag gtggggactt accacaccag acaaaaaaca tcagaaagaa   2580
cctccattcc tttggatggg ttatgaactc catcctgata aatggacagt acagcctata   2640
gtgctgccag aaaaagacag ctggactgtc aatgacatac agaagttagt ggggaaattg   2700
aattgggcaa gtcagattta cccagggatt aaagtaaggc aattatgtaa actccttaga   2760
ggaaccaaag cactaacaga agtaatacca ctaacagaag aagcagagct agaactggca   2820
gaaaacagag agattctaaa agaaccagta catggagtgt attatgaccc atcaaaagac   2880
ttaatagcag aaatacagaa gcaggggcaa ggccaatgga catatcaaat ttatcaagag   2940
ccatttaaaa atctgaaaac aggaaaatat gcaagaatga ggggtgccca cactaatgat   3000
gtaaaacaat taacagaggc agtgcaaaaa ataaccacag aaagcatagt aatatgggga   3060
aagactccta aatttaaact acccatacaa aaggaaacat gggaaacatg gtggacagag   3120
tattggcaag ccacctggat tcctgagtgg gagtttgtta atacccctcc tttagtgaaa   3180
ttatggtacc agttagagaa agaacccata gtaggagcag aaaccttcta tgtagatggg   3240
gcagctaaca gggagactaa attaggaaaa gcaggatatg ttactaacaa aggaagacaa   3300
aaggttgtcc ccctaactaa cacaacaaat cagaaaactg agttacaagc aatttatcta   3360
gctttgcagg attcaggatt agaagtaaac atagtaacag actcacaata tgcattagga   3420
atcattcaag cacaaccaga taaaagtgaa tcagagttag tcaatcaaat aatagagcag   3480
ttaataaaaa aggaaaaggt ctatctggca tgggtaccag cacacaaagg aattggagga   3540
```

-continued

```
aatgaacaag tagataaatt agtcagtgct ggaatcagga aaatactatt tttagatgga   3600
atagataagg cccaagatga acatgagaaa tatcacagta attggagagc aatggctagt   3660
gattttaacc tgccacctgt agtagcaaaa gaaatagtag ccagctgtga taaatgtcag   3720
ctaaaaggag aagccatgca tggacaagta gactgtagtc caggaatatg gcaactagat   3780
tgtacacatt tagaaggaaa agttatcctg gtagcagttc atgtagccag tggatatata   3840
gaagcagaag ttattccagc agaaacaggg caggaaacag catattttct tttaaaatta   3900
gcaggaagat ggccagtaaa aacaatacat acagacaatg gcagcaattt caccagtgct   3960
acggttaagg ccgcctgttg gtgggcggga atcaagcagg aatttggaat tccctacaat   4020
ccccaaagtc aaggagtagt agaatctatg aataaagaat taaagaaaat tataggacag   4080
gtaagagatc aggctgaaca tcttaagaca gcagtacaaa tggcagtatt catccacaat   4140
tttaaaagaa aaggggggat tggggggtac agtgcagggg aaagaatagt agacataata   4200
gcaacagaca tacaaactaa agaattacaa aaacaaatta caaaaattca aaattttcgg   4260
gtttattaca gggacagcag aaatccactt tggaaaggac cagcaaagct cctctggaaa   4320
ggtgaagggg cagtagtaat acaagataat agtgacataa aagtagtgcc aagaagaaaa   4380
gcaaagatca ttagggatta tggaaaacag atggcaggtg atgattgtgt ggcaagtaga   4440
caggatgagg attagaacat ggaaaagttt agtaaaacac catatgtatg tttcagggaa   4500
agctagggga tggttttata gacatcacta tgaaagccct catccaagaa taagttcaga   4560
agtacacatc ccactagggg atgctagatt ggtaataaca acatattggg gtctgcatac   4620
aggagaaaga gactggcatt tgggtcaggg agtctccata gaatggagga aaaagagata   4680
tagcacacaa gtagaccctg aactagcaga ccaactaatt catctgtatt actttgactg   4740
tttttcagac tctgctataa gaaaggcctt attaggacac atagttagcc ctaggtgtga   4800
atatcaagca ggacataaca aggtaggatc tctacaatac ttggcactag cagcattaat   4860
aacaccaaaa aagataaagc cacctttgcc tagtgttacg aaactgacag aggatagatg   4920
gaacaagccc cagaagacca agggccacag agggagccac acaatgaatg gacactagag   4980
cttttagagg agcttaagaa tgaagctgtt agacattttc ctaggatttg gctccatggc   5040
ttagggcaac atatctatga aacttatggg gatacttggg caggagtgga agccataata   5100
agaattctgc aacaactgct gtttatccat tttcagaatt gggtgtcgac atagcagaat   5160
aggcgttact cgacagagga gagcaagaaa tggagccagt agatcctaga ctagagccct   5220
ggaagcatcc aggaagtcag cctaaaactg cttgtaccaa ttgctattgt aaaaagtgtt   5280
gctttcattg ccaagtttgt ttcataacaa aagccttagg catctcctat ggcaggaaga   5340
agcggagaca gcgacgaaga cctcctcaag gcagtcagac tcatcaagtt tctctatcaa   5400
agcagtaagt agtacatgta atgcaaccta tacaaatagc aatagtagca ttagtagtag   5460
caataataat agcaatagtt gtgtggtcca tagtaatcat agaatatagg aaaatattaa   5520
gacaaagaaa aatagacagg ttaattgata gactaataga aagagcagaa gacagtggca   5580
atgagagtga aggagaaata tcagcacttg tggagatggg ggtggagatg gggcaccatg   5640
ctccttggga tgttgatgat ctgtagtgct acagaaaaat tgtgggtcac agtctattat   5700
ggggtacctg tgtggaagga agcaaccacc actctatttt gtgcatcaga tgctaaagca   5760
tatgatacag aggtacataa tgtttgggcc acacatgcct gtgtacccac agaccccaac   5820
ccacaagaag tagtattggt aaatgtgaca gaaaatttta acatgtggaa aaatgacatg   5880
gtagaacaga tgcatgagga tataatcagt ttatgggatc aaagcctaaa gccatgtgta   5940
```

-continued

```
aaattaaccc cactctgtgt tagtttaaag tgcactgatt tgaagaatga tactaatacc   6000
aatagtagta gcgggagaat gataatggag aaaggagaga taaaaaactg ctctttcaat   6060
atcagcacaa gcataagagg taaggtgcag aaagaatatg cattttttta taaacttgat   6120
ataataccaa tagataatga tactaccagc tatacgttga caagttgtaa cacctcagtc   6180
attacacagg cctgtccaaa ggtatccttt gagccaattc ccatacatta ttgtgccccg   6240
gctggttttg cgattctaaa atgtaataat aagacgttca atggaacagg accatgtaca   6300
aatgtcagca cagtacaatg tacacatgga attaggccag tagtatcaac tcaactgctg   6360
ttaaatggca gtctggcaga agaagaggta gtaattagat ctgccaattt cacagacaat   6420
gctaaaacca taatagtaca gctgaaccaa tctgtagaaa ttaattgtac aagacccaac   6480
aacaatacaa gaaaaagtat ccgtatccag agaggaccag ggagagcatt tgttacaata   6540
ggaaaaatag gaaatatgag acaagcacat tgtaacatta gtagagcaaa atggaataac   6600
actttaaaac agatagatag caaattaaga gaacaatttg gaaataataa aacaataatc   6660
tttaagcagt cctcaggagg ggacccagaa attgtaacgc acagttttaa ttgtggaggg   6720
gaatttttct actgtaattc aacacaactg tttaatagta cttggtttaa tagtacttgg   6780
agtactaaag ggtcaaataa cactgaagga agtgacacaa tcaccctccc atgcagaata   6840
aaacaaatta taaacatgtg gcaggaagta ggaaaagcaa tgtatgcccc tcccatcagt   6900
ggacaaatta gatgttcatc aaatattaca gggctgctat taacaagaga tggtggtaat   6960
agcaacaatg agtccgagat cttcagacct ggaggaggag atatgaggga caattggaga   7020
agtgaattat ataaatataa agtagtaaaa attgaaccat taggagtagc acccaccaag   7080
gcaaagagaa gagtggtgca gagagaaaaa agagcagtgg gaataggagc tttgttcctt   7140
gggttcttgg gagcagcagg aagcactatg ggcgcagcgt caatgacgct gacggtacag   7200
gccagacaat tattgtctgg tatagtgcag cagcagaaca atttgctgag ggctattgag   7260
gcgcaacagc atctgttgca actcacagtc tggggcatca agcagctcca ggcaagaatc   7320
ctggctgtgg aaagatacct aaaggatcaa cagctcctgg ggatttgggg ttgctctgga   7380
aaactcattt gcaccactgc tgtgccttgg aatgctagtt ggagtaataa atctctggaa   7440
cagatttgga ataacatgac ctggatggag tgggacagag aaattaacaa ttacacaagc   7500
ttaatacact ccttaattga agaatcgcaa aaccagcaag aaaagaatga acaagaatta   7560
ttggaattag ataaatgggc aagtttgtgg aattggttta acataacaaa ttggctgtgg   7620
tatataaaat tattcataat gatagtagga ggcttggtag gtttaagaat agtttttgct   7680
gtactttctg tagtgaatag agttaggcag ggatattcac cattatcgtt tcagacccac   7740
ctcccaatcc cgaggggacc cgacaggccc gaaggaatag aagaagaagg tggagagaga   7800
gacagagaca gatccattcg attagtgaac ggatccttag cacttatctg ggacgatctg   7860
cggagcctgt gcctcttcag ctaccaccgc ttgagagact tactcttgat tgtaacgagg   7920
attgtggaac ttctgggacg cagggggtgg gaagccctca aatattggtg gaatctccta   7980
cagtattgga gtcaggagct aaagaatagt gctgttagct tgctcaatgc cacagctata   8040
gcagtagctg aggggacaga tagggttata gaagtagtac aaggagctta tagagctatt   8100
cgccacatac ctagaagaat aagacagggc ttggaaagga ttttgctata agatgggtgg   8160
caagtggtca aaaagtagtg tggttggatg gcctgctgta agggaaagaa tgagacgagc   8220
tgagccagca gcagatgggg tgggagcagc atctcgagac ctagaaaaac atggagcaat   8280
```

-continued

```
cacaagtagc aacacagcag ctaacaatgc tgattgtgcc tggctagaag cacaagagga   8340

ggaggaggtg ggttttccag tcacacctca ggtaccttta agaccaatga cttacaaggc   8400

agctgtagat cttagccact ttttaaaaga aaagggggga ctggaagggc taattcactc   8460

ccaacgaaga caagatatcc ttgatctgtg gatctaccac acacaaggct acttccctga   8520

ttagcagaac tacacaccag ggccagggat cagatatcca ctgacctttg gatggtgcta   8580

caagctagta ccagttgagc cagagaagtt agaagaagcc aacaaaggag agaacaccag   8640

cttgttacac cctgtgagcc tgcatggaat ggatgacccg gagagagaag tgttagagtg   8700

gaggtttgac agccgcctag catttcatca catggcccga gagctgcatc cggagtactt   8760

caagaactgc tgacatcgag cttgctacaa gggactttcc gctggggact ttccagggag   8820

gcgtggcctg ggcgggactg gggagtggcg agccctcaga tcctgcatat aagcagctgc   8880

tttttgcctg tactgggtct ctctggttag accagatctg agcctgggag ctc          8933
```

```
<210> SEQ ID NO 5
<211> LENGTH: 5362
<212> TYPE: DNA
<213> ORGANISM: HTLV-III
<220> FEATURE:
<221> NAME/KEY: misc_feature
<223> OTHER INFORMATION: The DNA of this sequence is genomic DNA.
<220> FEATURE:
<221> NAME/KEY: misc_feature
<222> LOCATION: (1)..(5362)
<223> OTHER INFORMATION: Standard name="Clone BH5".
      Corresponds to nucleotide positions 222 to 5585 in
      figure 3 of US 08/080,387.

<400> SEQUENCE: 5
```

```
gagctctctc gacgcaggac tcggcttgcg agcgcgcacg gcaagaggcg aggggcggcg     60

actggtgagt acgccaaaaa ttttgactag cggaggctag aaggagagag atgggtgcga    120

gagcgtcagt attaagcggg ggagaattag atcgatggga aaaaattcgg ttaaggccag    180

ggggaaagaa aaaatataaa ttaaaacata tagtatgggc aagcagggag ctagaacgat    240

tcgcagttaa tcctggcctg ttagaaacat cagaaggctg tagacaaata ctgggacagc    300

tacaaccatc ccttcagaca ggatcagaag aacttagatc attatataat acagtagcaa    360

ccctctattg tgtgcatcaa aggatagaga taaaagacac caaggaagct ttagacaaga    420

tagaggaaga gcaaaacaaa agtaagaaaa aagcacagca agcagcagct gacacaggac    480

acagcagtca ggtcagccaa aattacccta tagtgcagaa catccagggg caaatggtac    540

atcaggccat atcacctaga actttaaatg catgggtaaa agtagtagaa gagaaggctt    600

tcagcccaga agtgataccc atgttttcag cattatcaga aggagccacc ccacaagatt    660

taaacaccat gctaaacaca gtggggggac atcaagcagc catgcaaatg ttaaaagaga    720

ccatcaatga ggaagctgca gaatgggata gagtgcatcc agtgcatgca gggcctatcg    780

caccaggcca gatgagagaa ccaaggggaa gtgacatagc aggaactact agtacccttc    840

aggaacaaat aggatggatg acaaataatc cacctatccc agtaggagaa atttataaaa    900

gatggataat cctgggatta aataaaatag taaggatgta tagtcctacc agcattctgg    960

acataagaca aggaccaaag gaacccttta gagactatgt agaccggttc tataaaactc   1020

taagagccga gcaagcttca caggaagtaa aaaattggat gacagaaacc ttgttggtcc   1080

aaaatgcgaa cccagattgt aagactattt taaaagcatt gggaccagcg gctacactag   1140

aagaaatgat gacagcatgt cagggagtag gaggacccgg ccataaggca agagttttgg   1200
```

-continued

```
ctgaagcaat gagccaagta acaaattcaa ctaccataat gatgcaaaga ggcaatttta   1260
ggaaccaaag aaaaattgtt aagtgtttca attgtggcaa agaagggcac atagcaagaa   1320
attgcaaggc ccctagaaaa aagggctgtt ggaaatgtgg aaaggaagga caccaaatga   1380
aagattgtac tgagagacag gctaattttt tagggaagat ctggccttcc tacaagggaa   1440
ggccagggaa ttttcttcag agcagaccag agccaacagc cccaccattt cttcagagca   1500
gaccagagcc aacagcccca ccagaagaga gcttcaggtc tggggtagag acaacaactc   1560
cccctcagaa gcaggagccg atagacaagg aactgtatcc tttaacttcc ctcagatcac   1620
tctttggcaa cgacccctcg tcacaataaa gatagggggg caactaaagg aagctctatt   1680
agatacagga gcagatgata cagtattaga agaaatgagt ttgccaggaa gatggaaacc   1740
aaaaatgata gggggaattg gaggttttat caaagtaaga cagtatgatc agatactcat   1800
agaaatctgt ggacataaag ctataggtac agtattagta ggacctacac ctgtcaacat   1860
aattggaaga aatctgttga ctcagattgg ttgcacttta aattttccca ttagtcctat   1920
tgaaactgta ccagtaaaat taaagccagg aatggatggc ccaaaagtta aacaatggcc   1980
attgacagaa gaaaaaataa aagcattagt agaaatttgt acagaaatgg aaaaggaagg   2040
gaaaatttca aaaattgggc ctgaaaatcc atacaatact ccagtatttg ccataaagaa   2100
aaaagacagt actaaatgga gaaaattagt agatttcaga gaacttaata ggagaactca   2160
agacttctgg gaagttcaat tgggaatacc acatcccgca gggttaaaaa agaaaaaatc   2220
agtaacagta ctggatgtgg gtgatgcata tttttcagtt cccttagatg aagacttcag   2280
gaagtatact gcatttacca tacctagtat aaataatgag acaccaggga gtggatatca   2340
gtacaatgtg cttccacagg gatggaaagg atcaccagca atattccaaa gtagcatgac   2400
aaaaatctta gagcctttta gaaaacaaaa tccagacata gttatttatc aatacatgga   2460
tgatttgtat gtaggatctg acttagaaat agggcagcat agaacaaaaa tagaggagct   2520
gagacaacat ctgttgaggt ggggatttac cacaccagac aaaaaacatc agaaagaacc   2580
tccattcctt tggatgggtt atgaactcca tcctgataaa tggacgatac agcctatagt   2640
gctgccagaa aaagacagct ggactgtcaa tgacatacag aagttagtgg gaaaattgaa   2700
ttgggcaagt cagatttatc cagggattaa agtaaggcaa ttatgtaaac tccttagagg   2760
aaccaaagca ctaacagaag taataccact aacagaagaa gcagagctag aactggcaga   2820
aaacagagag attctaaaag aaccagtaca tggagtgtat tatgacccat caaaagactt   2880
aatagcagaa atacagaagc aggggcaagg ccaatggaca tatcaaattt atcaagagcc   2940
atttaaaaat ctgaaaacag gaaaatatgc aagaatgagg ggtgcccaca ctaatgatgt   3000
aaaacaatta acagaggcag tgcaaaaaat aaccacagaa agcatagtaa tatggggaaa   3060
gactcctaaa tttaaactac ccatacaaaa agaaacatgg gaaacatggt ggacagagta   3120
ttggcaagcc acctggattc ctgagtggga gtttgttaat acccctcctt tagtgaaatt   3180
atggtaccag ttagagaaag aacccatagt aggagcagaa accttctatg tagatggggc   3240
agctagcagg gagactaaat taggaaaagc aggatatgtt actaatagag gaagacaaaa   3300
agttgtcacc ctaactcaca caacaaatca gaagactgaa ttacaagcaa ttcatctagc   3360
tttgcaggat tcgggattag aagtaaatat agtaacagac tcacaatatg cattaggaat   3420
cattcaagca caaccagata aaagtgaatc agagttagtc aatcaaataa tagagcagtt   3480
aataaaaaag gaaaaggtct atctggcatg ggtaccagca cacaaaggaa ttggaggaaa   3540
tgaacaagta gataaattag tcagtgctgg aatcaggaaa atactatttt tagatggaat   3600
```

```
agataaggcc caagaagaac atgagaaata tcacagtaat tggagagcaa tggctagtga   3660
ttttaacctg ccacctgtag tagcaaaaga aatagtagcc agctgtgata aatgtcagct   3720
aaaaggagaa gccatgcatg gacaagtaga ctgtagtcca ggaatatggc aactagattg   3780
tacacattta gaaggaaaag ttatcctggt agcagttcat gtagccagtg gatatataga   3840
agcagaagtt attccagcag aaacagggca ggaaacagca tattttcttt taaaattagc   3900
aggaagatgg ccagtaaaaa caatacatac agacaatggc agcaatttca ccagtgctac   3960
ggttaaggcc gcctgttggt gggcgggaat caagcaggaa tttggaattc cctacaatcc   4020
ccaaagtcaa ggagtagtag aatctatgaa taaagaatta aagaaaatta taggacaggt   4080
aagagatcag gctgaacatc ttaagacagc agtacaaatg gcagtattca tccacaattt   4140
taaaagaaaa ggggggattg gggggtacag tgcaggggaa agaatagtag acataatagc   4200
aacagacata caaactaaag aattacaaaa acaaattaca aaaattcaaa attttcgggt   4260
ttattacagg gacagcagaa atccactttg gaaaggacca gcaaagctcc tctggaaagg   4320
tgaaggggca gtagtaatac aagataatag tgacataaaa gtagtgccaa gaagaaaagc   4380
aaagatcatt agggattatg gaaaacagat ggcaggtgat gattgtgtgg caagtagaca   4440
ggatgaggat tagaacatgg aaaagtttag taaaacaccg tatgtatgtt tcagggaaag   4500
ctaggggatg gttttataga catcactatg aaagccctca tccaagaata agttcagaag   4560
tacacatccc actaggggat gctagattgg taataacaac atattggggt ctgcatacag   4620
gagaaagaga ctggcatttg ggtcagggag tctccataga atggaggaaa aggagatata   4680
gcacacaagt agaccctgaa ctagcagacc aactaattca tctgcattac tttgattgtt   4740
tttcagactc tgctataaga aaggccttat taggacacat agttagccct aggtgtgaat   4800
atcaagcagg acataacaag gtaggatctc tacaatactt ggcactagca gcattaataa   4860
caccaaaaaa ggtaaagcca cctttgccta gtgttacgaa actgacagag gatagatgga   4920
acaagcccca gaagaccaag ggccacagag gaagccacac aatgaatgga cactagagct   4980
tttagaggag cttaagaatg aagctgttag acattttcct aggatttggc tccatggctt   5040
agggcaacat atctatgaaa cttatgggga tacttgggca ggagtggaag ccataataag   5100
aattctgcaa caactgctgt ttatccattt tcagaattgg gtgtcgacat agcagaatag   5160
gcgttactca acagaggaga gcaagaaatg gagccagtag atcctagact agagccctgg   5220
aagcatccag gaagtcagcc taaaactgct tgtaccactt gctattgtaa aaagtgttgc   5280
tttcattgcc aagtttgttt cataacaaaa gccttaggca tctcctatgg caggaagaag   5340
cggagacagc gacgaagagc tc                                            5362
```

<210> SEQ ID NO 6
<211> LENGTH: 3563
<212> TYPE: DNA
<213> ORGANISM: HTLV-III
<220> FEATURE:
<221> NAME/KEY: misc_feature
<223> OTHER INFORMATION: The DNA of this sequence is genomic DNA.
<220> FEATURE:
<221> NAME/KEY: misc_feature
<222> LOCATION: (1)..(3563)
<223> OTHER INFORMATION: Standard name="Clone BH8". Corresponds to nucleotide positions 5580 to 9154 in figure 3 of US 08/080,387.

<400> SEQUENCE: 6

```
gagctcatcg aagcagtcag actcatcaag tttctctatc aaagcagtaa gtagtacatg     60
```

-continued

```
taacgcaacc tataccaata gtaacaatag tagccttagc agtagcaata ataatagcaa    120
tagttgtgtg gtccatagta atcatagaat ataggaaaat attaagacaa agaaaaatag    180
acaggttaat tgatagacta atagaaagag cagaagacag tggcaatgag agtgaaggag    240
aaatatcagc acttgtggag atgggggtgg agatggggca ccatgctcct tgggatgttg    300
atgatctgta gtgctacaga aaaattgtgg gtcacagtct attttggggt acctgtgtgg    360
aaggaagcaa ccaccactct attttgtgca tcagatgcta aagcatatga tacagaggta    420
cataatgttt gggccacaca tgcctgtgta cccacagacc ccaacccaca agaagtagta    480
ttggtaaatg tgacagaaaa ttttaacatg tggaaaaatg acatggtaga acagatgcat    540
gaggatataa tcagtttatg ggatcaaagc ctaaagccat gtgtaaaatt aaccccactc    600
tgtgttagtt taaagtgcac tgatttgaag aatgatacta ataccaatag tagtagcggg    660
agaatgataa tggagaaagg agagataaaa aactgctctt tcaatatcag cacaagcaaa    720
agaggtaagg tgcagaaaga atatgcattt ttttataaac ttgatataat accaatagat    780
aatgatacta ccagctatac gttgacaagt tgtaacacct cagtcattac acaggcctgt    840
ccaaaggtat cctttgagcc aattcccata cattattgtg ccccggctgg ttttgcgatt    900
ctaaaatgta ataataagac gttcaatgga acaggaccat gtacaaatgt cagcacagta    960
caatgtacac atggaattag gccagtagta tcaactcaac tgctgttaaa tggcagtctg   1020
gcagaagaag aggtagtaat tagatctgtc aatttcacgg acaatgctaa aaccataata   1080
gtacagctgg acacatctgt agaaattaat tgtacaagac ccaacaacaa tacaagaaaa   1140
aaaatccgta tccagagggg accagggaga gcatttgtta caataggaaa aataggaaat   1200
atgagacaag cacattgtaa cattagtaga gcaaaatgga atgccacttt aaaacagata   1260
gatagcaaat taagagaaca atttggaaat aataaaacaa taatctttaa gcagtcctca   1320
ggaggggacc cagaaattgt aacgcacagt tttaattgtg gaggggaatt tttctactgt   1380
aattcaacac aactgtttaa tagtacttgg agtactaaag ggtcaaataa cactgaagga   1440
agtgacacaa tcaccctccc atgcagaata aaacaaatta taaacatgtg gcaggaagta   1500
ggaaaagcaa tgtatgcccc tcccatcagt ggacaaatta gatgttcatc aaatattaca   1560
gggctgctat taacaagaga tggtggtaat agcaacaatg agtccgagat cttcagacct   1620
ggaggaggag atatgaggga caattggaga agtgaattat ataaatataa agtagtaaaa   1680
attgaaccat taggagtagc acccaccaag gcaaagagaa gagtggtgca gagagaaaaa   1740
agagcagtgg gaataggagc tttgttcctt gggttcttgg gagcagcagg aagcactatg   1800
ggcgcagcgt caatgacgct gacggtacag gccagacaat tattgtctgg tatagtgcag   1860
cagcagaaca atttgctgag ggctattgag ggccaacagc atctgttgca actcacagtc   1920
tggggcatca agcagctcca ggcaagaatc ctggctgtgg aaagatacct aaaggatcaa   1980
cagctcctgg ggatttgggg ttgctctgga aaactcattt gcaccactgc tgtgccttgg   2040
aatgctagtt ggagtaataa atctctggaa cagatttgga ataacatgac ctggatggag   2100
tgggacagag aaattaacaa ttacacaagc ttaatacact ccttaattga agaatcgcaa   2160
aaccagcaag aaaagaatga acaagaatta ttggaattag ataaatgggc aagtttgtgg   2220
aattggttta acataacaaa ttggctgtgg tatataaaat tattcataat gatagtagga   2280
ggcttggtag gtttaagaat agtttttgct gtactttcta tagtgaatag agttaggcag   2340
ggatattcac cattatcgtt tcagacccac ctcccaaacc cgaggggacc cgacaggccc   2400
```

-continued

```
gaaggaatag aagaagaagg tggagagaga gacagagaca gatccattcg attagtgaac   2460

ggatccttag cacttatctg ggacgatctg cggagcctgt gcctcttcag ctaccaccgc   2520

ttgagagact tactcttgat tgtaacgagg attgtggaac ttctgggacg cagggggtgg   2580

gaagccctca aatattggtg gaatctccta cagtattgga gtcaggaact aaagaatagt   2640

gctgttaact tgctcaatgc cacagctata gcagtagctg aggggacaga tagggttata   2700

gaattagtac aagcagctta tagagccatt cgccacatac ctagaagaat aagacagggc   2760

ttggaaagga ttttgctata agatgggtgg caagtggtca aaaagtagtg tggttggatg   2820

gcctgctgta agggaaagaa tgagacgagc tgagccagca gcagatgggg tgggagcagt   2880

atctcgagac ctagaaaaac atggagcaat cacaagtagc aatacagcag ctaccaatgc   2940

cgattgtgct tggctagaag cacaagagga ggaggaggtg ggttttccag tcacacctca   3000

ggtaccttta agaccaatga cttacaaggc agctgtagat cttagccact ttttaaaaga   3060

aaagggggga ctggaagggc taattcactc ccaacgaaga caagatatcc ttgatctgtg   3120

gatccaccac acacaaggct acttccctga ttggcagaac tacacaccag ggccaggagt   3180

cagatatcca ctgacctttg gatggtgcta caagctagta ccagttgagc cagagaagta   3240

agaagaagcc aataaaggag agaacaccag cttgttacac cctgtgagcc tgcatggaat   3300

ggatgaccct gagagagaag tgttagagtg gaggtttgac agccgcctag catttcatca   3360

catggcccga gagctgcatc cggagtactt caagaactgc tgatatcgag cttgctacaa   3420

gggactttcc gctggggact ttccagggag gcgtggcctg ggcgggactg gggagtggcg   3480

agccctcaga tcctgcatat aagcagctgc tttttgcctg tactgggtct ctctggttag   3540

accagatctg agcctgggag ctc                                           3563
```

```
<210> SEQ ID NO 7
<211> LENGTH: 142
<212> TYPE: DNA
<213> ORGANISM: HTLV-III
<220> FEATURE:
<221> NAME/KEY: misc_feature
<223> OTHER INFORMATION: The DNA of this sequence is genomic DNA.
<220> FEATURE:
<221> NAME/KEY: misc_feature
<222> LOCATION: (1)..(142)
<223> OTHER INFORMATION: Standard name="Clone HXB2".
      Corresponds to nucleotide positions 9155 to 9296 in
      figure 3 of US 08/080,387.

<400> SEQUENCE: 7

tctggctagc tagggaaccc actgcttaag cctcaataaa gcttgccttg agtgcttcaa     60

gtagtgtgtg cccgtctgtt gtgtgactct ggtaactaga gatccctcag acccttttag    120

tcagtgtgga aaatctctag ca                                            142


<210> SEQ ID NO 8
<211> LENGTH: 512
<212> TYPE: PRT
<213> ORGANISM: HTLV-III
<220> FEATURE:
<221> NAME/KEY: MISC_FEATURE
<222> LOCATION: (1)..(512)
<223> OTHER INFORMATION: gag protein of HTLV-III

<400> SEQUENCE: 8

Met Gly Ala Arg Ala Ser Val Leu Ser Tyr Tyr Glu Leu Asp Arg Trp
1               5                   10                  15

Glu Lys Ile Arg Leu Arg Pro Gly Gly Lys Lys Lys Tyr Lys Leu Lys
```

-continued

```
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Leu Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Asp Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Thr Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Tyr Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Tyr Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Thr Ala Thr Ile Met Met Gln Arg Gly Asn Phe Arg
    370                 375                 380

Asn Gln Arg Lys Met Val Lys Cys Phe Asn Cys Gly Lys Glu Gly His
385                 390                 395                 400

Thr Ala Arg Asn Cys Arg Ala Pro Arg Lys Lys Gly Cys Tyr Lys Cys
                405                 410                 415

Gly Lys Glu Gly His Gln Met Lys Asp Cys Thr Glu Arg Gln Ala Asn
            420                 425                 430

Phe Leu Gly Lys Ile Tyr Pro Ser Tyr Lys Gly Arg Pro Gly Asn Phe
        435                 440                 445
```

```
Leu Gln Ser Arg Pro Glu Pro Thr Ala Pro Pro Phe Leu Gln Ser Arg
    450                 455                 460

Pro Glu Pro Thr Ala Pro Pro Glu Glu Ser Phe Arg Ser Gly Val Glu
465                 470                 475                 480

Thr Thr Thr Pro Pro Gln Lys Gln Glu Pro Ile Asp Lys Glu Leu Tyr
                485                 490                 495

Pro Leu Thr Ser Leu Arg Ser Leu Phe Gly Asn Asp Pro Ser Ser Gln
            500                 505                 510


<210> SEQ ID NO 9
<211> LENGTH: 1015
<212> TYPE: PRT
<213> ORGANISM: HTLV-III
<220> FEATURE:
<221> NAME/KEY: MISC_FEATURE
<222> LOCATION: (1)..(1015)
<223> OTHER INFORMATION: pol protein of HTLV-III

<400> SEQUENCE: 9

Phe Phe Arg Glu Asp Leu Ala Phe Leu Gln Gly Lys Ala Arg Glu Phe
1               5                   10                  15

Ser Ser Glu Gln Thr Arg Ala Asn Ser Pro Thr Ile Ser Ser Glu Gln
            20                  25                  30

Thr Arg Ala Asn Ser Pro Thr Arg Arg Glu Leu Gln Val Trp Gly Arg
        35                  40                  45

Asp Asn Asn Ser Pro Ser Glu Ala Gly Ala Asp Arg Gln Gly Thr Val
    50                  55                  60

Ser Phe Asn Phe Pro Gln Ile Thr Leu Trp Gln Arg Pro Leu Val Thr
65                  70                  75                  80

Ile Lys Ile Gly Gly Gln Leu Lys Glu Ala Leu Leu Asp Thr Gly Ala
                85                  90                  95

Asp Asp Thr Val Leu Glu Glu Met Ser Leu Pro Gly Arg Trp Lys Pro
            100                 105                 110

Lys Met Ile Gly Gly Ile Gly Gly Phe Ile Lys Val Arg Gln Tyr Asp
        115                 120                 125

Gln Ile Leu Ile Glu Ile Cys Gly His Lys Ala Ile Gly Thr Val Leu
    130                 135                 140

Val Gly Pro Thr Pro Val Asn Ile Ile Gly Arg Asn Leu Leu Thr Gln
145                 150                 155                 160

Ile Gly Cys Thr Leu Asn Phe Pro Ile Ser Pro Ile Glu Thr Val Pro
                165                 170                 175

Val Lys Leu Lys Pro Gly Met Asp Gly Pro Lys Val Lys Gln Trp Pro
            180                 185                 190

Leu Thr Glu Glu Lys Ile Lys Ala Leu Val Glu Ile Cys Thr Glu Met
        195                 200                 205

Glu Lys Glu Gly Lys Ile Ser Lys Ile Gly Pro Glu Asn Pro Tyr Asn
    210                 215                 220

Thr Pro Val Phe Ala Ile Lys Lys Lys Asp Ser Thr Lys Trp Arg Lys
225                 230                 235                 240

Leu Val Asp Phe Arg Glu Leu Asn Lys Arg Thr Gln Asp Phe Trp Glu
                245                 250                 255

Val Gln Leu Gly Ile Pro His Pro Ala Gly Leu Lys Lys Lys Lys Ser
            260                 265                 270

Val Thr Val Leu Asp Val Gly Asp Ala Tyr Phe Ser Val Pro Leu Asp
        275                 280                 285
```

```
Glu Asp Phe Arg Lys Tyr Thr Ala Phe Thr Ile Pro Ser Ile Asn Asn
    290                 295                 300

Glu Thr Pro Gly Ile Arg Tyr Gln Tyr Asn Val Leu Pro Gln Gly Trp
305                 310                 315                 320

Lys Gly Ser Pro Ala Ile Phe Gln Ser Ser Met Thr Lys Ile Leu Glu
                325                 330                 335

Pro Phe Lys Lys Gln Asn Pro Asp Ile Val Ile Tyr Gln Tyr Met Asp
            340                 345                 350

Asp Leu Tyr Val Gly Ser Asp Leu Glu Ile Gly Gln His Arg Thr Lys
        355                 360                 365

Ile Glu Glu Leu Arg Gln His Leu Leu Arg Trp Gly Leu Thr Thr Pro
    370                 375                 380

Asp Lys Lys His Gln Lys Glu Pro Pro Phe Leu Trp Met Gly Tyr Glu
385                 390                 395                 400

Leu His Pro Asp Lys Trp Thr Val Gln Pro Ile Val Leu Pro Glu Lys
                405                 410                 415

Asp Ser Trp Thr Val Asn Asp Ile Gln Lys Leu Val Gly Lys Leu Asn
            420                 425                 430

Trp Ala Ser Gln Ile Tyr Pro Gly Ile Lys Val Arg Gln Leu Cys Lys
        435                 440                 445

Leu Leu Arg Gly Thr Lys Ala Leu Thr Glu Val Ile Pro Leu Thr Glu
    450                 455                 460

Glu Ala Glu Leu Glu Leu Ala Glu Asn Arg Glu Ile Leu Lys Glu Pro
465                 470                 475                 480

Val His Gly Val Tyr Tyr Asp Pro Ser Lys Asp Leu Ile Ala Glu Ile
                485                 490                 495

Gln Lys Gln Gly Gln Gly Gln Trp Thr Tyr Gln Ile Tyr Gln Glu Pro
            500                 505                 510

Phe Lys Asn Leu Lys Thr Gly Lys Tyr Ala Arg Met Arg Gly Ala His
        515                 520                 525

Thr Asn Asp Val Lys Gln Leu Thr Glu Ala Val Gln Lys Ile Thr Thr
    530                 535                 540

Glu Ser Ile Val Ile Trp Gly Lys Thr Pro Lys Phe Lys Leu Pro Ile
545                 550                 555                 560

Gln Lys Glu Thr Trp Glu Thr Trp Trp Thr Glu Tyr Trp Gln Ala Thr
                565                 570                 575

Trp Ile Pro Glu Trp Glu Phe Val Asn Thr Pro Pro Leu Val Lys Leu
            580                 585                 590

Trp Tyr Gln Leu Glu Lys Glu Pro Ile Val Gly Ala Glu Thr Phe Tyr
        595                 600                 605

Val Asp Gly Ala Ala Asn Arg Glu Thr Lys Leu Gly Lys Ala Gly Tyr
    610                 615                 620

Val Thr Asn Lys Gly Arg Gln Lys Val Val Pro Leu Thr Asn Thr Thr
625                 630                 635                 640

Asn Gln Lys Thr Glu Leu Gln Ala Ile Tyr Leu Ala Leu Gln Asp Ser
                645                 650                 655

Gly Leu Glu Val Asn Ile Val Thr Asp Ser Gln Tyr Ala Leu Gly Ile
            660                 665                 670

Ile Gln Ala Gln Pro Asp Lys Ser Glu Ser Glu Leu Val Asn Gln Ile
        675                 680                 685

Ile Glu Gln Leu Ile Lys Lys Glu Lys Val Tyr Leu Ala Trp Val Pro
    690                 695                 700

Ala His Lys Gly Ile Gly Gly Asn Glu Gln Val Asp Lys Leu Val Ser
```

-continued

```
705                 710                 715                 720

Ala Gly Ile Arg Lys Ile Leu Phe Leu Asp Gly Ile Asp Lys Ala Gln
                725                 730                 735

Asp Glu His Glu Lys Tyr His Ser Asn Trp Arg Ala Met Ala Ser Asp
            740                 745                 750

Phe Asn Leu Pro Pro Val Val Ala Lys Glu Ile Val Ala Ser Cys Asp
        755                 760                 765

Lys Cys Gln Leu Lys Gly Glu Ala Met His Gly Gln Val Asp Cys Ser
    770                 775                 780

Pro Gly Ile Trp Gln Leu Asp Cys Thr His Leu Glu Gly Lys Val Ile
785                 790                 795                 800

Leu Val Ala Val His Val Ala Ser Gly Tyr Ile Glu Ala Glu Val Ile
                805                 810                 815

Pro Ala Glu Thr Gly Gln Glu Thr Ala Tyr Phe Leu Leu Lys Leu Ala
            820                 825                 830

Gly Arg Trp Pro Val Lys Thr Ile His Thr Asp Asn Gly Ser Asn Phe
        835                 840                 845

Thr Ser Ala Thr Val Lys Ala Ala Cys Trp Trp Ala Gly Ile Lys Gln
    850                 855                 860

Glu Phe Gly Ile Pro Tyr Asn Pro Gln Ser Gln Gly Val Val Glu Ser
865                 870                 875                 880

Met Asn Lys Glu Leu Lys Lys Ile Ile Gly Gln Val Arg Asp Gln Ala
                885                 890                 895

Glu His Leu Lys Thr Ala Val Gln Met Ala Val Phe Ile His Asn Phe
            900                 905                 910

Lys Arg Lys Gly Gly Ile Gly Gly Tyr Ser Ala Gly Glu Arg Ile Val
        915                 920                 925

Asp Ile Ile Ala Thr Asp Ile Gln Thr Lys Glu Leu Gln Lys Gln Ile
    930                 935                 940

Thr Lys Ile Gln Asn Phe Arg Val Tyr Tyr Arg Asp Ser Arg Asn Pro
945                 950                 955                 960

Leu Trp Lys Gly Pro Ala Lys Leu Leu Trp Lys Gly Glu Gly Ala Val
                965                 970                 975

Val Ile Gln Asp Asn Ser Asp Ile Lys Val Val Pro Arg Arg Lys Ala
            980                 985                 990

Lys Ile Ile Arg Asp Tyr Gly Lys  Gln Met Ala Gly Asp  Asp Cys Val
        995                 1000                1005

Ala Ser  Arg Gln Asp Glu Asp
    1010                1015


<210> SEQ ID NO 10
<211> LENGTH: 203
<212> TYPE: PRT
<213> ORGANISM: HTLV-III
<220> FEATURE:
<221> NAME/KEY: MISC_FEATURE
<222> LOCATION: (1)..(203)
<223> OTHER INFORMATION: sor protein of HTLV-III

<400> SEQUENCE: 10

Cys Gln Glu Glu Lys Gln Arg Ser Leu Gly Ile Met Glu Asn Arg Trp
1               5                   10                  15

Gln Val Met Ile Val Trp Gln Val Asp Arg Met Arg Ile Arg Thr Trp
            20                  25                  30

Lys Ser Leu Val Lys His His Met Tyr Val Ser Gly Lys Ala Arg Gly
        35                  40                  45
```

```
Trp Phe Tyr Arg His His Tyr Glu Ser Pro His Pro Arg Ile Ser Ser
    50                  55                  60

Glu Val His Ile Pro Leu Gly Asp Ala Arg Leu Val Ile Thr Thr Tyr
65                  70                  75                  80

Trp Gly Leu His Thr Gly Glu Arg Asp Trp His Leu Gly Gln Gly Val
                85                  90                  95

Ser Ile Glu Trp Arg Lys Lys Arg Tyr Ser Thr Gln Val Asp Pro Glu
            100                 105                 110

Leu Ala Asp Gln Leu Ile His Leu Tyr Tyr Phe Asp Cys Phe Ser Asp
        115                 120                 125

Ser Ala Ile Arg Lys Ala Leu Leu Gly His Ile Val Ser Pro Arg Cys
    130                 135                 140

Glu Tyr Gln Ala Gly His Asn Lys Val Gly Ser Leu Gln Tyr Leu Ala
145                 150                 155                 160

Leu Ala Ala Leu Ile Thr Pro Lys Lys Ile Lys Pro Pro Leu Pro Ser
                165                 170                 175

Val Thr Lys Leu Thr Glu Asp Arg Trp Asn Lys Pro Gln Lys Thr Lys
            180                 185                 190

Gly His Arg Gly Ser His Thr Met Asn Gly His
        195                 200


<210> SEQ ID NO 11
<211> LENGTH: 863
<212> TYPE: PRT
<213> ORGANISM: HTLV-III
<220> FEATURE:
<221> NAME/KEY: MISC_FEATURE
<222> LOCATION: (1)..(863)
<223> OTHER INFORMATION: env protein of HTLV-III

<400> SEQUENCE: 11

Lys Glu Gln Lys Thr Val Ala Met Arg Val Lys Glu Lys Tyr Gln His
1               5                   10                  15

Leu Trp Arg Trp Gly Trp Arg Trp Gly Thr Met Leu Leu Gly Met Leu
            20                  25                  30

Met Ile Cys Ser Ala Thr Glu Lys Leu Trp Val Thr Val Tyr Tyr Gly
        35                  40                  45

Val Pro Val Trp Lys Glu Ala Thr Thr Thr Leu Phe Cys Ala Ser Asp
    50                  55                  60

Ala Lys Ala Tyr Asp Thr Glu Val His Asn Val Trp Ala Thr His Ala
65                  70                  75                  80

Cys Val Pro Thr Asp Pro Asn Pro Gln Glu Val Val Leu Val Asn Val
                85                  90                  95

Thr Glu Asn Phe Asn Met Trp Lys Asn Asp Met Val Glu Gln Met His
            100                 105                 110

Glu Asp Ile Ile Ser Leu Trp Asp Gln Ser Leu Lys Pro Cys Val Lys
        115                 120                 125

Leu Thr Pro Leu Cys Val Ser Leu Lys Cys Thr Asp Leu Lys Asn Asp
    130                 135                 140

Thr Asn Thr Asn Ser Ser Ser Gly Arg Met Ile Met Glu Lys Gly Glu
145                 150                 155                 160

Ile Lys Asn Cys Ser Phe Asn Ile Ser Thr Ser Ile Arg Gly Lys Val
                165                 170                 175

Gln Lys Glu Tyr Ala Phe Phe Tyr Lys Leu Asp Ile Ile Pro Ile Asp
            180                 185                 190
```

```
Asn Asp Thr Thr Ser Tyr Thr Leu Thr Ser Cys Asn Thr Ser Val Ile
        195                 200                 205

Thr Gln Ala Cys Pro Lys Val Ser Phe Glu Pro Ile Pro Ile His Tyr
    210                 215                 220

Cys Ala Pro Ala Gly Phe Ala Ile Leu Lys Cys Asn Asn Lys Thr Phe
225                 230                 235                 240

Asn Gly Thr Gly Pro Cys Thr Asn Val Ser Thr Val Gln Cys Thr His
                245                 250                 255

Gly Ile Arg Pro Val Val Ser Thr Gln Leu Leu Leu Asn Gly Ser Leu
            260                 265                 270

Ala Glu Glu Glu Val Val Ile Arg Ser Ala Asn Phe Thr Asp Asn Ala
        275                 280                 285

Lys Thr Ile Ile Val Gln Leu Asn Gln Ser Val Glu Ile Asn Cys Thr
    290                 295                 300

Arg Pro Asn Asn Asn Thr Arg Lys Ser Ile Arg Ile Gln Arg Gly Pro
305                 310                 315                 320

Gly Arg Ala Phe Val Thr Ile Gly Lys Ile Gly Asn Met Arg Gln Ala
                325                 330                 335

His Cys Asn Ile Ser Arg Ala Lys Trp Asn Asn Thr Leu Lys Gln Ile
            340                 345                 350

Asp Ser Lys Leu Arg Glu Gln Phe Gly Asn Asn Lys Thr Ile Ile Phe
        355                 360                 365

Lys Gln Ser Ser Gly Gly Asp Pro Glu Ile Val Thr His Ser Phe Asn
    370                 375                 380

Cys Gly Gly Glu Phe Phe Tyr Cys Asn Ser Thr Gln Leu Phe Asn Ser
385                 390                 395                 400

Thr Trp Phe Asn Ser Thr Trp Ser Thr Lys Gly Ser Asn Asn Thr Glu
                405                 410                 415

Gly Ser Asp Thr Ile Thr Leu Pro Cys Arg Ile Lys Gln Ile Ile Asn
            420                 425                 430

Met Trp Gln Glu Val Gly Lys Ala Met Tyr Ala Pro Pro Ile Ser Gly
        435                 440                 445

Gln Ile Arg Cys Ser Ser Asn Ile Thr Gly Leu Leu Leu Thr Arg Asp
    450                 455                 460

Gly Gly Asn Ser Asn Asn Glu Ser Glu Ile Phe Arg Pro Gly Gly Gly
465                 470                 475                 480

Asp Met Arg Asp Asn Trp Arg Ser Glu Leu Tyr Lys Tyr Lys Val Val
                485                 490                 495

Lys Ile Glu Pro Leu Gly Val Ala Pro Thr Lys Ala Lys Arg Arg Val
            500                 505                 510

Val Gln Arg Glu Lys Arg Ala Val Gly Ile Gly Ala Leu Phe Leu Gly
        515                 520                 525

Phe Leu Gly Ala Ala Gly Ser Thr Met Gly Ala Ala Ser Met Thr Leu
    530                 535                 540

Thr Val Gln Ala Arg Gln Leu Leu Ser Gly Ile Val Gln Gln Gln Asn
545                 550                 555                 560

Asn Leu Leu Arg Ala Ile Glu Ala Gln Gln His Leu Leu Gln Leu Thr
                565                 570                 575

Val Trp Gly Ile Lys Gln Leu Gln Ala Arg Ile Leu Ala Val Glu Arg
            580                 585                 590

Tyr Leu Lys Asp Gln Gln Leu Leu Gly Ile Trp Gly Cys Ser Gly Lys
        595                 600                 605

Leu Ile Cys Thr Thr Ala Val Pro Trp Asn Ala Ser Trp Ser Asn Lys
```

-continued

```
    610                 615                 620

Ser Leu Glu Gln Ile Trp Asn Asn Met Thr Trp Met Glu Trp Asp Arg
625                 630                 635                 640

Glu Ile Asn Asn Tyr Thr Ser Leu Ile His Ser Leu Ile Glu Glu Ser
                645                 650                 655

Gln Asn Gln Gln Glu Lys Asn Glu Gln Glu Leu Leu Glu Leu Asp Lys
            660                 665                 670

Trp Ala Ser Leu Trp Asn Trp Phe Asn Ile Thr Asn Trp Leu Trp Tyr
        675                 680                 685

Ile Lys Leu Phe Ile Met Ile Val Gly Gly Leu Val Gly Leu Arg Ile
    690                 695                 700

Val Phe Ala Val Leu Ser Val Val Asn Arg Val Arg Gln Gly Tyr Ser
705                 710                 715                 720

Pro Leu Ser Phe Gln Thr His Leu Pro Ile Pro Arg Gly Pro Asp Arg
                725                 730                 735

Pro Glu Gly Ile Glu Glu Glu Gly Gly Glu Arg Asp Arg Asp Arg Ser
            740                 745                 750

Ile Arg Leu Val Asn Gly Ser Leu Ala Leu Ile Trp Asp Asp Leu Arg
        755                 760                 765

Ser Leu Cys Leu Phe Ser Tyr His Arg Leu Arg Asp Leu Leu Leu Ile
    770                 775                 780

Val Thr Arg Ile Val Glu Leu Leu Gly Arg Arg Gly Trp Glu Ala Leu
785                 790                 795                 800

Lys Tyr Trp Trp Asn Leu Leu Gln Tyr Trp Ser Gln Glu Leu Lys Asn
                805                 810                 815

Ser Ala Val Ser Leu Leu Asn Ala Thr Ala Ile Ala Val Ala Glu Gly
            820                 825                 830

Thr Asp Arg Val Ile Glu Val Val Gln Gly Ala Tyr Arg Ala Ile Arg
        835                 840                 845

His Ile Pro Arg Arg Ile Arg Gln Gly Leu Glu Arg Ile Leu Leu
    850                 855                 860
```

CLONING AND EXPRESSION OF HIV-1 DNA

RELATED APPLICATIONS

This application is a continuation-in-part of U.S. application Ser. No. 06/659,339 filed Oct. 10, 1984, now abandoned, which is a continuation-in-part of U.S. application Ser. No. 06/643,306, filed Aug. 22, 1984, now abandoned.

TECHNICAL FIELDS

This invention is in the fields of molecular biology and virology and in particular relates to human T cell leukemia virus-type III (HTLV-III). By scientific convention, HTLV-III, has been renamed HIV-1.

BACKGROUND

The term human T cell leukemia-lymphoma virus (HTLV) refers to a unique family of T cell tropic retroviruses. These viruses play an important role in the pathogenesis of certain T cell neoplasms. There are presently three known types of HTLVs. One subgroup of the family, HTLV-type I (HTLV-I), is linked to the cause of adult T-cell leukemia-lymphoma (ATLL) that occurs in certain regions of Japan, the Caribbean and Africa. HTLV-type II (HTLV-II) has been isolated from a patient with a T-cell variant of hairy cell leukemia. M. Popovic et al., Detection, Isolation, and Continuous Production of Cytopathic Retroviruses (HTLV-III) from Patients with AIDS and Pre-AIDS. *Science,* 224:497-500 (1984).

HTLV-type III (HTLV-III) has been isolated from many patients with acquired immunodeficiency syndrome, (AIDS). HTLV-III refers to prototype virus isolated from AIDS patients. Groups reported to be at greatest risk for AIDS include homosexual or bisexual males; intravenous drug users and Haitian immigrants to the United States. Hemophiliacs who receive blood products pooled from donors and recipients of multiple blood transfusions are also at risk. Clinical manifestations of AIDS include severe, unexplained immune deficiency which generally involves a depletion of helper T lymphocytes. These may be accompanied by malignancies and infections. The mortality rate for patients with AIDS is high. A less severe form of AIDS also exists, in which there may be lymphadenopathy and depressed helper T cell counts; there is not, however, the devastating illness characteristic of full-blown AIDS. There are many individuals, who are classified as having early AIDS (pre-AIDS), who exhibit these signs. It is not now possible to predict who among them will develop the more serious symptoms.

Much of the evidence implicates HTLV-III as the etiological agent of the infectious AIDS. First, there is consistent epidemiology; greater than 95% of the patients with AIDS have antibodies specific for HTLV-III. Second, there has been reproducible identification and isolation of virus in this disease; more than 100 variants of HTLV-III have been isolated from AIDS patients. Third, there has been transmission of the disease to normal healthy individuals who received blood transfusions from infected blood donors.

HTLV-III has been shown to share several properties with HTLV-I and HTLV-II but also to be morphologically, biologically and antigenically distinguishable. R. C. Gallo et al., Frequent Detection and Isolation of Cytopathic Retroviruses (HTLV-III) from Patients with AIDS and At Risk for AIDS. *Science,* 224:500-5030 (1984). For example, HTLV-III has been shown to be antigenically related to HTLV-I and HTLV-II by demonstrating cross-reactivity with antibodies to HTLV-I and HTLV-II core proteins, p24 and p19, and envelope antigens and by nucleic acid cross-hybridization studies with cloned HTLV-I and HTLV-II DNAs. However, unlike HTLV-I and HTLV-II, it lacked the ability to infect and transform T cells from normal umbilical cord blood and bone marrow in vitro, and has the cytopathic effect on infected cells only.

Like the RNA genome of other retroviruses, the RNA genome of HTLV-III contains three genes which encode viral proteins: 1) the gag gene, which encodes the internal structural (nucleocapsid or core) proteins; 2) the pol gene, which encodes the RNA-directed DNA polymerase (reverse transcriptase); and 3) the env gene, which encodes the envelope glycoproteins of the virion. In addition, the HTLV-III genome contains a region designated Px, located between the env gene and the 3' LTR, which appears to be involved in functional killing of the virus.

At this time, AIDS is still difficult to diagnose before the onset of clinical manifestations. There is no method presently available for the prevention of the disease. Treatment of those with AIDS is generally not successful and victims succumb to the devastating effects HTLV-III has on the body.

SUMMARY OF THE INVENTION

This invention is based upon applicant's cloning of HTLV-III DNA in recombinant/vector host systems capable of expressing immunoreactive HTLV-III polypeptides. Based on the cloning of HTLV-III DNA in systems which express immunoreactive-polypeptides, applicant has developed methods useful in the diagnosis, treatment and prevention of AIDS. Applicant has developed methods of detecting HTLV-III and antibodies against HTLV-III in body fluids (e.g., blood, saliva, semen), and methods useful in immunotherapy (e.g., vaccination and passive immunization against AIDS). In addition, applicant has developed methods of making HTLV-III DNA probes and RNA probes useful in detecting HTLV-III in body fluids.

Polypeptides encoded by segments of the HTLV-III genome have been produced by these recombinant DNA methods. For example, polypeptides encoded by three regions of the HTLV-III genome (an env gene sequence, an env-lor gene sequence and a 1.1 Kb EcoRI restriction fragment from HTLV-III cDNA) have been produced. The polypeptides expressed have been isolated. These polypeptides are immunoreactive with sera of patients having AIDS and with antibodies to HTLV-III and thus are useful in screening blood and other body fluids for the presence of antibodies against HTLV-III. Applicant's invention therefore provides a method not only for diagnosing AIDS, but also for preventing the transmission of the disease to others through blood or blood components harboring HTLV-III. The latter is particularly valuable in screening donated blood before it is transfused or used to obtain blood components (e.g., Factor VIII for the treatment of hemophilia; Factor IX)

Polypeptides produced by the recombinant DNA methods are employed in the production of antibodies, including monoclonal antibodies, against the virus. Such antibodies form the basis for immunoassay and diagnostic techniques for directly detecting HTLV-III in body fluids such as blood, saliva, semen, etc. Neutralizing antibodies against the virus may be used to passively immunize against the disease.

Applicant's cloning of HTLV-III DNA in such recombinant vector host systems also provides the basis for determination of the nucleotide sequence of HTLV-III DNA. The DNA probes are homologous to DNA regions which are unique to the HTLV-III genome. DNA probes provide another method of detecting HTLV-III in blood, saliva or other body fluids. RNA probes which contain regions unique to the HTLV-III genome can also be formed and used for the detection of HTLV-III in body fluids.

BRIEF DESCRIPTION OF THE FIGURES

FIG. 1*a* shows sites at which the genome is cut by the restriction enzyme SstI and FIG. 1*b* shows the fragments of HTLV-III genome produced through the action of restriction enzymes Kpn, EcoRI and Hind III.

FIG. 2*a* shows the location of restriction enzyme sites in the genome and FIG. 2*b* shows the location in the HTLV-III genome of DNA inserts in open reading frame clones. The (+) and (−) indicate reactivity and lack of reactivity, respectively, of the fusion protein expressed by cells transformed by the ORF vectors with sera of AIDS patients.

FIG. 6*a* shows the nucleotide sequence of the ompA signal peptide and the pertinent region of recombinant plasmids ompA1-R-6; ompA2-R-7 and ompA3-R-3.

FIG. 10*a* is an immunoblot showing the position on SDS polyacrylamide gel of lambdaCI-HTLV-III beta-galactosidase fusion proteins, and FIG. 10*b* shows the immunoreactivity of such proteins with sera from AIDS patients.

BEST MODE OF CARRYING OUT THE INVENTION

Figure 1:
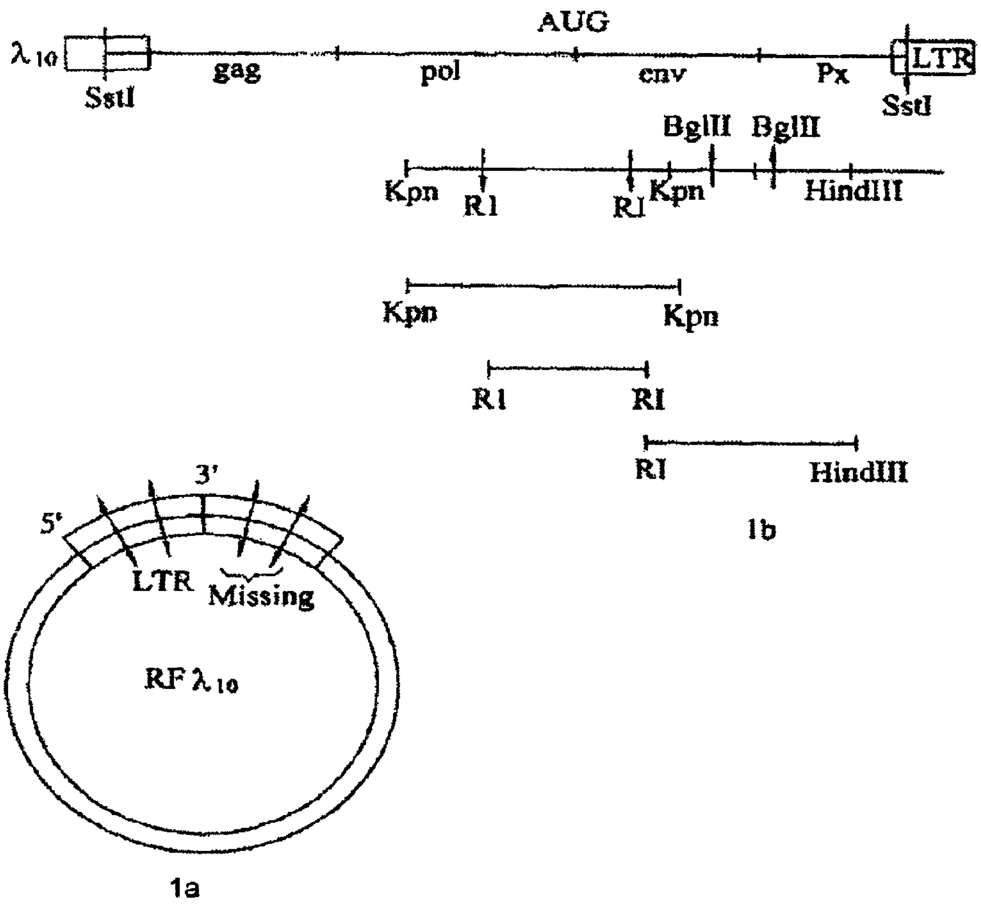
FIG. 1 is a representation of HTLV-III DNA.

Despite the similarity between HTLV-III and the other members of the HTLV-bovine leukemia virus (BLV) family of viruses, the biology and pathology of HTLV-III differs substantially. For example, relatively little homology has been found in the HTLV-III genome when compared with that of the HTLV-I or -II genome. Infection with HTLV-III often results in profound immunosuppression (AIDS), consequent to the depletion of the OKT4(+) cell population. This effect is mirrored by a pronounced cytopathic, rather than transforming, effect of HTLV-III infection upon the OKT4(+) cells in lymphocyte cultures in vitro. In contrast, infection with HTLV-I results in a low incidence of T-cell leukemia lymphoma (an OKT4(+) cell malignancy). There is evidence for some degree of immunodeficiency in HTLV-I patients as well. Infection of primary lymphocytes in culture by HTLV-I and -II results in vitro transformation of predominantly OKT4(+) cells. A cytopathic effect of HTLV-I infection upon lymphocytes is apparent, but the effect is not as pronounced as that observed for HTLV-III.

HTLV-III also differs from HTLV-I and -II in the extent of infectious virion production in vivo and in vitro. High titers of cell free, infectious virions can be obtained from AIDS patient semen and saliva and from the supernatant of cultures infected with HTLV-III. Very few, if any, cell free infectious virions can be recovered from adult T-cell leukemia lymphoma (ATLL) patients or from cultures infected with HTLV-I or -II.

Envelope glycoprotein is the major antigen recognized by the antiserum of AIDS patients. In this respect, HTLV resembles other retroviruses, for which the envelope glycoprotein is typically the most antigenic viral polypeptide. In addition, the neutralizing antibodies are generally directed toward the envelope glycoprotein of the retrovirus. Serum samples from 88 percent to 100 percent of those with AIDS have been shown to have antibodies reactive with antigens of HTLV-III; the major immune reactivity was directed against p41, the presumed envelope antigen of HTLV-III. Antibodies to core proteins have also been demonstrated in serum of AIDS patients, but do not appear to be as effective an indicator of infection as is the presence of antibodies to envelope antigen.

The p41 antigen of HTLV-III has been difficult to characterize because the viral envelope is partially destroyed during the process of virus inactivation and purification. This invention responds to the great need to characterize this antigenic component of the HTLV-III virus and to determine the existence and identity of other viral antigenic components in several ways. It provides products, such as HTLV-III polypeptides, antibodies to the polypeptides and RNA and DNA probes, as well as methods for their production. These serve as the basis for screening, diagnostic and therapeutic products and methods.

This invention relates to HTLV-III polypeptides which are produced by translation of recombinant DNA sequences encoding HTLV-III proteins. Polypeptides which are produced in this way and which are immunoreactive with serum from AIDS patients or antibodies to HTLV-III are referred to as recombinant DNA-produced immunoreactive HTLV-III polypeptides. They include, but are not limited to, antigenic HTLV-III core and envelope polypeptides which are produced by translation of the recombinant DNA sequences specific to the gag and the env DNA sequences encoding HTLV-III core proteins and envelope glycoproteins, respectively. They also include the polypeptides which are produced by translation of the recombinant DNA sequences included in a 1.1 Kb EcoRI restriction fragment of HTLV-III cDNA and recombinant DNA sequences specific to the sor gene and the Px genes of HTLV-III. The sor DNA sequence is common to replication competent HTLV-III viruses. The Px genes contain a coding sequence with one large open reading frame (lor), located between the env gene and the 3' end of the HTLV-III genome. Both the env DNA sequences and the lor DNA sequences are located within the same open reading frame of the HTLV-III genome and this gene region is accordingly designated env-lor.

The polypeptides encoded by these regions of the HTLV III can be used in immunochemical assays for detecting antibodies against HTLV-III and HTLV-V infection. These methods can assist in diagnosing AIDS. In addition, they can also be employed to screen blood before it is used for transfusions or for the production of blood components (e.g., Factor VIII for the treatment of hemophilia). Availability of screening technics will reduce the risk of AIDS transmission.

Detection of antibodies reactive with the polypeptides can be carried out by a number of established methods. For example, an immunoreactive HTLV III polypeptide can be affixed to a solid phase (such as polystyrene bead or other solid support). The sold phase is then incubated with blood sample to be tested for antibody against HTLV-III. After an appropriate incubation period the solid phase and blood sample are separated. Antibody bound to the solid phase can be detected with labeled polypeptide or with a labeled antibody against human immunoglobulin.

HTLV-III polypeptides can be used in a vaccine useful for prevention of AIDS. For vaccination against the virus, immunogenic polypeptides which elicit neutralizing antibody would be employed. The leading candidates for use in vaccines are the viral envelop polypeptides.

The polypeptides can also be used to produce antibodies, including monoclonal antibodies, against the HTLV-III polypeptides. These antibodies can be used in immunochemical assays for direct detection of the virus in body fluids (such as blood, saliva and semen). Assays employing monoclonal antibody against specific HTLV III antigenic determinants will reduce false-positive results thereby improving accuracy of assays for the virus. Antibodies against the virus may also be useful in immunotherapy. For example, antibodies may be used to passively immunize against the virus.

The methods of producing the polypeptides are also a subject of this invention, as are diagnostic methods based on these polypeptides.

This invention also provides methods for the isolation of genes of HTLV-III which encode immunoreactive polypeptides; identification of the nucleotide sequence of these genes; introduction of DNA sequences specific to these viral DNA sequences into appropriate vectors to produce viral RNA and the formation of DNA probes. These probes are comprised of sequences specific to HTLV-III DNA and are useful, for example, for detecting complementary HTLV-III DNA sequences in body fluids (e.g., blood).

HTLV-III Polypeptides

Genetic engineering methods are used to isolate segments of HTLV-III DNA which encode immunoreactive HTLV-III polypeptides. Among these are polypeptides which are immunoreactive with serum from AIDS patients or antibodies to HTLV-III. These polypeptides include the core protein, a 15 Kd peptide encoded by a 1.1 Kb EcoRI HTLV-III restriction fragment of HTLV-III DNA and the envelope glycoprotein. These methods are also used to sequence the fragments which encode the polypeptides. The proviral genes integrated into host cell DNA are molecularly cloned and the nucleotide sequences of the cloned provirus is determined.

Figure 2:
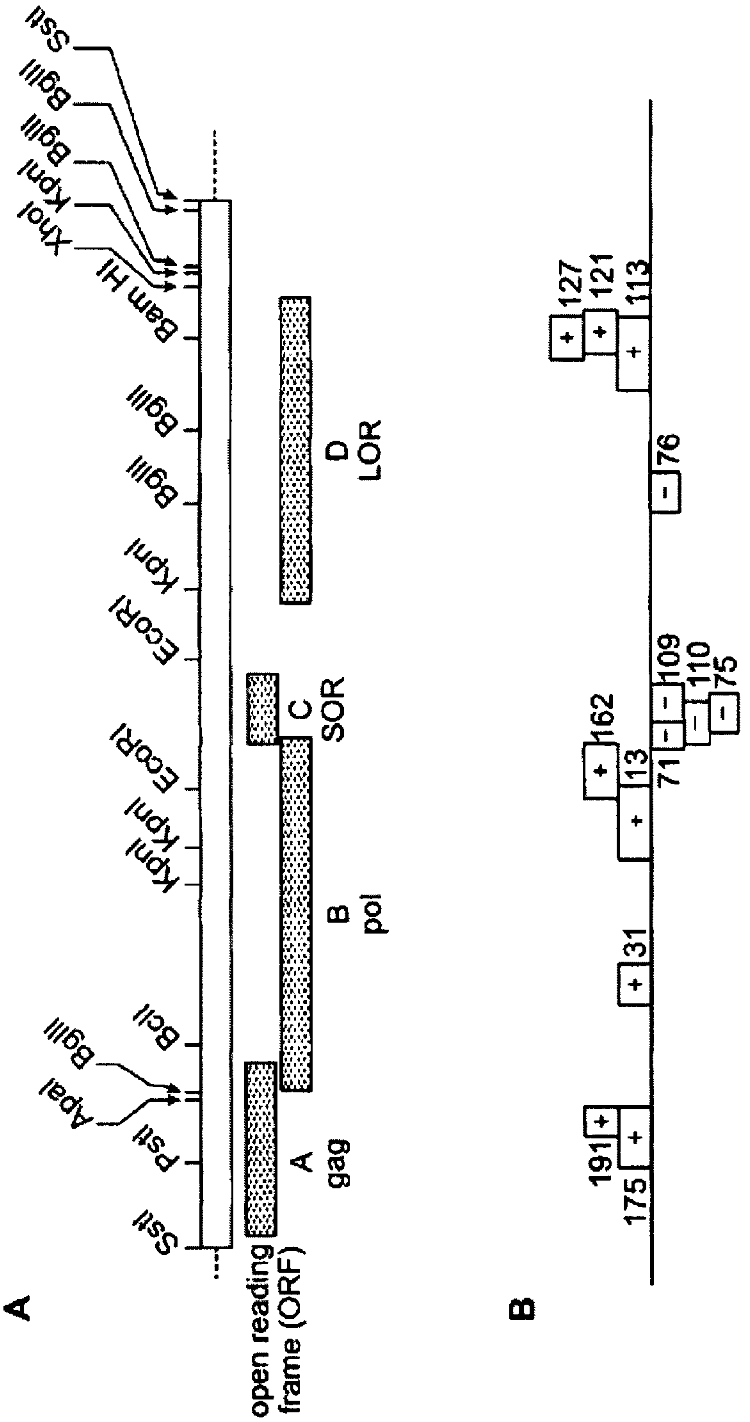
FIG. 2 is a representation of HTLV-III DNA.

An *E. coli* expression library of HTLV-III DNA is constructed. The HTLV-III genome is cloned and cuts are then made in the cloned HTLV-III genome with restriction enzymes to produce DNA fragments. (FIGS. 1 and 2) HTLV-III DNA fragments of approximately 200-500 bp are isolated from agarose gel, end repaired with $T_4$ polymerase and ligated to linker DNA. The linker ligated DNA is then treated with a restriction enzyme, purified from agarose gel and cloned in an expression vector. Examples of the expression vectors used are: OmpA, pIN (A, B and C), lambda pL, T7, lac, Trp, ORF and lambda gt11. In addition, mammalian cell vectors such as pSV28pt, pSV2neo, pSVdhfr and VPV vectors, and yeast vectors, such as GALI and GAL10, may be used.

The bacterial vectors contain the lac coding sequences, into which HTLV-III DNA can be inserted for the generation of B-galactosidase fusion protein. The recombinant vectors are then introduced into bacteria (e.g., *E. coli*); those cells which take up a vector containing HTLV-III DNA are said to be transformed. The cells are then screened to identify cells which have been transformed and are expressing the fusion protein. For example, the bacteria are plated on MacConkey agar plates in order to verify the phenotype of clone. If functional B-galactosidase is being produced, the colony will appear red.

Bacterial colonies are also screened with HTLV-III DNA probes to identify clones containing the DNA regions of interest (e.g., HTLV-III gag, pol and env DNA sequences). Clones which are positive when screened with the DNA probe and positive on the MacConkey agar plates are isolated.

This identification of cells harboring the HTLV-III DNA sequences makes it possible to produce HTLV-III polypeptides which are immunoreactive with HTLV-III specific antibody. The cells from the selected colonies are grown in culture under conditions allowing the expression of the hybrid protein. Cell protein is then obtained by means known in the art. For example, the culture can be centrifuged and the resulting cell pellet broken. Polypeptides secreted by the host cell can be obtained (without disruption of the cells) from the cell culture supernatant.

The total cellular protein is analysed by being run on an SDS polyacrylamide gel electrophoresis. The fusion proteins are identified at a position on the gel which contains no other protein. Western blot analyses are also carried out on the clones which screened positive. Such analyses are performed with serum from AIDS patients, with the result that it is possible to identify those clones expressing HTLV-III B-galactosidase fusion proteins (antigens) that cross-react with the HTLV-III specific antibody.

$Lambda_{10}$ clones harboring HTLV-III DNA are cloned from the replicated form of the virus. As the retrovirus is replicating, double stranded DNA is being produced. The cloned HTLV-III DNA is digested with the restriction enzyme SstI. (FIG. 1*a*) Because there are two SstI recognition sites within the LTR of HTLV-III DNA, one LTR region is not present in the cloned DNA sequence removed from the $lambda_{10}$ vector. As a result, a small (approximately 200 bp) fragment of the HTLV-III DNA is missing.

The resulting DNA is linearized and fragments are produced by digesting the linearized genomic DNA spanning the env gene region with restriction enzymes. For example, fragments are produced using Kpn or EcoRI plus HindIII, as shown in FIG. 1*b*. The resulting 2.3 kb KpnI-KpnI fragments; 1.0 kbEcoRI-EcoRI fragments and 2.4 Kb EcoRI-HindIII fragments are isolated by gel electrophoresis and electroelution. These fragments are randomly sheared to produce smaller fragments. The fragments thus produced are separated from agarose gel and DNA fragments between about 200-500 bp are eluted.

The eluted 200-500 bp DNA fragments are end filled through the use of *E. coli* $T_4$ polymerase and blunt end ligated into an open reading frame expression (ORF) vector, such as pMR100. This ligation may occur at the SmaI site of the pMR100 vector, which contains two promoter regions, hybrid coding sequences of lambdaCI gene and lacI-LacZ gene fusion sequence. In the vector, these are out of frame sequences; as a result, the vector is nonproductive. The HTLV-III DNA is inserted into the vector; the correct DNA fragments will correct the reading frame, with the result that CI-HTLV-III-B-galactosidase fusion proteins are produced. The expression of the hybrid is under the control of the lac promoter. Based on the sequence of pMR100, it appears that if a DNA fragment insert cloned into the SmaI site is to generate a proper open reading frame between the lambdaCI gene fragment and the lac-Z fragment, the inserted DNA must not contain any stop codons in the reading frame set by the frame of the lambdaCI gene.

The recombinant pMR100 vectors are then introduced into *E. coli*. The bacteria are plated on MacConkey agar plates to verify the phenotype of the clone. If functional B-galactosidase is being produced, the colony will appear red. The colonies are also screened with HTLV-III DNA probes, for the purpose of identifying those clones containing the insert. Clones which are positive when screened with the DNA probe and positive on the MacConkey agar plates are isolated.

Figure 4:
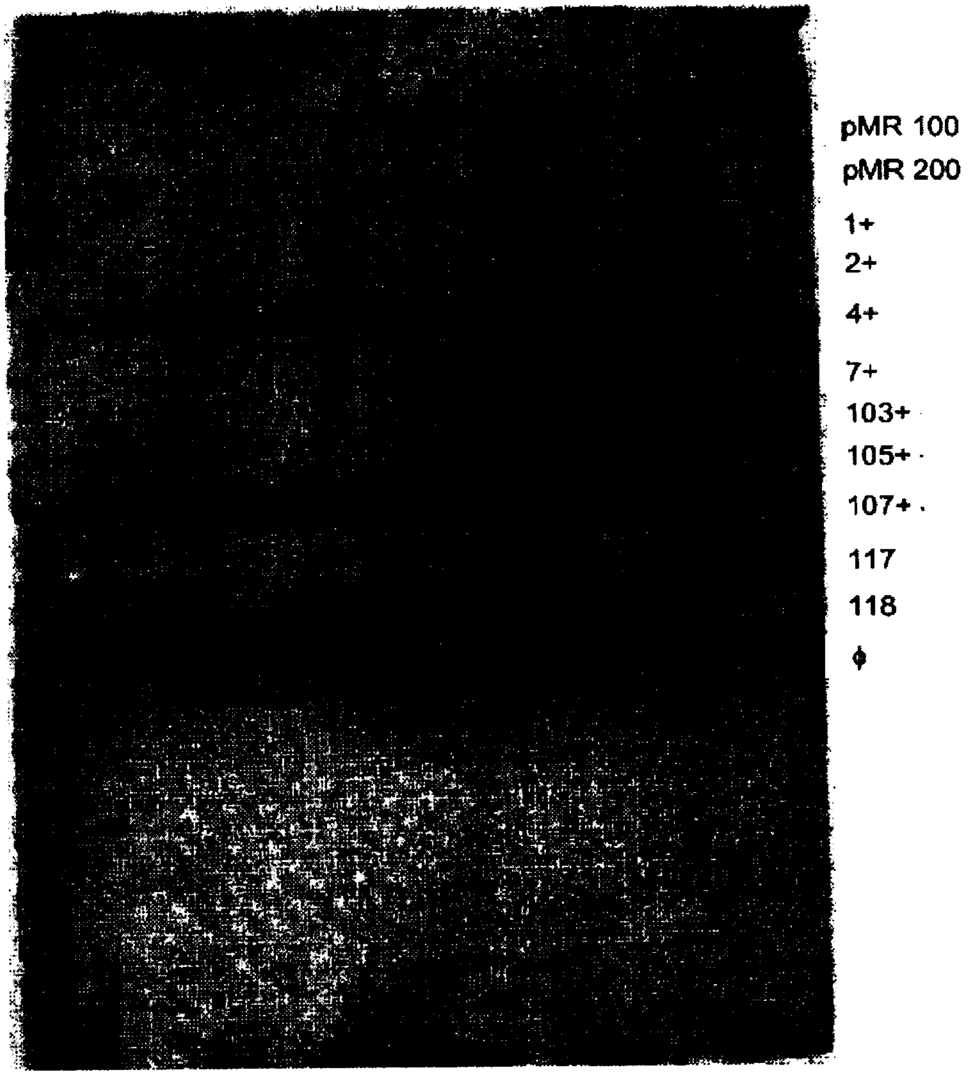
FIG. 4 is an immunoblot showing the position on an SDS polyacrylamide gel of HTLV-III env-Beta-galactosidase fusion proteins.

The cells from the selected colonies are grown in culture. The culture is spun down and the cell pellet broken. Total cellular protein is analysed by being run on an SDS polyacrylamide gel. The fusion proteins are identified at a position on the gel which contains no other protein. (FIG. 4)

Western blot analyses are also carried out on the clones which screened positive. Sera from AIDS patients are used, thus making it possible to identify those clones which express the HTLV-III-B-galactosidase fusion proteins that cross-react with the HTLV-III specific antibody.

1000 clones were screened by this method; 6 were positive.

Because of the nature of the pMR100 cloning vehicle, a productive DNA insert should also be expressed as a part of a larger fusion polypeptide. HTLV-III env gene containing recombinant clones was identified by colony hybridization. The production of larger fusion polypeptides bearing functional B-galactosidase activity was verified by phenotype identification on MacConkey agar plates; by B-galactosidase enzymatic assays and by analysis on 75% SDS-polyacrylamide gels. Immunoreactivity of the larger protein with antibody to HTLV-III was assessed by western blot analysis using serum from AIDS patients. These large fusion proteins also reacted with anti-B-galactosidase and anti-CI antiserum. This finding is consistent with the hypothesis that they are proteins of CI-HTLV-III-lacIZ.

The open reading frame insert fragment of HTLV-III is further analyzed by DNA sequencing analysis. Because one of the two BamHI sites flanking the SmaI cloning site in pMR100 is destroyed in the cloning step, positive clones are digested with restriction enzymes HindIII and claI to liberate the inserted HTLV-III DNA fragment. The HTLV-III ORF inserts are isolated from the fusion recombinant and cloned into M13 sequencing cloning vector mp18 and mp19 digested with HindIII and AccI. DNA sequences of the positive ORF clones are then determined.

Fragments of HTLV-III DNA of approximately 200-500 bps are isolated from agarose gel, end repaired with $T_4$ polymerase and ligated to EcoRI linker. The EcoRI linker ligated DNA is then treated with EcoRI purified from 1% agarose gel and cloned in an expression vector, lambda gt11. This vector contains lac Z gene coding sequences into which the foreign DNA can be inserted for the generation of B-galactosidase fusion protein. The expression of the hybrid gene is under the control of lac repressor. The lac repressor gene, lac I, is carried on a separate plasmid pMC9 in the host cell, *E. coli* Y1090. AIDS patient serum was used to probe the lambdagt11 library of HTLV-III genome DNA containing $1.5\times10^4$ recombinant phage. In a screen of 5000 recombinants, 100 independent clones that produced strong signals were isolated. The positive recombinant DNA clones were further characterized for their specific gene expression. Rabbit hyperimmune serum against P24 was also used to identify the gag gene specific clones. Nick-translated DNA probes of specific HTLV-III gene, specifically the gag gene, env gene and Px gene were used to group the positive immunoreactive clones into specific gene region.

Recombinant clones that produced strong signals with AIDS serum and contain insert DNA spanning the HTLV-III gag, pol, sor and env-lor gene regions were examined in detail by mapping their insert with restriction enzymes and DNA sequencing analysis.

Determination of the Nucleotide Sequence of HTLV-III DNA

Genetic engineering methods are used to determine the nucleotide sequence of HTLV-III DNA. One technique that can be used to determine the sequence is a shotgun/random sequencing methods. HTLV-III DNA is sheared randomly into fragments of about 300-500 bp in size. The fragments are cloned, for example, using m13, and the colonies screened to identify those having an HTLV-III DNA fragment insert. The nucleotide sequence is then generated, with multiple analysis producing overlaps in the sequence. Both strands of the HTLV-III DNA are sequenced to determine orientation. Restriction mapping is used to check the sequencing data generated.

Figure 3:
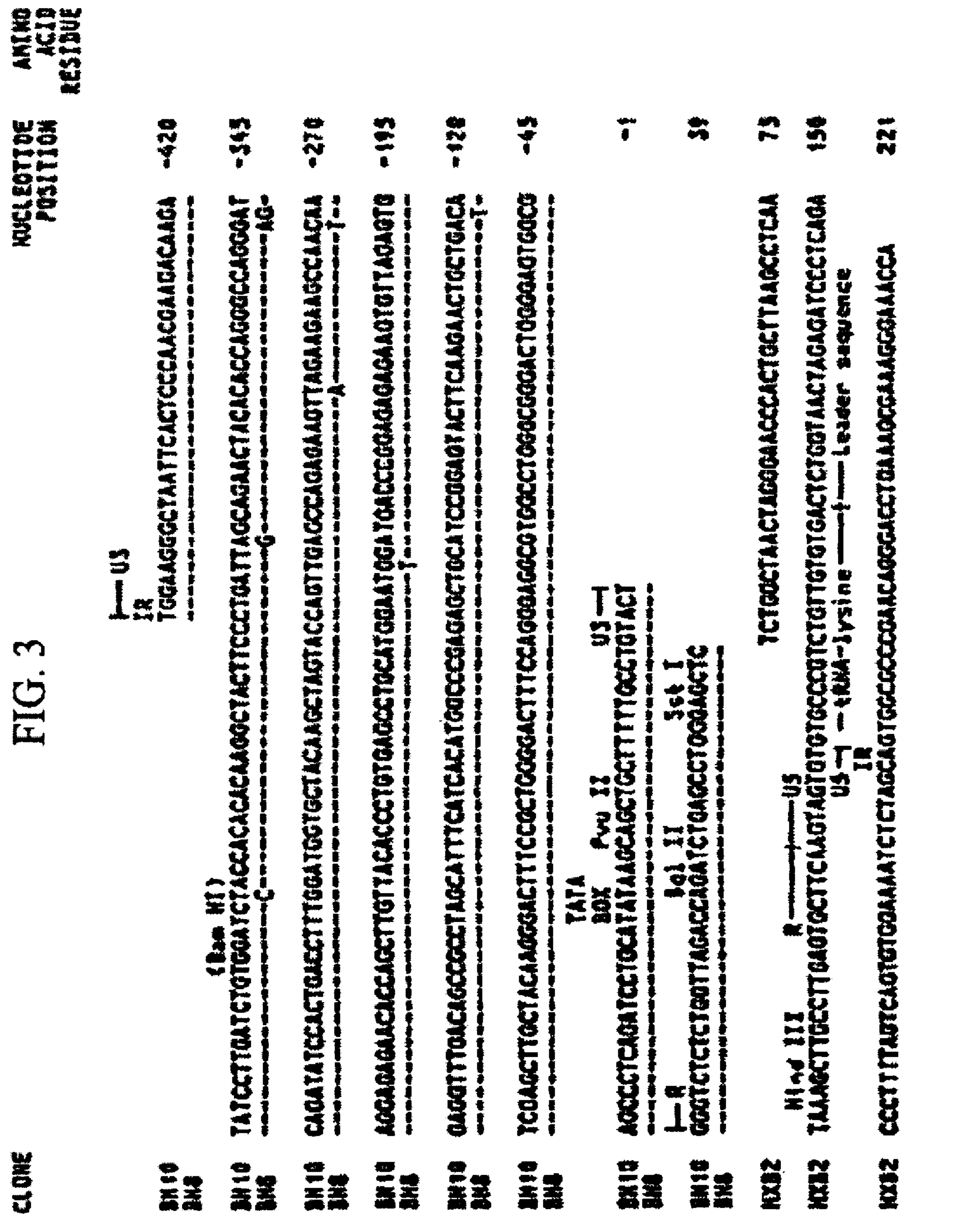
FIG. 3 shows the nucleotide sequence for HTLV-III DNA and the predicted amino acid sequence of the four longest open reading frames. Restriction enzyme sites are indicated above the nucleotide sequence.
Figure 3:
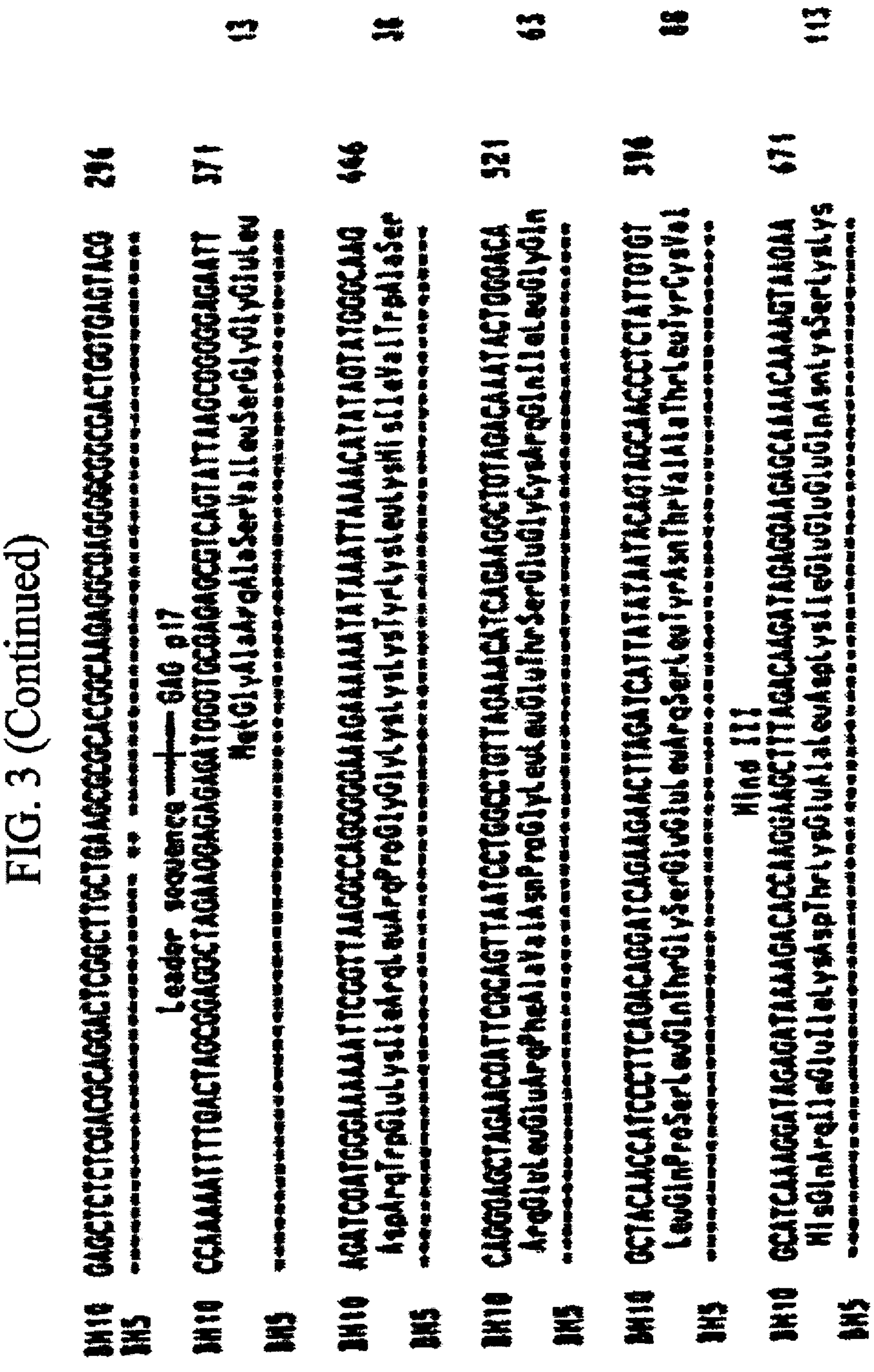
Figure 3:
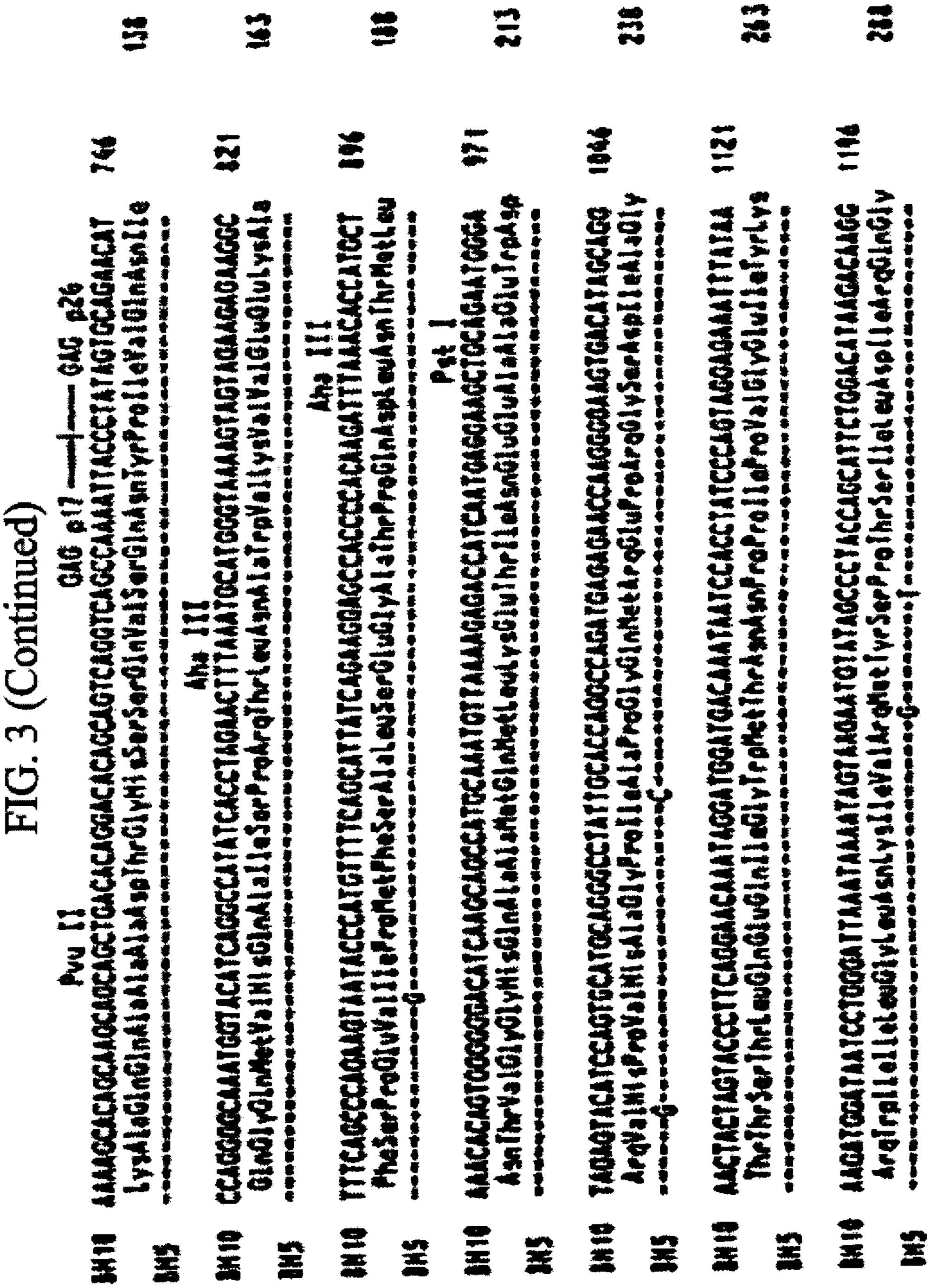
Figure 3:
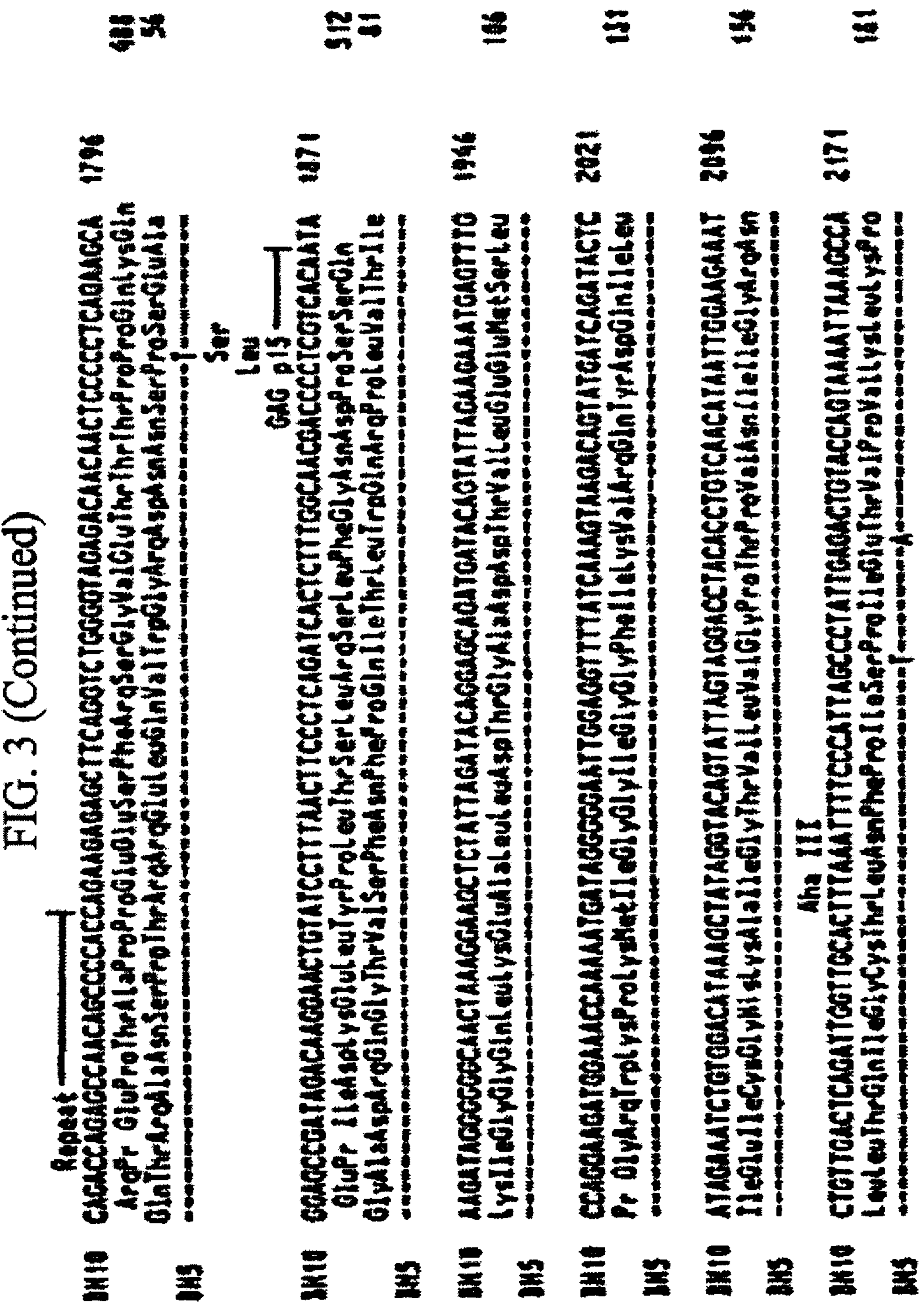
Figure 3:
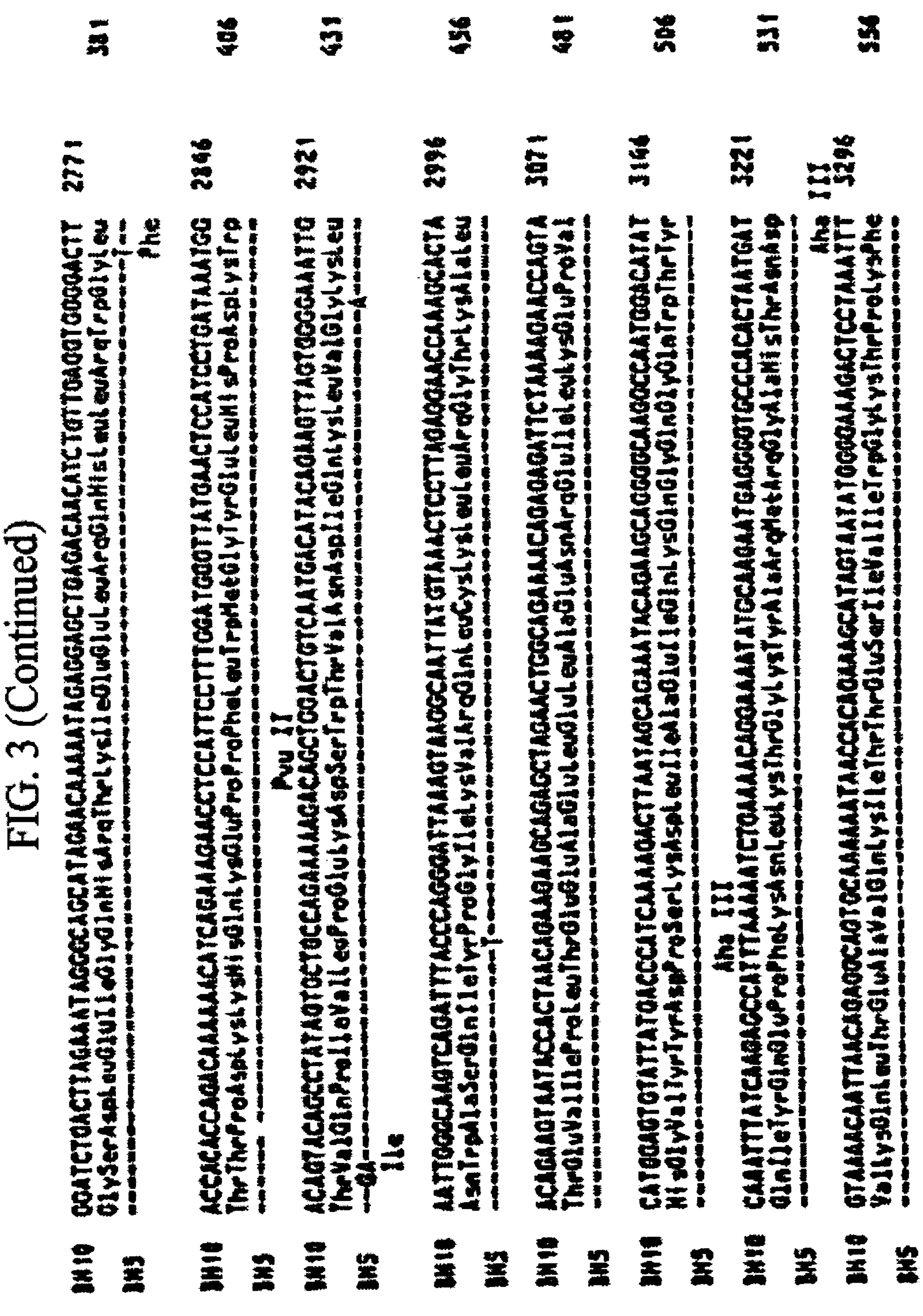
Figure 3:
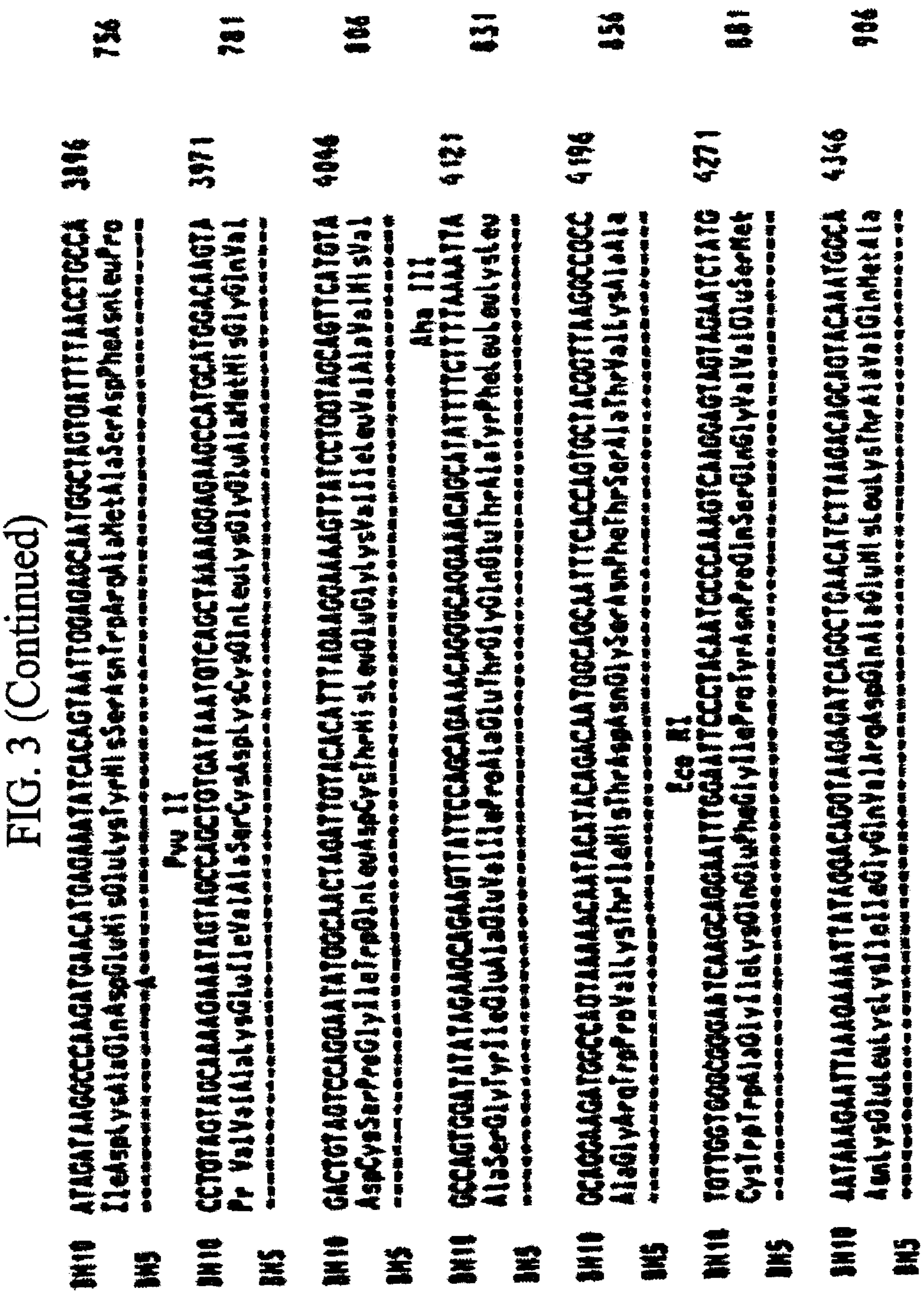
Figure 3:
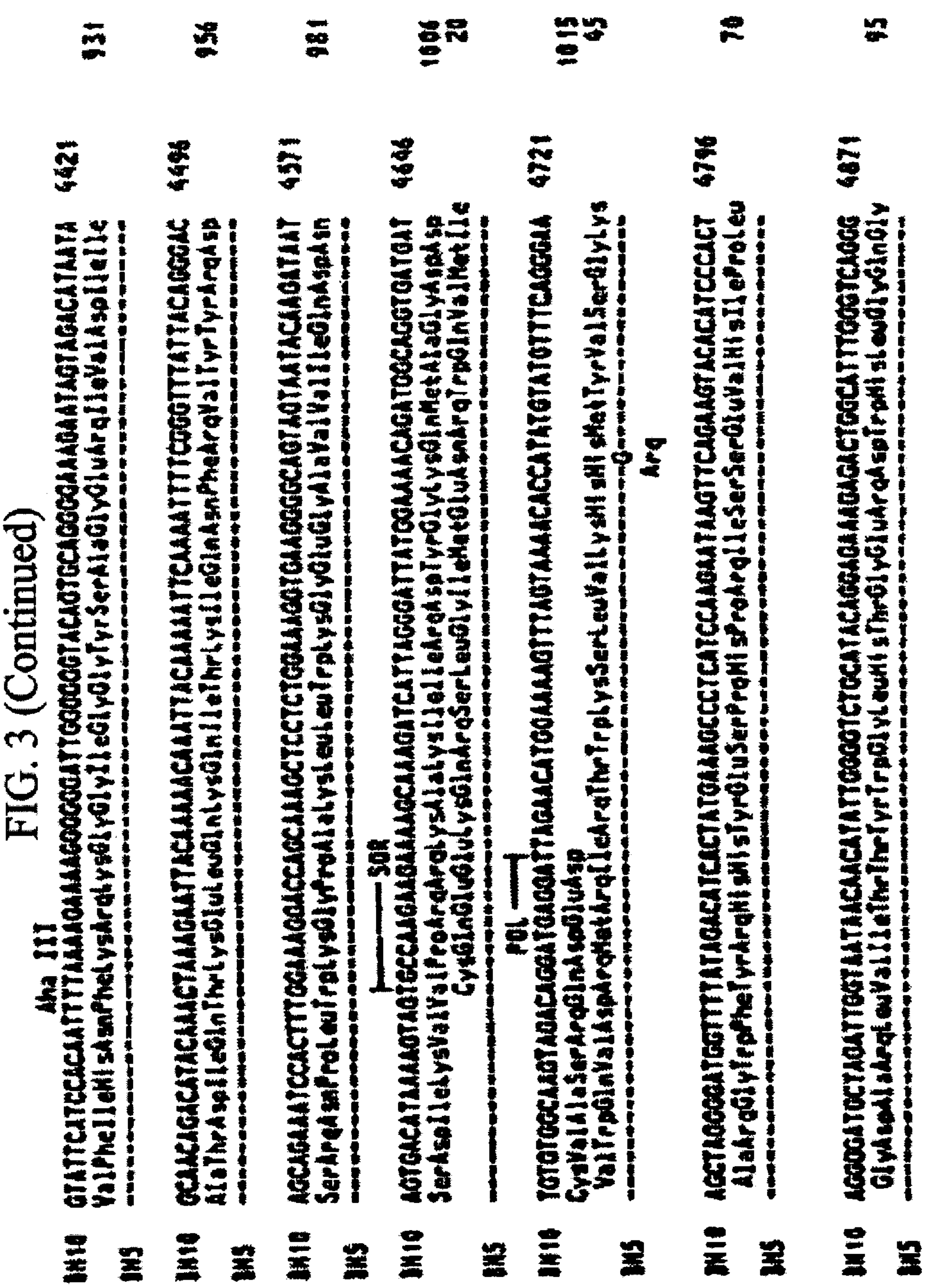
Figure 3:
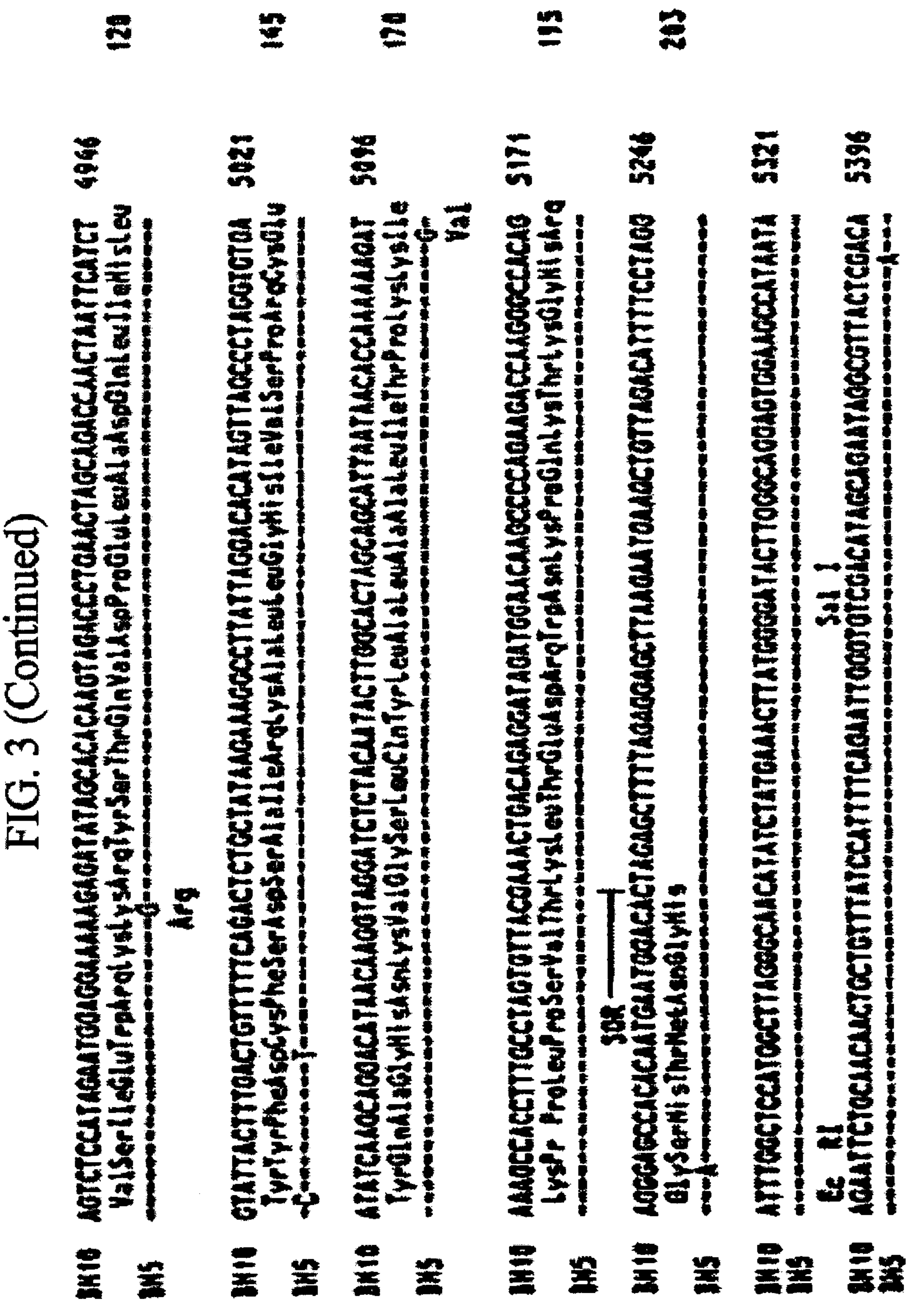
Figure 3:
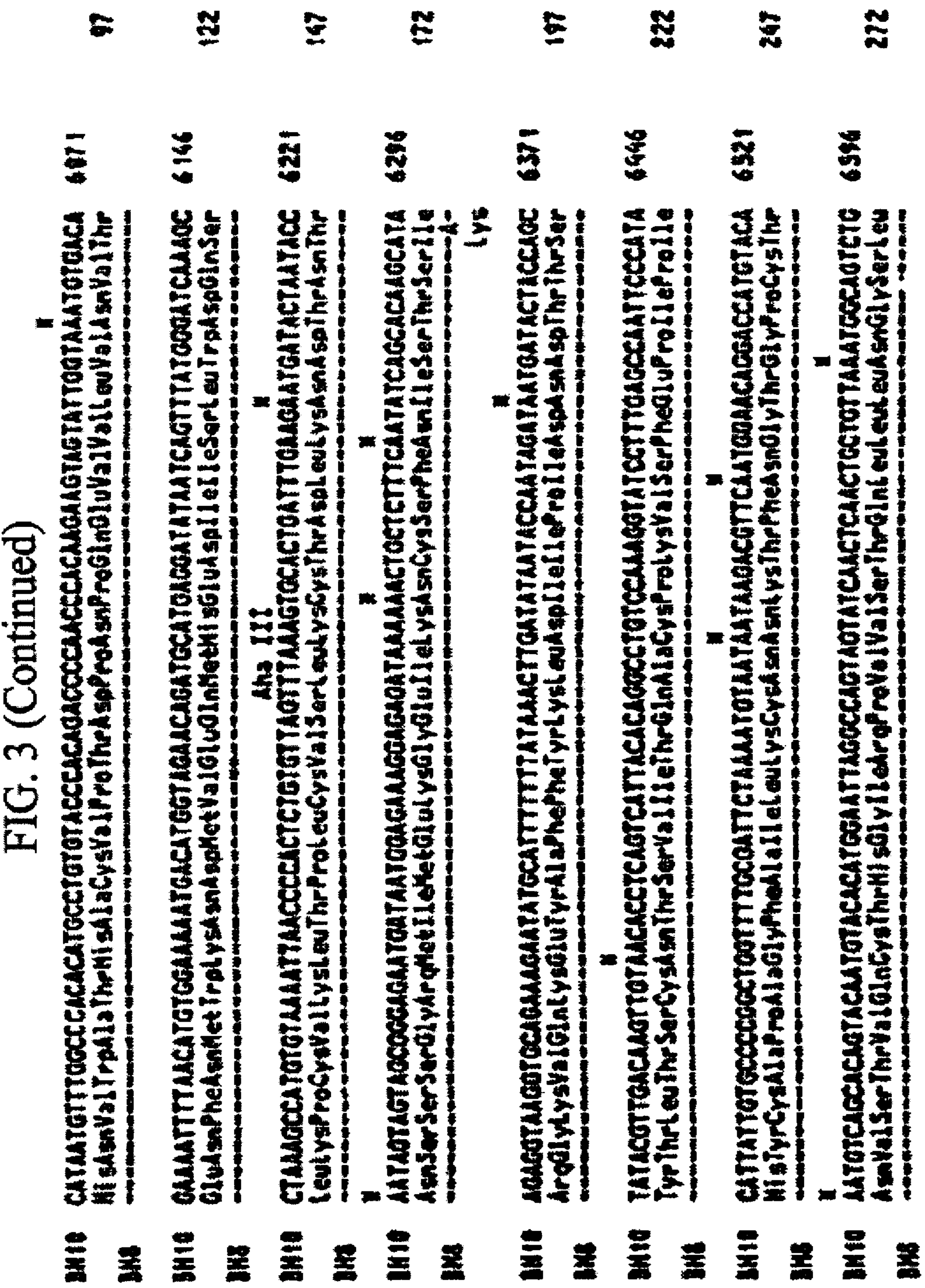
Figure 3:
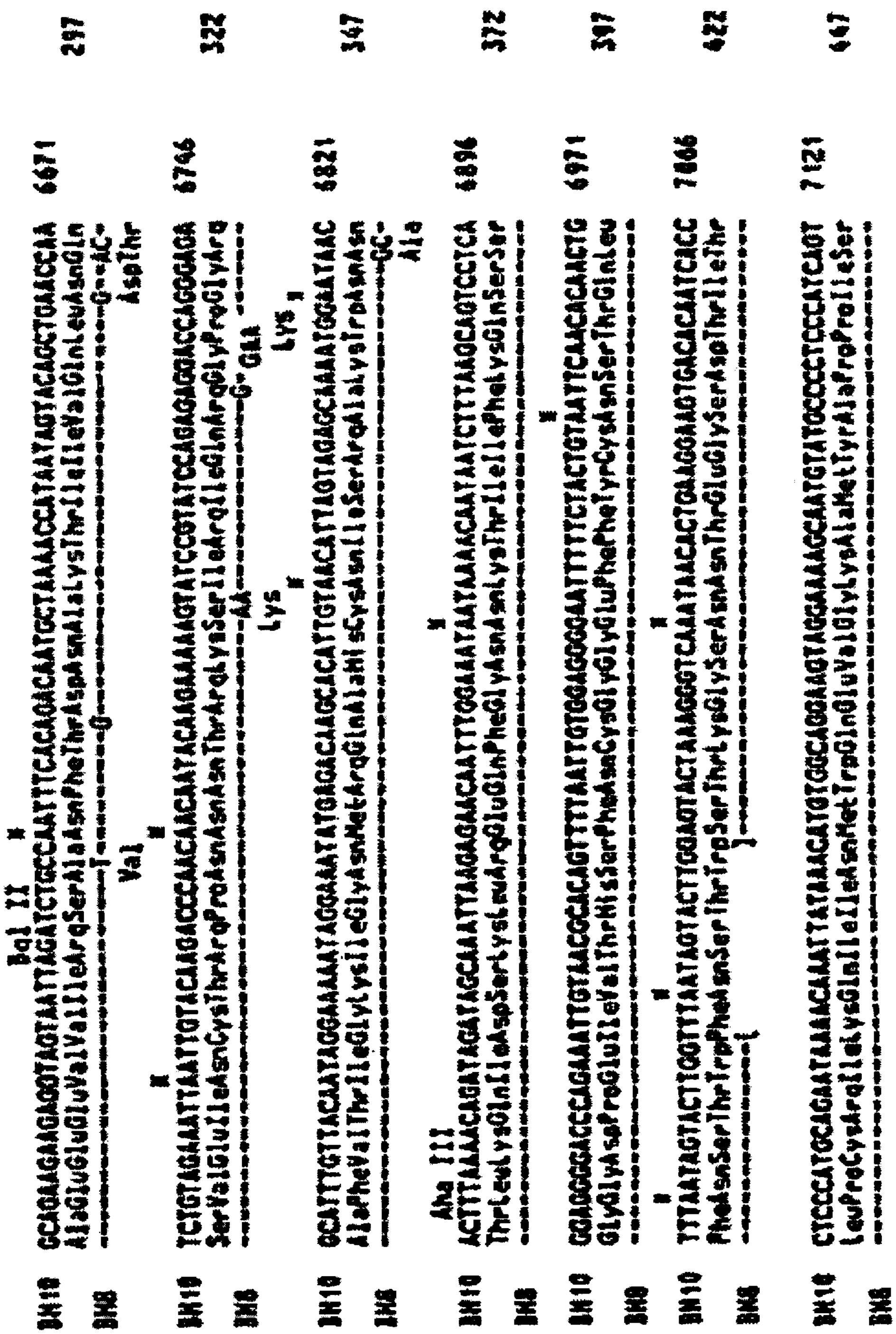
Figure 3:
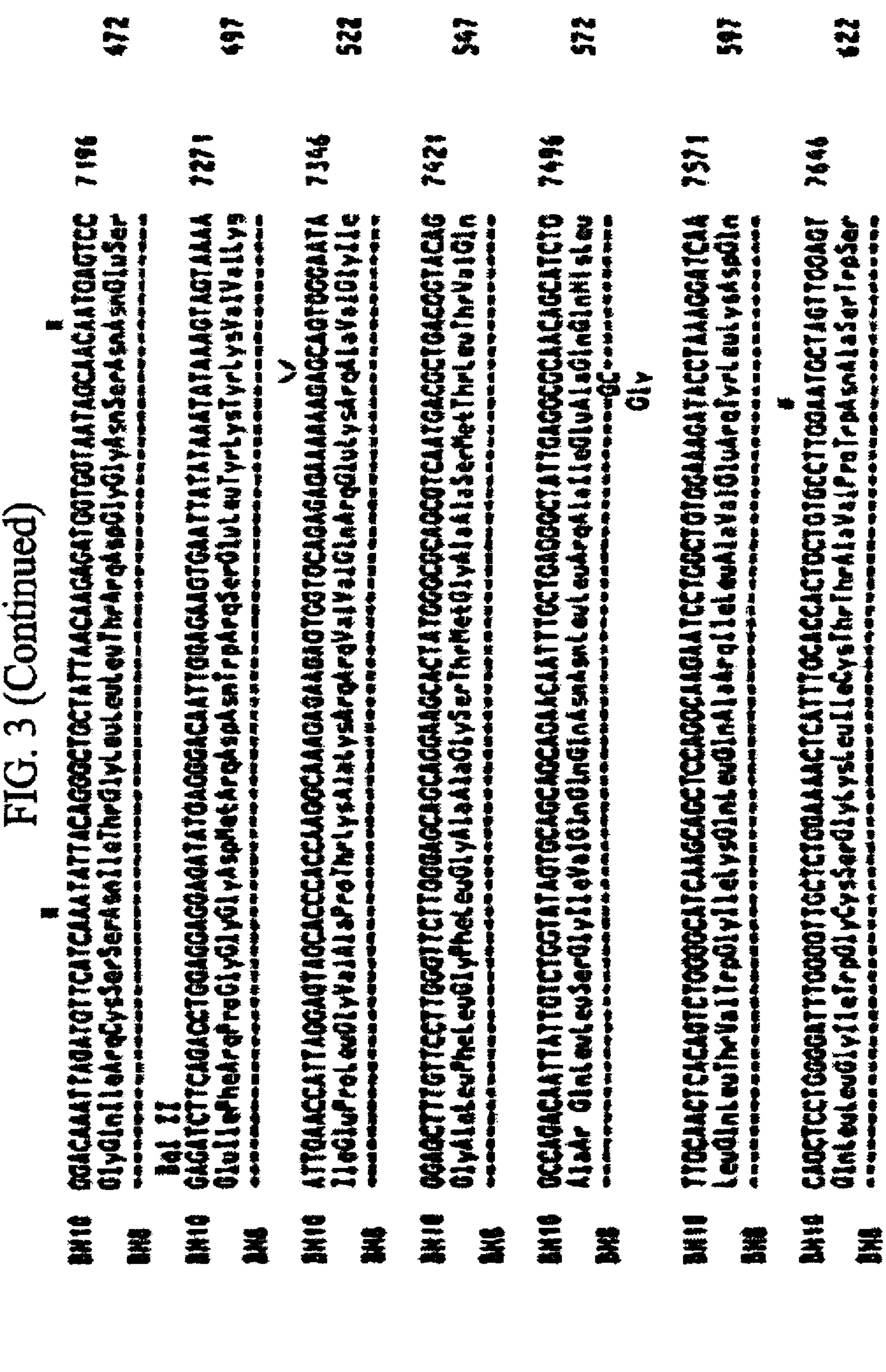
Figure 3:
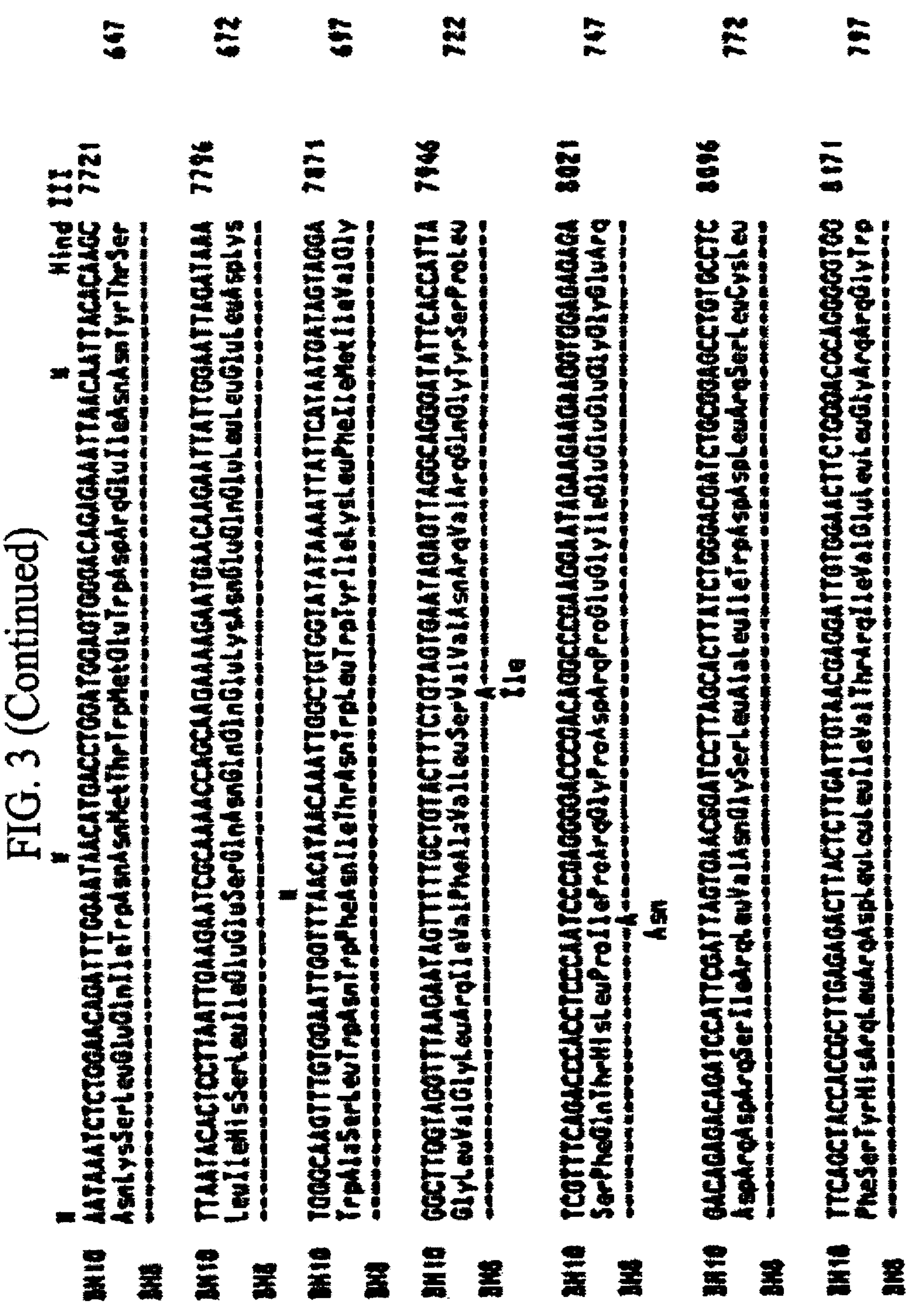
Figure 3:
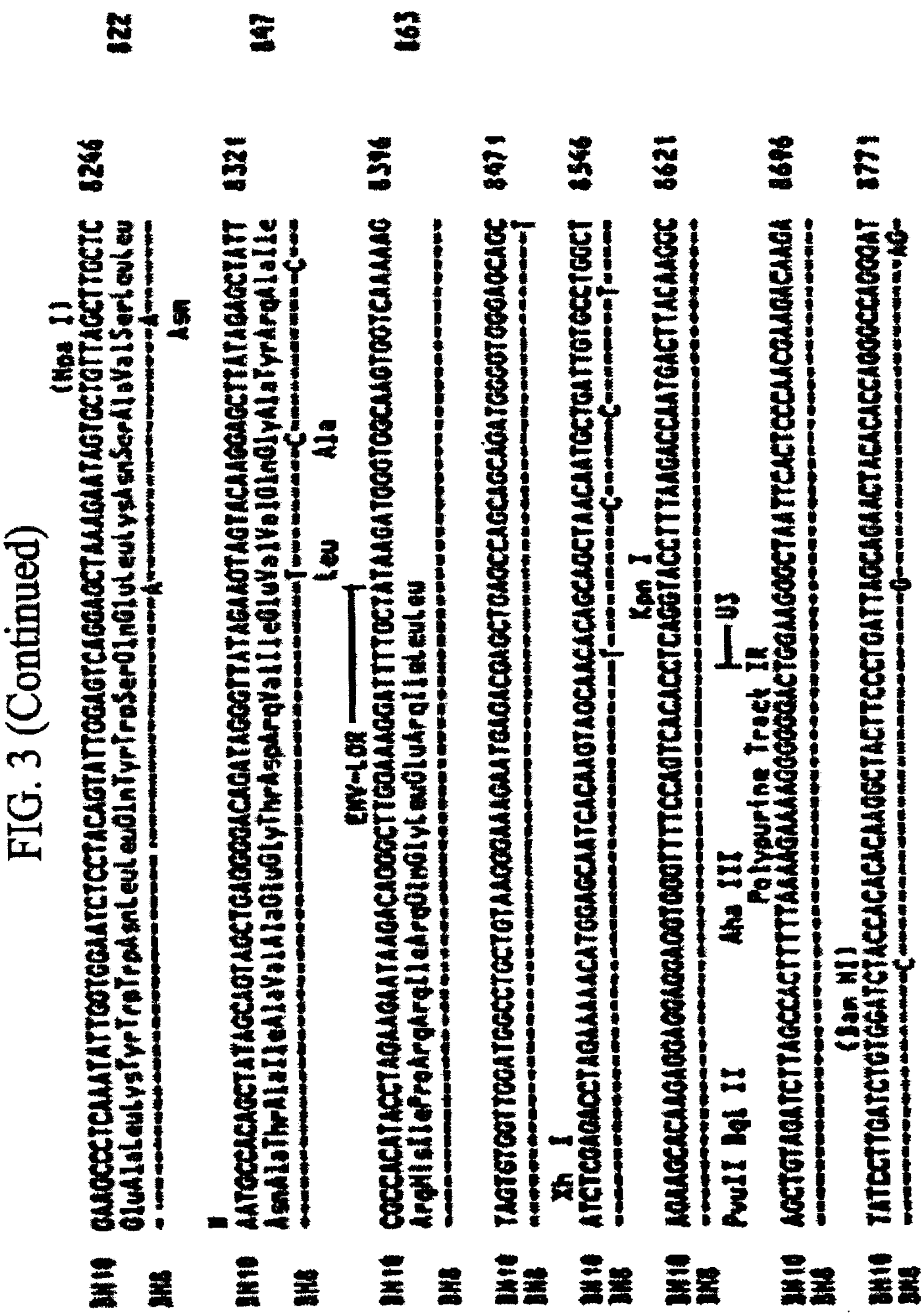
Figure 3:
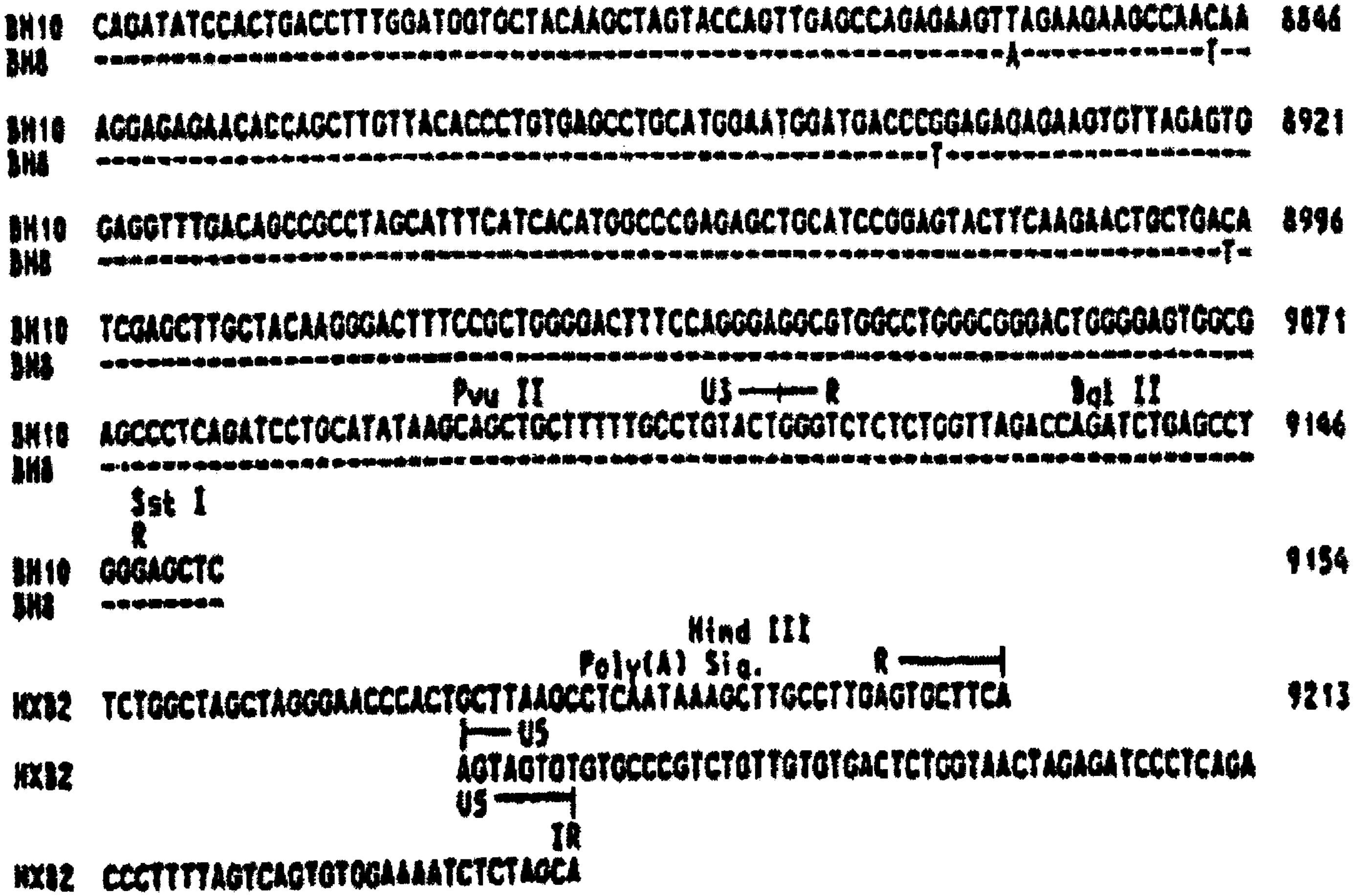

The nucleotide sequence of one cloned HTLV-III genome (BH10) is shown in FIG. 3, in which the position of sequences encoding gag protein p17 and the N-terminus of gag p24 and the C-terminus of gag p15 (which overlaps with the N-terminus of the pol protein) are indicated. The open reading frames (ORF) for pol, sor and env-lor are also indicated. The sequence of the remaining 182 base pairs of the HTLV-III DNA not present in clone BH10 (including a portion of R, U5, the tRNA primer binding site and a portion of the leader sequence) was derived from clone HXB2. The sequences of two additional clones (BH8 and BH5) are also shown. Restriction enzyme sites are listed above the nucleotide sequence; sites present in clone BH8 but not in clone BH10 are in parentheses. Deletions are noted ([ ]) at nucleotides 251, 254, 5671 and 6987-7001. The nucleotide positions (to the right of each line) start with the transcriptional initiation site. The amino acid residues are numbered (to the right of each line) for the four largest open reading frames starting after the preceding termination codon in each case except gag which is enumerated from the first methionine codon. A proposed peptide cleavage site (V) and possible asparagine-linked glycosylation sites are shown (*) for the env-lor open reading frame. The sequences in the LTR derived from clones BH8 and BH10 listed in the beginning of the figure are derived from the 3'-portion of each clone and are assumed to be identical to those present in the 5'-LTR of the integrated copies of these viral genomes.

Clone HXB2 was derived from a recombinant phage library of XbaI digested DNA from HTLV-III infected H9 cells cloned in lambdaJ1. H9 cells are human leukemic cells infected by a pool of HTLV-III from blood of AIDS patients, F. Wong-Staal, *Nature,* 312, November, 1984. Cloning vector clones BH10, BH8, and BH5 were derived from a library of SstI digested DNA from the Hirt supernatant fraction of HTLV-III infected H9 cells cloned in lambdagtWes.lambdaB. Both libraries were screened with cDNA probe synthesized from virion RNA using oligo.dT as a primer. Clones BH8, BH5, and a portion of HXB2 were sequenced as described by Maxam and Gilbert. (1980) Maxam, A. M. and Gilbert, Co.

*Methods in Enzymology*. 65: 499-560. Clone BH10 was sequenced by the method of Sanger modified by the use of oligonucleotides complementary to the M13 insert sequence as primers and using Klenow fragment of DNA polymerase I or reverse transcriptase as the polymerase.

Formation of RNA, RNA Probes and DNA Probes Specific to HTLV-III

DNA sequences which are an entire gene or segment of a gene from HTLV-III are inserted into a vector, such as a T7 vector. In this embodiment, the vector has the Tceu promoter from the T cell gene 10 promoter and DNA sequences encoding eleven amino acids from the T cell gene 10 protein.

The vectors are then used to transform cells, such as *E. coli*. The T7 vector makes use of the T7 polymerase, which catalyzes RNA formation and recognizes only T7 promoter, which is the site where RNA polymerase binds for the initiation of transcription. The T7 polymerase does not recognize *E. coli* promoter. As a result, if HTLV-III DNA sequences are inserted after the promoter and polymerase genes of the T7 vector, which recognizes them to the exclusion of other signals, and a terminator is placed immediately after the HTLV-III DNA sequences, the T7 vector will direct manufacture RNA complementary to the HTLV-III DNA insert.

Determination of the nucleotide sequence of HTLV-III DNA also provides the basis for the formation of DNA probes. Both RNA proves and DNA HTLV-III probes must have a distinctive region of the HTLV-III genome in order to be useful in detecting HTLV-III in body fluids. There is relatively little homology between the HTLV-III genome and the HTLV-I and -II genomes and probes contain regions which are unique to HTLV-III (i.e., not shared with HTLV-I or -II). For example, nucleotide sequences in the env gene region of HTLV-III can be used.

Either viral RNA or DNA can be used for detecting HTLV-III in, for example, saliva, which is known to have a very high concentration of the virus. This can be done, for example, by means of a dot blot, in which the saliva sample is denatured, blotted onto paper and then screened using either type of probe. If saliva is used as the test fluid, detection of HTLV-III is considerable faster and easier than is the case if blood is tested.

Production of Monoclonal Antibodies Reactive with HTLV-III Polypeptides

Monoclonal antibodies reactive with HTLV-III polypeptides are produced by antibody-producing cell lines. The antibody-producing cell lines may be hybridoma cell lines commonly known as hybridomas. The hybrid cells are formed by fusion of cells which produce antibody to HTLV-III polypeptide and an immortalizing cell, that is, a cell which imparts long term tissue culture stability on the hybrid cell. In the formation of the hybrid cell lines, the first fusion partner—the antibody-producing cell—can be a spleen cell of an animal immunized against HTLV-III polypeptide. Alternatively, the antibody-producing cell can be isolated B lymphocyte which produces antibody against an HTLV-III antigen. The lymphocyte can be obtained from the spleen, peripheral blood, lymph nodes or other tissue. The second fusion partner—the immortal cell—can be a lymphoblastoid cell or a plasmacytoma cell such as a myeloma cell, itself an antibody-producing cell but also malignant.

Murine hybridomas which produce monoclonal antibodies against HTLV-III polypeptide are formed by the fusion of mouse myeloma cells and spleen cells from mice immunized against the polypeptide. To immunize the mice, a variety of different immunization protocols may be followed. For instance mice may receive primary and boosting immunizations of the purified polypeptide. The fusions are accomplished by standard procedures. Kohler and Milstein, (1975) *Nature* (*London*) 256, 495-497; Kennet, R., (1980) in *Monoclonal Antibodies* (Kennet et al., Eds. pp. 365-367, Plenum Press, NY).

The hybridomas are then screened for production of antibody reactive with the polypeptide. This can be performed by screening procedures known in the art.

Another way of forming the antibody-producing cell line is by transformation of antibody-producing cells. For example, a B lymphocyte obtained from an animal immunized against HTLV-III polypeptide may be infected and transformed with a virus such as the Epstein-Barr virus in the case of human B lymphocytes to give an immortal antibody-producing cell. See, e.g., Kozbor and Rodor (1983) *Immunology Today* 4(3), 72-79. Alternatively, the B lymphocyte may be transformed by a transforming gene or transforming gene product.

The monoclonal antibodies against HTLV-III polypeptide can be produced in large quantities by injecting antibody-producing hybridomas into the peritoneal cavity of mice and, after an appropriate time, harvesting the ascites fluid which contains very high titer of homogenous antibody and isolating the monoclonal antibodies therefrom. Xenogeneic hybridomas should be injected into irradiated or athymic nude mice. Alternatively, the antibodies may be produced by culturing cells which produce HTLV-III polypeptide in vitro and isolating secreted monoclonal antibodies from the cell culture medium. The antibodies produced according to these methods can be used in diagnostic assays (e.g., detecting HTLV-III in body fluids) and in passive immunotherapy. The antibodies reactive with HTLV-III polypeptides provide the basis for diagnostic tests for the detection of AIDS or the presence of HTLV-III in biological fluids (e.g., blood, semen, saliva) and for passive immunotherapy. For example, it is possible to produce anti p 41, to attach it to a solid phase using conventional techniques and to contact the body fluid to be tested with the immobilized antibody. In this way, HTLV-III (antigen) can be detected in the body fluid; this method results in far fewer false positive test results than do tests, in which antibody against HTLV-VIII is detected.

This invention will now be further illustrated by the following examples.

Example 1

Preparation of Sonicated DNA Fragments 10 ug of gel purified HTLV-III restriction fragments were sonicated to fragment size on average of 500 bps. After sonication, the DNA was passed through a DEAE-cellulose column in 0.1×TBE in order to reduce the volume. The DEAE-bound DNA was washed with 5 ml of 0.2 M NaCl-TE (2 M NaCl, 10 mm Tris HCl pH 7.5, 1 mM EDTA) and then eluted with 1 M NaCl-TE, and ethanol precipitated. The size range of the sonicated DNA was then determined on 1.2% agarose gel. DNA fragments of desired length (200-500 bps) was eluted from the gel. T4 DNA polymerase was used to fill in and/or trim the single strand DNA termini generated by the sonication procedure. DNA fragments were incubated with T4 polymerase in the absence of added nucleotides for five minutes at 37° C. to remove nucleotides from 3' end and then all 4 nucleotide precursors were added to a final concentration of 100 uM and the reaction mixture was incubated another 30 minutes to repair the 5'-end single stranded overhang. The reaction was stopped by heat inactivation of the enzyme at 68°

C. for 10 minutes. DNA was phenol extracted once, ethanol precipitated and resuspended in TE.

Example 2

Cloning of Random Sheared DNA Fragments

The sonicated blunt end repaired HTLV-III DNA fragments were ligated into the SmaI site of the ORF expression vector pMR100 and transformed into host cell LG90 using standard transformation procedures. B-galactosidase positive phenotype of the transformant were identified by plating the transformed cell on ampicillin (25 ug/ml) containing McConkey agar plates and scoring the phenotype after 20 hours at 37° C.

Example 3

Hybrid Protein Analysis

Ten milliliter samples of cells from an over-night saturated culture grown in L broth containing ampicillin (25 ug/ml) were centrifuged, the cell pellet was resuspended in 500 ul of 1.2 fold concentrated Laemmli sample buffer. The cells were resuspended by vortexing and boiling for 3 minutes at 100° C. The lysate was then repeated by being forced through a 22 gauge needle to reduce the lysate viscosity. Approximately 10 ul of the protein samples were electrophoresed in 7.5% SDS-PAGE (SDS-polyacrylamide) gels.

Electrophoretic transfer of proteins from SDS-PAGE gels to nitrocellulose paper was carried out according to Towbin et. al. After the transfer, the filter was incubated at 37° C. for two hours in a solution of 5% (w/v) nonfat milk in PBS containing 0.1% antifoam A and 0.0001% merthiolate to saturate all available protein binding sites. Reactions with AIDS antisera were carried out in the same milk buffer containing 1% AIDS patient antisera that had been preabsorbed with *E. coli* lysate. Reactions were performed in a sealed plastic bag at 4° C. for 18-24 hours on a rotatory shaker. Following this incubation, the filter was washed three times for 20 minutes each at room temperature in a solution containing 0.5% deoxycholic, 0.1 M NaCl, 0.5% triton X-100, 10 mm phosphate buffer pH 7.5 and 0.1 mM PMSF.

To visualize antigen-antibody interactions, the nitrocellulose was then incubated with the second goat antihuman antibody that had been iodinated with $^{125}$I. The reaction with the iodinated antibody was carried out at room temperature for 30 minutes in the same milk buffer as was used for the first antibody. The nitrocellulose was then washed as previously described and exposed at −70° C. using Kodak XAR5 film with an intensifying screen.

Example 4

Screening of the HTLV-III ORF Library by Colony Hybridization

*E. coli* LG90 transformants were screened with HTLV-III DNA probes containing the DNA regions of interest (e.g. HTLV-III gag, env or Px gene specific sequences). Colonies were grown on nitrocellulose filter and screened according to the procedure of Grunstein and Hogness by using a nick-translated HTLV-III DNA as hybridization probe.

The DNA fragment was in general excised by restriction endonuclease digestion, gel purified, and $^{32}$P-labeled to a specific activity of 0.5×10$^{8}$ cpm/ug by nick-translation (Rigby, P. W. J. et al., *J. Mol. Biol.* 113, 237 (1977). Duplicate nitrocellulose filters with DNA fixed to them were prehybridized with 6×SSC (0.9 M NaCl/0.09 M sodium citrate, pH 7.0), 5×Denhardt's solution (Denhardt's solution: 0.02% each of polyvinylpyrrolidone, Ficoll and bovine serum albumin) 10 ug of denatured sonicated *E. coli* DNA per ml at 55° C. for 3-5 hours. The filters were then placed in a fresh sample of the same solution to which the denatured hybridization probe had been added. Hybridization was permitted to take place at 68° C. for 16 hours. The filters were washed repeatedly in 0.3×SSC at 55° C., and then exposed to x-ray film.

Example 5

Recombinant DNA Produced Peptide of HTLV-III which is Immunoreactive with Sera from Patients with Aids An expression vector, pIN-III-ompA (ompA) was used. ompA has the lipoprotein (the most abundant protein in *E. coli*) gene promoter (lpp) and the lacUV5 promoter-operator (FIG. 1). ompA vectors also contain the DNA segment encoding the lac repressor, which allows the expression of the inserted DNA to be regulated by lac operon inducers such as IPTG. The ompA cloning vehicles contain three unique restriction enzyme sites EcoRI, HindIII, Bam HI in all three reading frames and permit the insertion of DNA into any of these restriction sites.

Various restriction fragments were excised from the recombinant clone, lambdaBH10, which contains a 9 Kb long HTLV-III DNA insert in the SstI site of the vector lambdagtWES lambdaB. These restriction fragments were them inserted into the ompA vectors at all three reading frames and used to transform *E. coli* JA221 cells. Transformants were first screened for HTLV-III DNA by in situ colony hybridization using nick-translated HTLV-III DNA probes. The positive clones were then screened for expression of HTLV-III antigenic peptides using HTLV-III specific antibodies. For this, lysates of *E. coli* cell containing HTLV-III DNA recombinant plasmids were electrophoresed on 12.5% SDS-polyacrylamide gel and electroblotted onto nitrocellulose filters. The filters were then incubated first with well-characterized sera from AIDS patients and next with $^{125}$I-labelled goat anti-human IgG antibodies. The washed filters were autoradiographed to identify peptides reactive with anti-HTLV-III antibodies.

Figure 5:
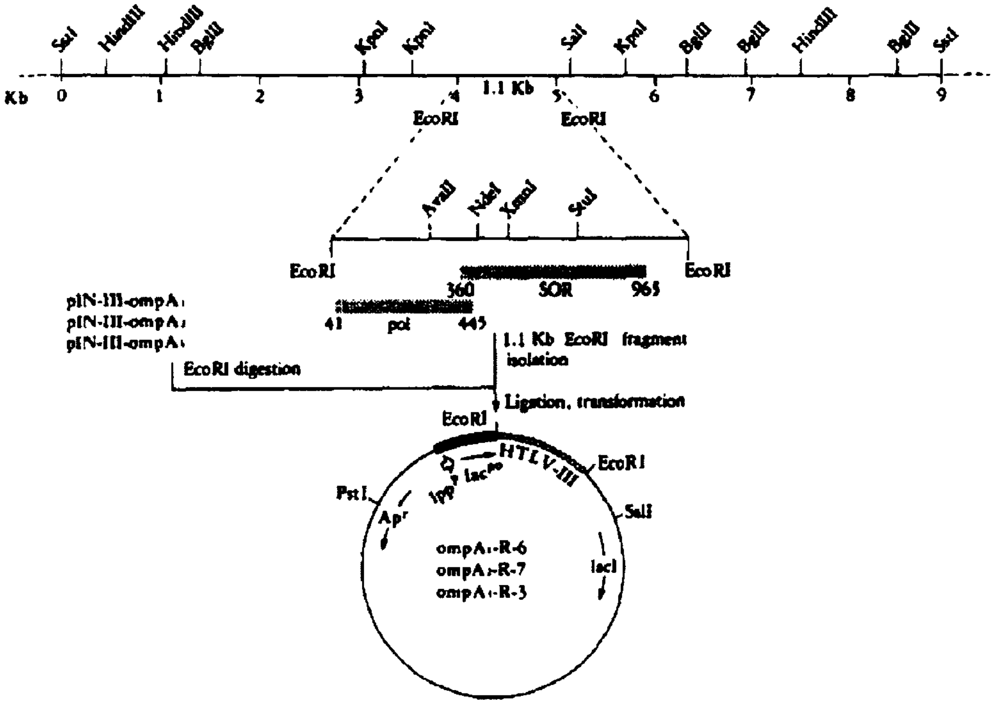
FIG. 5 shows sites at which the genome is cut by the restriction enzyme EcoRI and construction of recombinant plasmids carrying HTLV-III DNA.

Several gene segments that encode peptides showing immunoreactivity with anti-HTLV-III antibodies were demonstrated. Among these is a 1.1 Kb EcoRI restriction fragment. This fragment was inserted into ompA vectors in all three reading frames (FIG. 5). Cells were grown at 37° C. in L broth containing 100 mg/ml. ampicillin to an $^{OD}$600 of 0.2. At this time, the cell cultures were divided into two aliquots. IPTG was added to one aliquot to a final concentration of 2 mM (induced). IPTG was not added to the other aliquot (uninduced). Upon IPTG induction, transformants of all three plasmid constructs (designated OmpA$_1$-R-6 (O1R6), OmpA$_2$-R-7 (O2R7), and OmpA$_3$-R-3 (O3R3)) produced a 15 Kd peptide that is strongly reactive with anti-HTLV-III antibodies in sera from AIDS patients (FIG. 6 lane 1, purified HTLV-III virions; lanes 2 and 3, O1R6 uninduced and induced; lanes 4 and 5, 02R7 uninduced and induced; lanes 6 and 7 03R3 uninduced and induced). This reactivity is not detected when sera from normal individuals is used.

DNA sequence data of the HTLV-III genome indicates that there is an open reading frame inside the pol gene located at the 5'-end of the EcoRI fragment. DNA sequence analysis of the three recombinant constructs, O1R6, O2R7 and P3R3, confirmed that each of these recombinants has a different reading frame of the HTLV-III plus strand coupled to the coding sequence of each vector. Only in O3R3 is the reading frame of the inserted DNA in phase with that set by the signal peptide in the ompA vector; in O1R6 and O2R7 the pol gene segment DNA is out of phase (FIG. 6*a*).

There is a 6 bp ribosome binding site, AAGGAG (Shine-Dalgarno sequence), located at nucleotide position 24-29 and an initiation codon, ATG, located 11 bp downstream (position 41-43). The 15 Kd peptide synthesized by all three recombinants appears to be translated from the transcripts using this internal initiation codon. If this is true, the peptide starts from the ATG located at position 41-43 and ends at the stop codon at position 446-448, producing a peptide of 135 amino acid residues encoded by the 3'-end segment of the pol gene of HTLV-III.

Figure 6:
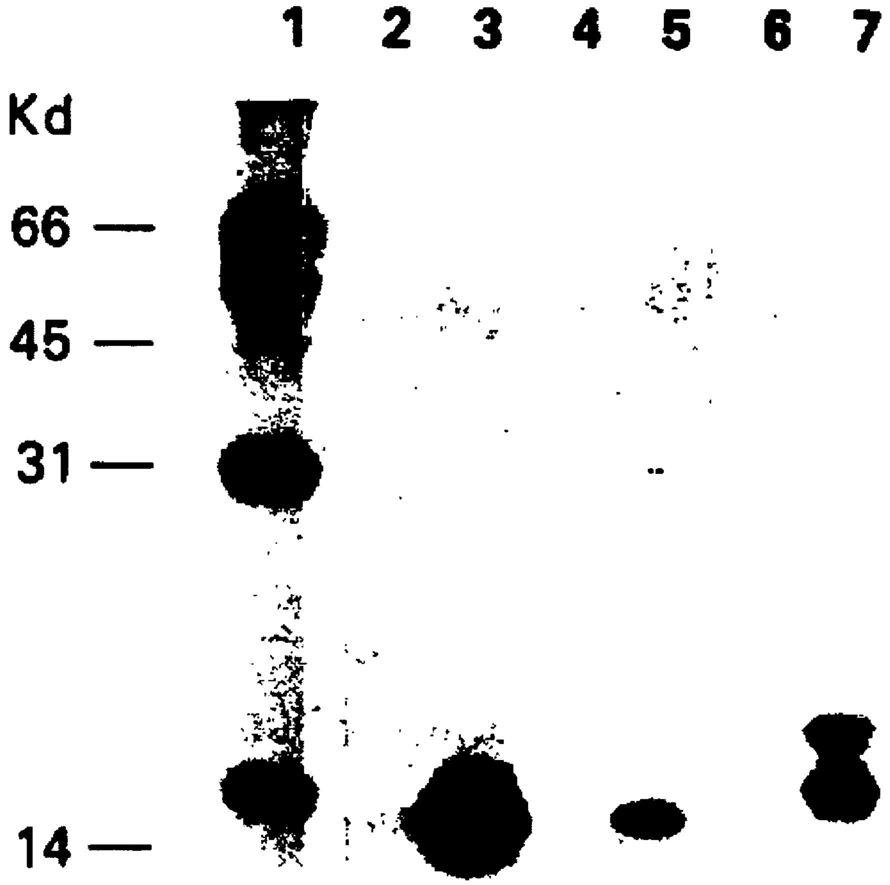
FIG. 6 is an immunoblot showing the positions on nitrocellulose blots of peptides produced by bacterial cells transformed by recombinant constructs ompA1-R-6; ompA2-R-7 and ompA3-R-3, into which a 1.1 Kb EcoRI HTLV-III cDNA restriction fragment had been inserted.

In addition to the 15 Kd peptide, the O3R3 construct, in which the reading frame of the HTLV-III DNA pol gene is in phase with that set by the vector, produced two additional peptides about 19 Kd and 16.5 Kd in size (FIG. 6). It is possible that the 19 Kd peptide contains an additional 35 amino acid residues, 21 of which are from the signal peptide encoded by the $ompA_3$ vector and 14 encoded by the inserted HTLV-III DNA itself. The 16.5 Kd peptide may be the processed 19 Kd peptide in which the signal peptide is cleaved.

The O1R6 and O2R7 constructs also produces another peptide of about 17.5 Kd (FIG. 6) and weakly reactive with sera of AIDS patients. The origin of this peptide is not clear. The 1.1 Kb EcoRI fragment contains a second potential coding region designated as the short open reading frame (SOR) extending from nucleotide position 360 to 965 (FIG. 5). Four of the five AUG methionine codons in this region are near the 5'-end of this open reading frame. This DNA segment could encode peptides of 192, 185, 177 or 164 amino acid residues. However, there is no clearly recognizable ribosome binding site at the 5'-end of this open reading frame.

Further evidence also supports the conclusion that the 15 Kd peptide is indeed derived from the pol gene. First, deletion of the 3'-end StuI to EcoRI fragment from the 1.1 Kb EcoRI insert from O1R6, O2R7 and O3R8 (FIG. 5) does not affect the synthesis of the 15 Kd peptide. Second, clones containing only the 5'-end EcoRI to NdeI fragment still produce the same 15 Kd peptide. Finally, several recombinant clones containing various DNA fragments having the SOR coding sequence properly inserted into the open reading frame cloning vector, pMR100, produced lambdaCI-HTLV-III B-galactosidase tripartite fusion proteins which have very little immunoreactivity with anti-HTLV-III antibodies present in sera from AIDS patients.

Figure 7:
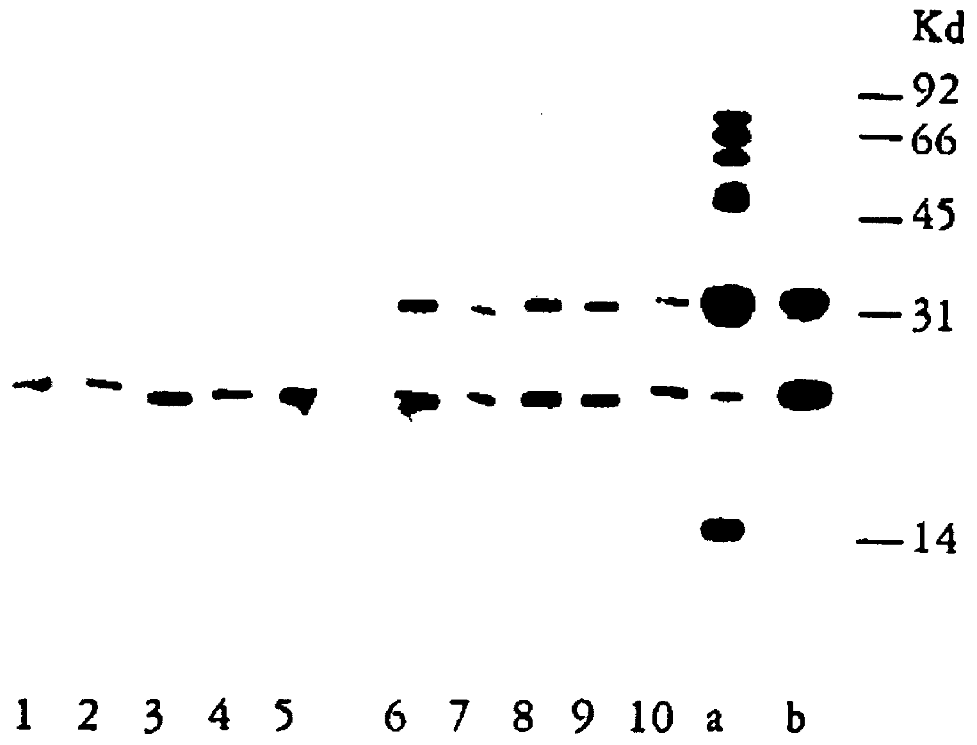
FIG. 7 is an immunoblot showing blocking of reaction between HTLV-III antigens and an AIDS serum by lysates of *E. coli* containing HTLV-III DNA recombinant plasmid ompA1-R-6 (lanes 1-5) and no blocking of the reaction by lysates of *E. coli* control cells (lanes 6-10).

Significant immunoreactivity against the 15 Kd peptide derived from the viral pol gene in sera from AIDS patients was detected. The identity of this immunoreactive peptide, with respect to the banding pattern of HTLV-III virion antigen in SDS-polyacrylamide gel electrophoresis, was determined by means of a competition inhibition immunoassay. Purified HTLV-III virions were treated with SDS, electrophoresed, and electroblotted onto a nitrocellulose filter. Identical filter strips containing disrupted HTLV-III virions were incubated with well characterized serum from an AIDS patient in the presence or absence of lysates of O1R6, O2R7, or control bacterial clones. The specific immunoreaction between anti-HTLV-III antibodies present in sera of the AIDS patients and the blotted virion proteins were then revealed by $^{125}I$-labeled goat anti-human antibody. As shown in FIG. 7, lysates of O1R6 block the immunoreactivity of the viral p31 protein with the AIDS serum, while lysates of control cells do not. This result suggests that the recombinant 15 Kd peptide encoded by 3'-end of the viral pol gene is also a part of another virion protein, p31, in contrast to the view shared by some that p31 is a cellular protein which co-purifies with HTLV-III virions.

Figure 8:
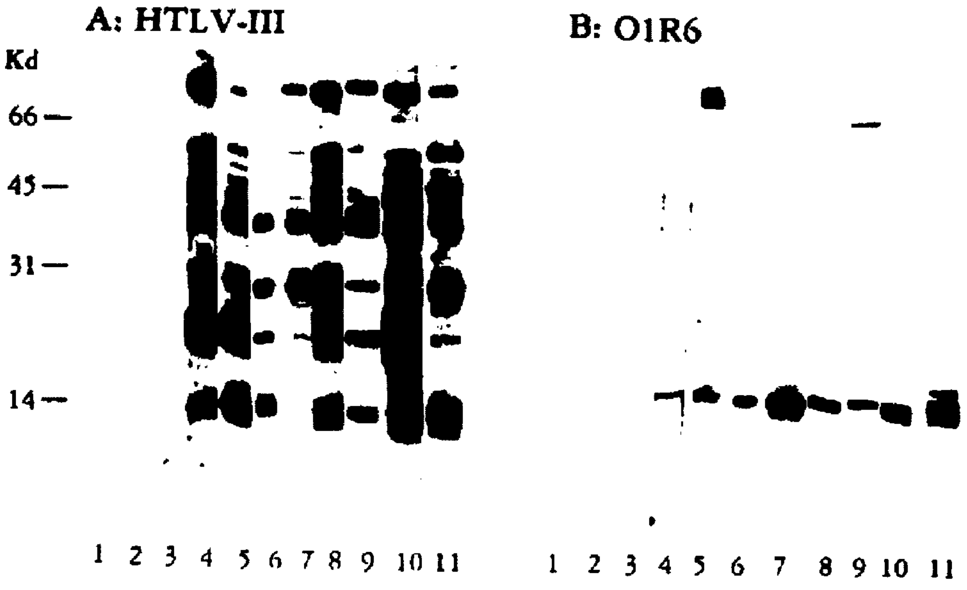
FIG. 8 is an immunoblot showing the presence or absence of antibodies against the peptide encoded by the 1.1 Kb EcoRI HTLV-III restriction fragment of HTLV-III cDNA in sera from healthy individuals (lanes 1-3) and from AIDS patients (lanes 4-11). Purified HTLV-III virus (panel A) or total cell lysate of bacterial clone ompA1-R-6(O1R6) were reacted with sera samples.

The prevalence in the sera of AIDS patients of antibodies against the 15 Kd peptide was also evaluated. In Western blot analysis employing the lysate of O1R6 as the source of antigen, a panel of coded sera from AIDS patients and normal healthy individuals was tested. All of the 20 AIDS sera and none of the 8 normal controls reacted with the 15 Kd peptide. Representative results are shown in (FIG. 8). These data indicate that most, if not all, AIDS patients produce antibodies against the viral p31 protein.

Example 6

Expression in *E. Coli* of Open Reading Frame Gene Segments of HTLV-III

Figure 9:
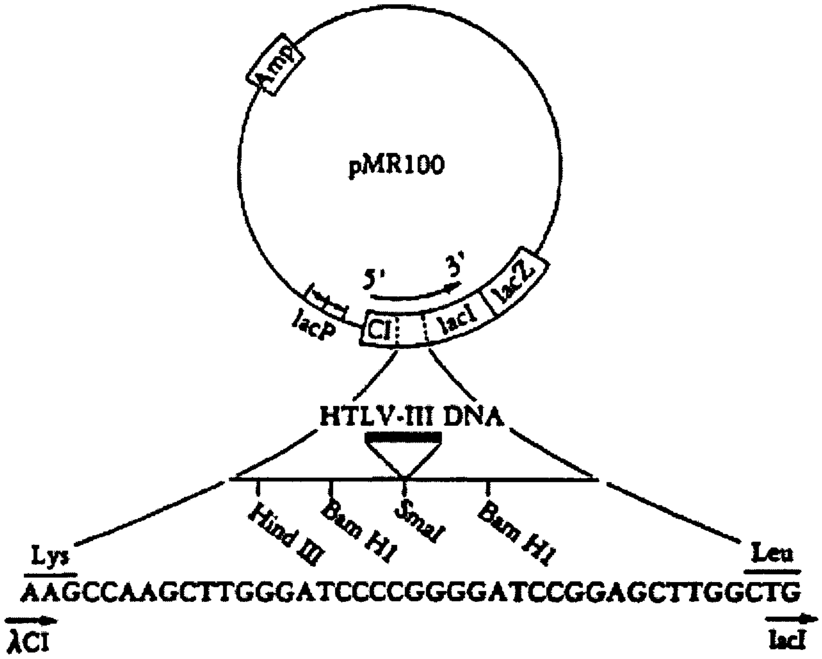
FIG. 9 represents the open reading frame expression vector pMRIOO having HTLV-III DNA.

HTLV-III DNA was excised from lambda BH-10, which is a previously constructed recombinant lambda phage containing a 9 Kb segment of HTLV-III DNA inserted into the vector lambdagtwes lambda B (FIG. 2*a*). This HTLV-III DNA was sonicated and DNA fragments of about 0.5 Kb purified by gel electrophoresis, end repaired, and inserted into the SmaI site of the open reading frame (ORF) vector, pMR100 (FIG. 9). This vector contains a bacterial lac promotor DNA segment linked to a second DNA fragment containing a hybrid coding sequence in which the N-terminus (5' segment) of the lambda CI gene of bacteriophage lambda is fused to an N-terminal-deleted lacIZ gene (3' segment). A short linker DNA fragment, containing a SmaI cloning site, has been inserted between these two fragments in such a manner that a frame shift mutation has been introduced upstream of the lacIZ-coding DNA. As a result, pMR100 does not produce any detectable B-galactosidase activity when introduced into cells of the Lac host *E. coli* LG90. The insertion of foreign DNA containing an open reading frame, in this case the HTLV-III DNA, at the SmaI cloning site can reverse the frame shift mutation if the inserted coding sequence is in the correct reading frame with respect to both the lambdaCI leader and the lacIZ gene. Transformants were screened on MacConkey plates to detect individual clones that expressed B-galactosidase enzymatic activity in situ.

Among the 6000 ampicillin resistant transformants screened, about 300 were found to express B-galactosidase activity. Colony hybridization using $^{32}p$-labelled nick-translated HTLV-III DNA as a probe revealed that all these $Lac^+$ clones contained HTLV-III DNA. In the $Lac^+$ clones the HTLV-III fragment inserted into the Sma I site of pMR100 must contain no stop codons in the reading frame set by the lambdaCI leader segment and the lacIZ gene must also be in the correct translational reading frame. The three-element-fused genes were expressed as tripartite fusion proteins, having a portion of the lambdaCI protein at the N-terminus, the HTLV-III segment in the middle, and the lacIZ polypeptide at the C-terminus.

Figure 10:
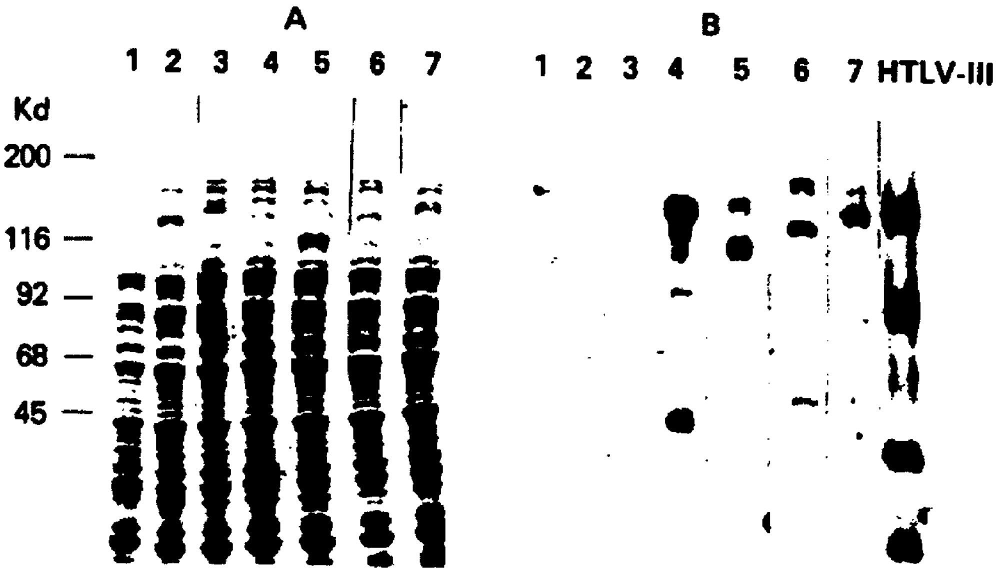
FIG. 10 represents lambdaCI-HTLV-III beta-galactosidase fusion proteins.

The proteins produced by the $Lac^+$ clones were analyzed by resolving cell lysates on 7.5% SDS-polyacrylamide gels along with those of the control $Lac^+$ clone pMR200, which produced a lambdaCI-B-galactosidase fusion protein. The lacIZ gene in pMR200 is identical to that in pMR100 except that it has a single base pair deletion which brings it in phase with the lambdaCI gene to produce an active B-galactosidase. By virtue of the very large size of the B-galactosidase and its fusion proteins, they are separated from the bulk of proteins in the cell lysates on the SDS-polyacrylamide gels and can be easily identified by Coomassie brilliant blue staining as shown in FIG. 10*a*. Some of the $Lac^+$ clones containing HTLV-III DNA produce polypeptides that are larger (15,000 to 27,000 daltons) than the lambdaCI-lacIZ fusion protein. These findings are consistent with data that the DNA inserts are up to 700 bp long. The B-galactosidase fusion proteins accounted for about 1-2% of total cellular protein.

The peptides produced by the $Lac^+$ clones were examined by Western blot analysis for immunoreactivity with sera from AIDS patients. After the lysates of $Lac^+$ clones were electrophoresed in SDS-polyacrylamide gels, they were electrotransferred to nitrocellulose filters. These protein blots were first reacted with AIDS patient sera and then with $^{125}I$-labeled goat anti-human IgG. The autoradiograph in FIG. 10*b* shows the immunoreactivity of a representative fused protein with the serum from an AIDS patient. The recombinant peptides also reacted with anti-B-galactosidase antiserum, consistent with the proposition that they had the general structure lambdaCI-HTLV-III peptide-LacIZ. From the immunoreactivity pattern of the negative controls, pMR100 and pMR200, which do not contain an HTLV-III DNA insert, it is evident that this particular AIDS serum contains antibodies reactive with several bacterial proteins of the host *E. coli*. This is not surprising, since AIDS patients are usually infected with a number of bacteria. Absorbing AIDS patient sera with Sepharose 4B conjugated with *E. coli* extract reduced the background immunoreactivity to some extent but did not completely eliminate it.

About 300 independent HTLV-III DNA-containing $Lac^+$ colonies were analyzed in SDS polyacrylamide gels using Coomassie brilliant blue staining and Western blotting. About half of them were found to express fusion proteins containing extra peptides of about 100-200 amino acids, corresponding to DNA inserts of 300-600 bp long. Of these fusion proteins, 20 were found to react specifically with sera from AIDS patients. The unreactive clones probably contain peptides that fold in such a way that they are not reactive with antibodies or correspond to regions of HTLV-III protein molecules which are not immunogenic in AIDS patients. The other half of the $Lac^+$ clones expressed fusion proteins whose sizes were not obviously different from that of the lambdaCI B-galactosidase protein. None from this group of fusion proteins was found to react with sera from AIDS patients.

The HTLV-III DNA inserts from $Lac^+$ ORF clones were mapped to specific segments in the HTLV-III genome using Southern blotting procedures. In these studies, each plasmid clone was labelled with $^{32}P$ by nick-translation and hybridized to a battery of HTLV-III DNA restriction fragments. This hybridization analysis mapped all of the $Lac^+$ ORF clones into four open reading frame segments designated ORF-A, ORF-B, ORF-C, and ORF-D (FIG. 2*a*) consistent with the DNA sequencing data. The open reading frames ORF-A and -B, corresponding to the coding regions of the gag and pol genes, are 1.5 Kb and 3.0 Kb long, respectively. ORF-C is about 0.6 Kb long, slightly overlaps with the ORF-B region, encoding a polypeptide of 21 Kd. The location of ORF-C and its overlap with the pol gene are reminiscent of the structure of the env genes in HTLV-I and -II. However, ORF-C, designated as the short open reading frame (sor), is too short to code for the entire envelope protein. The fourth open reading frame, ORF-D, is 2.5 Kb long and could encode both a large precursor of the major envelope glycoprotein and another protein derived from the 3' terminus, which may be analogous to the lor products of HTLV-I and -II. This gene region of HTLV-III, designated env-lor, is at least twice as long as the lor of HTLV-I and HTLV-II and it is presently unclear whether single or multiple proteins are encoded herein.

Both Southern blotting and DNA sequencing studies were employed to analyze a number of clones. As shown in FIG. 2*b*, the $Lac^+$ ORF clones expressing fusion proteins immunoreactive with sera from AIDS patients were located in ORF-A (e.g. #175 and #191), ORF-B (e.g. #13, 31, and 162), or ORF-D (e.g. #113, 121, and 127) and not in the sor region. Not all peptides in these regions were immunoreactive, e.g. ORF clone #76 located in ORF-D.

Analysis of the open reading frame structures in HTLV-III posed questions as to which open reading frame(s) corresponds to the env gene. It is possible that the env-lor region in HTLV-III contains all or a part of the env gene in addition to the presumed lor gene. Recent evidence suggests that the lor in HTLV-I encodes a 42 Kd protein involved in the process of viral activation and transformation. When the lysate of one of the ORF clones (#127 in FIG. 2*b*) was tested against sera from 20 AIDS patients and 12 healthy normals in a strip radioimmunoassay based on the Western blot technique, immunoreactivity against the lambdaCI-HTLV-III-B-galactasidase fusion polypeptide was detected in the sera from 19 of the AIDS patients and none from normal controls. This result indicates that the protein encoded by the portion of the env-lor region contained in ORF clone #127 is produced in HTLV-III infected cells and induces antibody production in most if not all AIDS patients.

INDUSTRIAL APPLICABILITY

This invention has industrial applicability in screening for the presence of HTLV-III DNA in body fluids and the diagnosis of AIDS.

EQUIVALENTS

Those skilled in the art will recognize, or be able to ascertain, using no more than routine experimentation, numerous equivalents to the specific substances and procedures described herein. Such equivalents are considered to be within the scope of this invention and are covered by the following claims.

The invention claimed is:

1. A method comprising the step of forming a nucleic acid complex comprising a double-stranded region and two single-stranded regions;

wherein each single-stranded-region is longer than the double-stranded region;

wherein the nucleic acid complex comprises a Human Immunodeficiency Virus Type-1 (HIV-1) nucleic acid of a bodily fluid obtained from a subject and a nucleic acid having a nucleotide sequence comprising an HIV-1 nucleotide sequence as depicted in FIG. 3, or a portion thereof;

wherein the HIV-1 nucleic acid specifically hybridizes to a nucleic acid complementary to the nucleotide sequence of FIG. 3;

wherein the nucleic acid complex is formed outside of a mammalian cell;

wherein the nucleic acid complex is formed outside of a viral particle;

wherein the double-stranded region is formed between the HIV-1 nucleic acid and the nucleic acid;

wherein the nucleic acid is not a transfer RNA and does not form a nucleic acid complex with HTLV-I or HTLV-II nucleic acids;

wherein the nucleic acid comprises a detectable moiety covalently attached to the nucleic acid; and wherein the detectable moiety is not an additional nucleic acid.

2. The method of claim 1, wherein the HIV-1 nucleotide sequence is from nucleotide 3554 to nucleotide 6664 as depicted in FIG. 3.

3. The method of claim 2, wherein the nucleic acid is between 200 base pairs and 500 base pairs in length.

4. The method of claim 2, wherein the nucleic acid is a restriction fragment from the HIV-1 nucleotide sequence.

5. The method of claim 2, wherein the nucleic acid is a fragment randomly generated from the HIV-1 nucleotide sequence.

6. The method of claim 2, wherein the nucleic acid comprises RNA.

7. The method of claim 2, wherein the nucleic acid comprises DNA.

8. A method comprising the step of forming a nucleic acid complex comprising a double-stranded region and two single-stranded regions;

wherein each single-stranded-region is longer than the double-stranded region;

wherein the nucleic acid complex comprises a Human Immunodeficiency Virus Type-1 (HIV-1) nucleic acid of a bodily fluid obtained from a subject and a nucleic acid having a nucleotide sequence specific to HIV-1 comprising an HIV-1 nucleotide sequence as depicted in FIG. 3, or a portion thereof;

wherein the nucleic acid probe specifically hybridizes to the HIV-1 nucleic acid;

wherein the nucleic acid complex is formed outside of a mammalian cell;

wherein the nucleic acid complex is formed outside of a viral particle;

wherein the double-stranded region is formed between the HIV-1 nucleic acid and the nucleic acid;

wherein the nucleic acid is not a transfer RNA and does not form a nucleic acid complex with HTLV-I or HTLV-II nucleic acids; and wherein the nucleic acid is attached to a non HIV-1 nucleic acid through a covalent bond.

9. The method of claim 8, wherein the HIV-1 nucleotide sequence is from nucleotide 3554 to nucleotide 6664 as depicted in FIG. 3.

10. A method comprising the step of forming a nucleic acid complex comprising a double-stranded region and two single-stranded regions;

wherein each single-stranded-region is longer than the double-stranded region;

wherein the nucleic acid complex comprises a Human Immunodeficiency Virus Type-1 (HIV-1) nucleic acid of a bodily fluid obtained from a subject and a nucleic acid having a nucleotide sequence comprising an HIV-1 nucleotide sequence as depicted in FIG. 3, or a portion thereof;

wherein the nucleic acid specifically hybridizes to the HIV-1 nucleic acid and not to HTLV-I or HTLV-II nucleic acids;

wherein the nucleic acid complex is formed outside of a mammalian cell;

wherein the nucleic acid complex is formed outside of a viral particle;

wherein the double-stranded region is formed between the HIV-1 nucleic acid and the nucleic acid;

wherein the nucleic acid is not a transfer RNA; and wherein the nucleic acid complex is bound to a solid support.

11. The method of claim 10, wherein the HIV-1 nucleotide sequence is from nucleotide 3554 to nucleotide 6664 as depicted in FIG. 3.

12. A method comprising the steps of:

(a) combining (i) a fluid sample suspected of containing a Human Immunodeficiency Virus Type-1 (HIV-1) nucleic acid and (ii) a nucleic acid comprising a nucleotide sequence specific to HIV-1 comprising an HIV-1 nucleotide sequence as depicted in FIG. 3, or a portion thereof; and (b) forming a duplex between the nucleic acid and the HIV-1 nucleic acid if present in the fluid sample but not between the nucleic acid and an HTLV-I or an HTLV-II nucleic acid if present in the fluid sample;

wherein the duplex is formed outside of a mammalian cell;

wherein the duplex is formed outside of a viral particle;

wherein the nucleic acid is not a transfer RNA; and wherein the duplex is bound to a solid support.

13. The method of claim 12, wherein the HIV-1 nucleotide sequence is from nucleotide 3554 to nucleotide 6664 as depicted in FIG. 3.

14. A method comprising the step of forming a nucleic acid complex comprising a double-stranded region and two single-stranded regions;

wherein each single-stranded-region is longer than the double-stranded region;

wherein the nucleic acid complex comprises a Human Immunodeficiency Virus Type-1 (HIV-1) nucleic acid of a bodily fluid obtained from a subject and a nucleic acid having a nucleotide sequence comprising an HIV-1 nucleotide sequence from nucleotide 3554 to nucleotide 6664 as depicted in FIG. 3, or a portion thereof;

wherein the nucleic acid specifically hybridizes to a nucleic acid complementary to the nucleotide sequence from nucleotide 3554 to nucleotide 6664 of FIG. 3;

wherein the nucleic acid complex is formed outside of a mammalian cell;

wherein the nucleic acid complex is formed outside of a viral particle;

wherein the double-stranded region is formed between the HIV-1 nucleic acid and the nucleic acid;

wherein the nucleic acid is not a transfer RNA and does not form a nucleic acid complex with HTLV-I or HTLV-II nucleic acids;

wherein the nucleic acid comprises a detectable moiety covalently attached to the nucleic acid; and wherein the detectable moiety is not an additional nucleic acid.

15. The method of claim 14, wherein the nucleic acid probe is from the pol or env sequence region.

16. The method of claim 14, wherein the nucleic acid is from an approximately 2.3 kb Kpn1-Kpn1 restriction fragment, an approximately 1.0 kb EcoRI-EcoRI restriction fragment, or an EcoRI-BglII restriction fragment comprising env sequences.

17. A method comprising the step of forming a nucleic acid complex comprising a double-stranded region and two single-stranded regions;

wherein each single-stranded-region is longer than the double-stranded region;

wherein the nucleic acid complex comprises a Human Immunodeficiency Virus Type-1 (HIV-1) nucleic acid of a bodily fluid obtained from a subject and a nucleic acid having a nucleotide sequence specific to HIV-1 comprising an HIV-1 nucleotide sequence from nucleotide 3554 to nucleotide 6664 as depicted in FIG. 3, or a portion thereof;

wherein the nucleic acid specifically hybridizes to the HIV-1 nucleic acid;

wherein the nucleic acid complex is formed outside of a mammalian cell;

wherein the nucleic acid complex is formed outside of a viral particle;

wherein the double-stranded region is formed between the HIV-1 nucleic acid and the nucleic acid;

wherein the nucleic acid is not a transfer RNA and does not form a nucleic acid complex with HTLV-I or HTLV-II nucleic acids; and wherein the nucleic acid is attached to a non-HIV-1 nucleic acid through a covalent bond.

18. The method of claim 17, wherein the nucleic acid is from the pol or env sequence region.

19. A method comprising the step of forming a nucleic acid complex comprising a double-stranded region and two single-stranded regions;

wherein each single-stranded-region is longer than the double-stranded region;

wherein the nucleic acid complex comprises a Human Immunodeficiency Virus Type-1 (HIV-1) nucleic acid of a bodily fluid obtained from a subject and a nucleic acid having a nucleotide sequence comprising an HIV-1 nucleotide sequence from nucleotide 3554 to nucleotide 6664 as depicted in FIG. 3, or a portion thereof;

wherein the nucleic acid specifically hybridizes to the HIV-1 nucleic acid of nucleotide 3554 to nucleotide 6664 as depicted in FIG. 3, and not to HTLV-I or HTLV-II nucleic acids;

wherein the nucleic acid complex is formed outside of a mammalian cell;

wherein the nucleic acid complex is formed outside of a viral particle;

wherein the double-stranded region is formed between the HIV-1 nucleic acid and the nucleic acid;

wherein the nucleic acid is not a transfer RNA; and wherein the nucleic acid complex is formed in an environment comprising a compound selected from the group consisting of sodium citrate, polyvinylpyrrolidone, Ficoll and bovine serum albumin.

20. The method of claim 19, wherein the nucleic acid is from the pol or env sequence region.

21. A method comprising the steps of:

(a) combining (i) a fluid sample suspected of containing a Human Immunodeficiency Virus Type-1 (HIV-1) nucleic acid; and (ii) a nucleic acid comprising a nucleotide sequence specific to HIV-1 comprising an HIV-1 nucleotide sequence from nucleotide 3554 to nucleotide 6664 as depicted in FIG. 3, or a portion thereof; and (b) forming a duplex between the nucleic acid and the HIV-1 nucleic acid if present in the fluid sample but not between the nucleic acid and an HTLV-I or an HTLV-II nucleic acid if present in the fluid sample;

wherein the duplex is formed outside of a mammalian cell;

wherein the duplex is formed outside of a viral particle;

wherein the nucleic acid is not a transfer RNA; and wherein the nucleic acid is attached to a non-HIV-1 nucleic acid through a covalent bond.

22. The method of claim 21, wherein the nucleic acid is from the pol or env sequence region.

* * * * *